United States Patent
Turner et al.

(10) Patent No.: US 9,090,592 B2
(45) Date of Patent: Jul. 28, 2015

(54) HETEROCYCLIC COMPOUNDS AND THEIR USE AS GLYCOGEN SYNTHASE KINASE-3 INHIBITORS

(75) Inventors: Sean Colm Turner, Ludwigshafen (DE); Helmut Mack, Ludwigshafen (DE); Margaretha Henrica Maria Bakker, Ludwigshafen (DE); Marcel Van Gaalen, Ludwigshafen (DE); Carolin Hoft, Ludwigshafen (DE); Wilfried Hornberger, Ludwigshafen (DE)

(73) Assignee: AbbVie Deutschland GmbH & Co. KG, Wiesbaden (DE)

( * ) Notice: Subject to any disclaimer, the term of this patent is extended or adjusted under 35 U.S.C. 154(b) by 0 days.

(21) Appl. No.: 13/339,884

(22) Filed: Dec. 29, 2011

(65) Prior Publication Data
US 2012/0172376 A1  Jul. 5, 2012

Related U.S. Application Data

(60) Provisional application No. 61/521,868, filed on Aug. 10, 2011, provisional application No. 61/428,478, filed on Dec. 30, 2010.

(51) Int. Cl.
| | |
|---|---|
| *C07D 215/46* | (2006.01) |
| *C07D 405/14* | (2006.01) |
| *C07D 401/12* | (2006.01) |
| *C07D 401/14* | (2006.01) |

(52) U.S. Cl.
CPC ............ C07D 405/14 (2013.01); C07D 401/12 (2013.01); C07D 401/14 (2013.01); C07D 215/46 (2013.01)

(58) Field of Classification Search
CPC .. C07D 215/46; C07D 401/12; C07D 401/14; C07D 405/14; A61K 31/4706; A61K 31/50; A61K 31/505
USPC ...................................................... 546/159
See application file for complete search history.

(56) References Cited

U.S. PATENT DOCUMENTS

| | | |
|---|---|---|
| 7,037,918 B2 | 5/2006 | Nuss et al. |
| 8,158,661 B2 | 4/2012 | Medina Padilla et al. |
| 8,207,216 B2 | 6/2012 | Kozikowski et al. |
| 8,236,858 B2 | 8/2012 | Peleg-Shulman et al. |
| 8,318,793 B2 | 11/2012 | Turner et al. |
| 8,426,425 B2 | 4/2013 | Jimenez et al. |
| 8,592,437 B2 | 11/2013 | Lochead et al. |
| 8,686,042 B2 | 4/2014 | Gil et al. |

FOREIGN PATENT DOCUMENTS

| | | | |
|---|---|---|---|
| WO | 99/21835 | * | 5/1999 |
| WO | 2008/046919 | * | 4/2008 |
| WO | 2009/130317 | * | 10/2009 |

OTHER PUBLICATIONS

Zhang, J Neurochemistry, vol. 75, No. 6, 2000, pp. 2346-2357.*
Spillantini, Neurodegenerative diseases and Tau pathology, vol. 21, No. 10, 1995, pp. 428-433.*
Ishiguro, FEBS vol. 325, No. 3, pp. 167-172, Jul. 1993.*
Mandelkow, FEBS vol. 314, No. 3, pp. 315-321, Dec. 1992.*
Cowper-Smith, C.D. et al., "Delayed administration of a potent cyclin dependent kinase and glycogen synthase kinase 3 beta inhibitor produces long-term neuroprotection in a hypoxia-ischemia model of brain injury," Neurosci. (2008) 155:864-875.
De Sarno, P. et al., "Lithium prevents and ameliorates experimental autoimmune encephalomyelitis," J. Immunol. (2008) 181:338-345.
Gould, T.D. et al., "AR-A014418, a selective GSK-3 inhibitor, produces antidepressant-like effects in the forced swim test," Int. J. Neuropsychopharmacology (2004) 7:387-390.
Koros, E. et al., "The role of glycogen synthase kinase-3beta in schizophrenia," Drug News Perspect (2007) 20 (7):437-445.
Kypta, R.M. et al., "GSK-3 inhibitors and their potential in the treatment of Alzheimer's disease," Exp. Opin. Ther. Patents (2005) 15(10):1315-1331.
Martin, M. et al., "Toll-like receptor-mediated cytokine production is differentially regulated by glycogen synthase kinase 3," Nature Immun. (2005) 6(8):777-784.
Martins, D.F. et al., "The antinociceptive effects of AR-A014418, a selective inhibitor of glycogen synthase kinase-3 beta, in mice," J. of Pain (2010) 1-8.
Peineau, S. et al., "LTP inhibits LTD in the hippocampus via regulation of GSK3beta," Neuron (2007) 53:703-717.
Rockenstein, E. et al., "Neuroprotective effects of regulators of the glycogen synthase kinase-3beta signaling pathway in a transgenic model of Alzheimer's disease are associated with reduced amyloid precursor protein phosphorylation," J. Neurosci. (2007) 27(8):1981-1991.

(Continued)

*Primary Examiner* — D M Seaman
(74) *Attorney, Agent, or Firm* — Lisa V. Mueller; Michael Best & Friedrich LLP

(57) ABSTRACT

The present invention relates to novel heterocyclic compounds of formula I

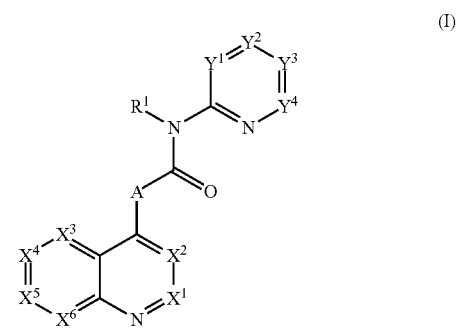

(I)

wherein the variables are as defined in the claims or the description,
which are useful for inhibiting glycogen synthase kinase 3 (GSK-3), compositions containing the compounds, their use for preparing a medicament for the treatment of a medical disorder susceptible to the treatment with a compound that modulates, preferably inhibits, the activity of glycogen synthase kinase 3β, and methods of treatment of medical disorders susceptible to treatment with a compound that modulates glycogen synthase kinase 3β activity using the compounds.

29 Claims, No Drawings

(56) References Cited

OTHER PUBLICATIONS

Soos, T.J. et al., "CDK/GSK-3 inhibitors as a new approach for the treatment of proliferative renal diseases," Drug News perspect. (2006) 19(6):325-328.
Szczepankiewicz, A. et al., "Association analysis of the GSK-3beta T-50C gene polymorphism with schizophrenia and bipolar disorder," Neuropsychobiology (2006) 53:51-56.
Takada, Y. et al., "Genetic deletion of glycogen synthase kinase-3beta abrogates activation of IkBalpha kinase, JNK, Akt, and p44/p42 MAPK but potentiates apoptosis induced by tumor necrosis factor," J. Biol. Chem. (2004) 279 (38):39541-39554.
Whittle, B.J.R. et al., "Reduction of experimental colitis in the rat by inhibitors of glycogen synthase kinase-3beta," Br J. Pharm. (2006) 147:575-582.
Aho et al., Dement. Geriatr. Cogn. Disord., 25: 423-432 (2008).
Cole et al., J. Biol. Chem., 279(48): 50176-50180 (2004).
Engel et al., J. Neurochem., 99: 1445-1455 (2006).
Engel et al., J. Neurosci., 26(19): 5083-5090 (2006).
Hanger et al., Neurosci. Lett., 147: 58-62 (1992).
Leroy et al., Neuropathol. Appl. Neurobiol., 33: 43-55 (2007).
Lucas et al., EMBO J., 20(1-2): 27-39 (2001).
Luna-Munoz et al., J. Alzheimers Dis., 12: 365-375 (2007).
Medina et al., Front. Mol. Neurosci., 4(24): 1-10 (2011).
Noble et al., PNAS, 102(19): 6990-6995 (2005).
Onishi et al., J. Neurochem., 119: 1330-1340 (2011).
Pei et al., J. Neuropathol. Exp. Neurol., 56(1): 70-78 (1997).
Rubinfeld et al., Science, 272: 1023-1026 (1996).

* cited by examiner

HETEROCYCLIC COMPOUNDS AND THEIR USE AS GLYCOGEN SYNTHASE KINASE-3 INHIBITORS

CROSS-REFERENCE TO RELATED APPLICATIONS

This claims priority to U.S. Provisional Patent Application No. 61/521,868, filed on Aug. 10, 2011 and U.S. Provisional Patent Application No. 61/428,478, filed on Dec. 30, 2010, the contents of all of which are herein incorporated by reference.

TECHNICAL FIELD

The present invention relates to novel heterocyclic compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β, with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: behavioural and psychiatric symptoms of dementia, Parkinson's disease, tauopathies (e.g. frontotemporoparietal dementia, corticobasal degeneration, Pick's disease, progressive supranuclear palsy, argyophilic grain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma.

GSK-3β may also have utility in the treatment of pain.

GSK-3β may further have utility in the treatment of inflammatory diseases, such as rheumatoid arthritis and osteoarthritis.

GSK-3β may also have utility in the treatment of other diseases such as: Non-insulin dependent diabetes and obesity; osteoporosis; manic depressive illness; schizophrenia; alopecia; cancers such as breast cancer, non-small cell lung carcinoma, thyroid cancer, T or B-cell leukemia and several virus-induced tumors.

A review on GSK-3, its functions, its therapeutic potential and its possible inhibitors is given in "Glycogen Synthase Kinase 3 (GSK-3) and its inhibitors: Drug Discovery and Developments" by A. Martinez et al. (editors), John Wiley and Sons, 2006.

WO 03/053330 describes 2-oxindoles substituted in the 3-position with a bicyclic hetaryl group and their use for treating conditions related to glycogen synthase kinase-3. WO 03/082853 describes substituted 2-oxindoles substituted in the 3-position with a monocyclic hetaryl group and their use for treating conditions related to glycogen synthase kinase-3. WO 2005/123672 relates to 2-hydroxyindoles carrying in the 3-position an optionally fused pyrid-2-yl ring and their use for inhibiting kinases. WO 2005/061519 relates to 2-hydroxyindoles carrying in the 3-position a pyrid-2-yl ring fused to an aromatic or heteroaromatic ring and their use for inhibiting kinases.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative and/or inflammatory diseases. More specifically, the goal is to provide novel compounds useful as an active ingredient of a composition that enables prevention and/or treatment of neurodegenerative diseases such as Alzheimer's disease.

It was surprisingly found that the problem is solved by providing a heterocyclic compound of the general formula I

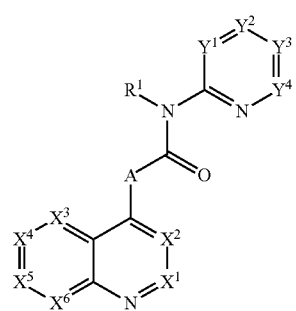

(I)

the stereoisomers, prodrugs, N-oxides, tautomers and/or physiologically tolerated acid addition salts thereof, and the compounds of the general formula I, wherein at least one of the atoms has been replaced by its stable, non-radioactive isotope, wherein A is selected from the group consisting of $CR^{A1}R^{A2}$ and $NR^B$; where
  $R^{A1}$ and $R^{A2}$ are independently of each other selected from the group consisting of hydrogen, $C_1$-$C_2$-alkyl, $C_1$-$C_2$-haloalkyl, $NH_2$ and OH; and
  $R^B$ is selected from H, $C_1$-$C_4$-alkyl and $C_1$-$C_4$-haloalkyl;

$X^1$ and $X^2$ are independently of each other selected from the group consisting of $CR^2$ and N;

$X^3$, $X^4$, $X^5$ and $X^6$ are independently of each other selected from the group consisting of $CR^3$, $CR^4$ and N;
  with the proviso that no more than two of $X^3$, $X^4$, $X^5$ and $X^6$ are $CR^4$;

$Y^1$, $Y^2$, $Y^3$ and $Y^4$ are independently of each other selected from the group consisting of $CR^4$, $CR^5$ and N;
  with the proviso that at most one of $Y^1$, $Y^2$, $Y^3$ and $Y^4$ is N and with the proviso that at most one of $Y^1$, $Y^2$, $Y^3$ and $Y^4$ is $CR^4$; and
  with the proviso that one of $Y^1$, $Y^2$, $Y^3$ and $Y^4$ is $CR^4$ or C—$CF_3$, if none of $X^3$, $X^4$, $X^5$ and $X^6$ is $CR^4$;

$R^1$ is selected from hydrogen, $C_1$-$C_4$-alkyl and $C_1$-$C_4$-haloalkyl;

each $R^2$ is independently selected from the group consisting of hydrogen, OH, halogen (preferably F or Cl, more preferably F), CN, $C_1$-$C_6$-alkyl, $C_1$-$C_6$-haloalkyl, $C_1$-$C_6$-alkoxy, $C_1$-$C_6$-haloalkoxy and $NR^aR^b$;
  or two radicals $R^2$ bonded at the carbon atoms of groups $X^1$ and $X^2$, together with the carbon atoms to which they are bonded, form a 5- or 6-membered saturated or unsaturated ring which may contain 1 or 2 heteroatoms as ring members selected from the group consisting of N, O and S and which optionally carries 1, 2 or 3 substituents $R^6$;

each $R^3$ is independently selected from the group consisting of hydrogen, CN, $NR^aR^b$, OH, halogen (preferably F or Cl, more preferably F), $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^7$ and wherein Ar may also be bonded via a $CH_2$ group;

$R^4$ is a C-bound saturated or partially unsaturated monocyclic 3-, 4-, 5-, 6- or 7-membered heterocyclic ring containing 1, 2 or 3 heteroatoms or heteroatom-containing groups selected from O, N, S, NO, SO and $SO_2$ as ring members, where the heterocyclic ring optionally carries 1, 2 or 3 C- or N-bound substituents $R^8$;

$R^5$ is selected from the group consisting of hydrogen, CN, $NR^aR^b$, OH, halogen (preferably F or Cl, more preferably F), $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^7$ and wherein Ar may also be bonded via a $CH_2$ group;

$R^6$ and $R^8$, independently of each other and independently of each occurrence, are selected from the group consisting of CN, $NR^aR^b$, OH, halogen (preferably F or Cl, more preferably F), $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$ and an aromatic radical Ar, which is selected from the group consisting of phenyl and a 5- or 6-membered N- or C-bound heteroaromatic radical comprising one nitrogen atom and optionally 1, 2 or 3 further heteroatoms independently selected from O, S and N as ring members, wherein Ar is unsubstituted or carries one or two radicals $R^7$ and wherein Ar may also be bonded via a $CH_2$ group;

each $R^7$ is independently selected from the group consisting of halogen (preferably F or Cl, more preferably F), CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, a phenyl group and a 5- or 6-membered heteroaromatic radical comprising one nitrogen atom and optionally 1, 2 or 3 further heteroatoms independently selected from O, S and N as ring members, wherein phenyl and the heteroaromatic radical are, independently of each other, unsubstituted or substituted by 1, 2, 3 or 4 radicals selected from halogen, cyano, $C_1$-$C_4$-alkyl, $C_1$-$C_4$-haloalkyl, $C_1$-$C_4$-alkoxy and $C_1$-$C_4$-haloalkoxy; and $R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-haloalkylcarbonyl;
  or $R^a$ and $R^b$ form, together with the nitrogen atom to which they are bonded, a 3-, 4-, 5-, 6- or 7-membered saturated or unsaturated aromatic or non-aromatic N-heterocyclic ring, which may contain 1 further heteroatom or heteroatom containing group selected from the group consisting of O, S, SO, $SO_2$ and N as a ring member.

Thus, the present invention relates to compounds of the formula I as defined herein and in the claims, to the stereoisomers, tautomers, prodrugs and/or physiologically tolerated acid addition salts thereof, and also to compounds of the general formula I, wherein at least one of the atoms has been replaced by its stable, non-radioactive isotope.

According to a further aspect, the present invention relates to a pharmaceutical composition comprising at least one compound of the formula I as defined herein, a stereoisomer, a tautomer, a prodrug and/or a physiologically tolerated acid addition salt thereof or comprising at least one heterocyclic compound as defined above, wherein at least one of the atoms has been replaced by its stable, non-radioactive isotope, optionally together with at least one physiologically acceptable carrier and/or auxiliary substance.

According to a further aspect, the present invention relates to the use of at least one compound of the formula I as defined herein, the stereoisomers, tautomers, prodrugs and/or physiologically tolerated acid addition salts thereof, for the preparation of a medicament for the treatment of a medical disorder susceptible to treatment with a compound that modulates glycogen synthase kinase 3β activity.

According to a further aspect, the present invention relates to a method for treating a medical disorder susceptible to treatment with a compound that modulates glycogen synthase kinase 3β activity, said method comprising administering an effective amount of at least one compound of the formula I as defined herein, a stereoisomer, a tautomer, a prodrug and/or a physiologically tolerated acid addition salt thereof, to a subject in need thereof.

DETAILED DESCRIPTION OF THE INVENTION

Provided the compounds of the formula I of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formula I and/or of their salts.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhäuser Verlag, Basel and Stuttgart, 1966.

In the terms of the present invention, "prodrugs" are compounds which are metabolized in vivo to give the compounds of the invention of formula I. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula I wherein an external nitrogen atom, for example a secondary nitrogen ring atom of the ring $R^4$ or a nitrogen atom of a primary or secondary amino group being a substituent $R^2$, $R^3$, $R^5$, $R^6$, $R^7$ and/or $R^8$ (=at least one of $R^2$, $R^3$, $R^5$, $R^6$, $R^7$ and $R^8$ is $NR^aR^b$, wherein at least one of $R^a$ and $R^b$ is H), forms an amide/peptide bond in that this nitrogen atom is substituted by a $C_1$-$C_4$-alkylcarbonyl group, e.g. by acetyl, propionyl, n-propylcarbonyl, isopropyl-carbonyl, n-butylcarbonyl or tert-butylcarbonyl(pivaloyl), by benzoyl, or by an amino-acid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein R$^x$ and R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds I wherein said nitrogen atom carries a hydrogen atom instead. Also, $R^8$, if bound to a nitrogen ring atom of $R^4$, may be chosen so as to be hydrolysable under metabolic conditions and thus to be one of the above-listed groups (i.a. a $C_1$-$C_4$-alkylcarbonyl group, an aminoacid group bonded via CO or a group —C(=O)—O—CHR$^x$—O—C(=O)—R$^y$).

The compounds of formula I may also be present in the form of the respective tautomers. Tautomery may be present in compounds I wherein $R^2$ or $R^3$ is OH and this substituent is bonded to a carbon atom which is in α-position to a nitrogen ring atom. This results for example in following tautomeric formulae:

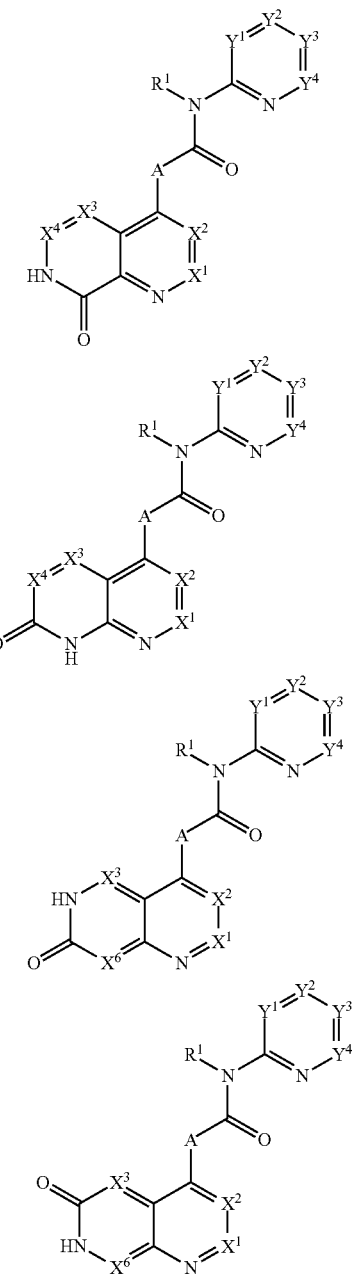

-continued

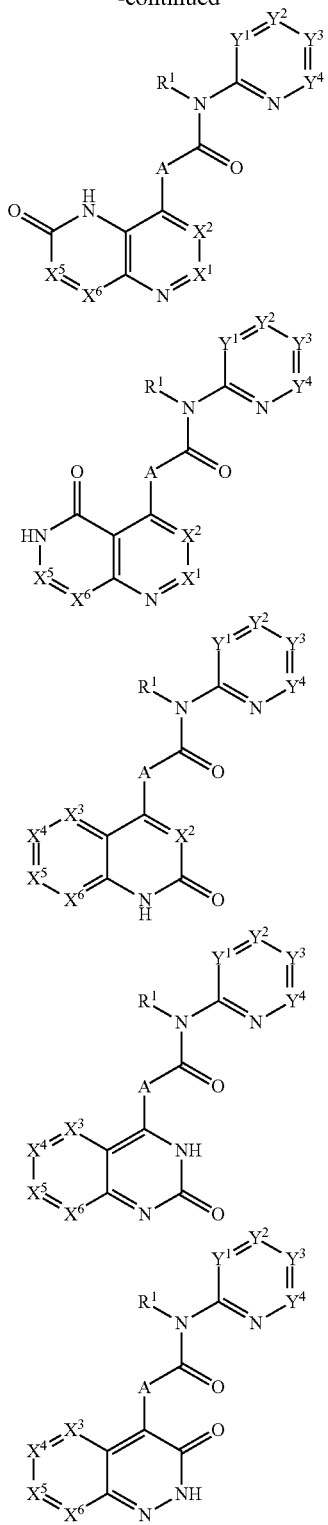

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_2$-Alkyl is methyl or ethyl; $C_1$-$C_3$-alkyl is additionally n-propyl or isopropyl.

$C_1$-$C_4$-Alkyl is a straight-chain or branched alkyl group having from 1 to 4 carbon atoms. Examples are methyl, ethyl, n-propyl, isopropyl, n-butyl, 2-butyl(sec-butyl), isobutyl and tert-butyl.

$C_1$-$C_6$-Alkyl is a straight-chain or branched alkyl group having from 1 to 6 carbon atoms. Examples include the residues mentioned above for $C_1$-$C_4$-alkyl and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_2$-Haloalkyl is an alkyl group having 1 or 2 carbon atoms (as mentioned above), where at least one of the hydrogen atoms, e.g. 1, 2, 3, 4 or 5 hydrogen atoms in these groups are replaced by halogen atoms as mentioned above, such as chloromethyl, dichloromethyl, trichloromethyl, fluoromethyl, difluoromethyl, trifluoromethyl, bromomethyl, chlorofluoromethyl, dichlorofluoromethyl, chlorodifluoromethyl, 1-chloroethyl, 1-bromoethyl, 1-fluoroethyl, 2-chloroethyl, 2-bromoethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

$C_1$-$C_4$-Haloalkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by halogen atoms as mentioned above. Examples are, apart those listed above for $C_1$-$C_2$-haloalkyl, 1-chloropropyl, 1-bromopropyl, 1-fluoropropyl, 2-chloropropyl, 2-bromopropyl, 2-fluoropropyl, 3-chloropropyl, 3-bromopropyl, 3-fluoropropyl, 1,1-dichloropropyl, 1,1-difluoropropyl, 2,2-dichloropropyl, 2,2-difluoropropyl, 2,3-dichloropropyl, 2,3-difluoropropyl, 1,3-dichloropropyl, 1,3-difluoropropyl, 3,3-dichloropropyl, 3,3-difluoropropyl, 1,1,2-trichloropropyl, 1,1,2-trifluoropropyl, 1,2,2-trichloropropyl, 1,2,2-trifluoropropyl, 1,2,3-trichloropropyl, 1,2,3-trifluoropropyl, 2,2,3-trichloropropyl, 2,2,3-trifluoropropyl, 3,3,3-trichloropropyl, 3,3,3-trifluoropropyl, 1,1,1-trifluoroprop-2-yl, 1-chlorobutyl, 1-bromobutyl, 1-fluorobutyl, 2-chlorobutyl, 2-bromobutyl, 2-fluorobutyl, 3-chlorobutyl, 3-bromobutyl, 3-fluorobutyl, 4-chlorobutyl, 4-bromobutyl, 4-fluorobutyl, and the like.

$C_1$-$C_6$-Haloalkyl is a straight-chain or branched alkyl group having 1 to 6 carbon atoms (as mentioned above), where at least one of the hydrogen atoms in these groups is replaced by halogen atoms as mentioned above. Examples are, apart those listed above for $C_1$-$C_4$-haloalkyl, chloropentyl, bromopentyl, fluoropentyl, chlorohexyl, bromo-hexyl, fluorohexyl, and the like.

$C_1$-$C_2$-Fluoroalkyl (=fluorinated $C_1$-$C_2$-alkyl) is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl.

$C_1$-$C_4$-Fluoroalkyl (=fluorinated $C_1$-$C_4$-alkyl) is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like.

$C_1$-$C_6$-Fluoroalkyl (=fluorinated $C_1$-$C_6$-alkyl) is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 65-fluorohexyl, (R)-6-fluorohexyl, (S)-6-fluorohexyl, and the like.

$C_1$-$C_4$-Alkoxy is a straight-chain or branched alkyl group having from 1 to 4 carbon atoms, which is bound to the remainder of the molecule via an oxygen atom. Examples include methoxy, ethoxy, n-propoxy, isopropoxy, n-butoxy, 2-butoxy, isobutoxy and tert-butoxy.

$C_1$-$C_6$-Alkoxy is a straight-chain or branched alkyl group having from 1 to 6 carbon atoms, which is bound to the remainder of the molecule via an oxygen atom. Examples include, apart those listed above for $C_1$-$C_4$-alkoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy (which is also termed $C_1$-$C_6$-haloalkoxy), in particular fluorinated $C_1$-$C_6$-alkoxy (also termed $C_1$-$C_6$-fluoroalkoxy) is a straight-chain or branched alkoxy group having from 1 to 6, in particular 1 to 4 carbon atoms (=fluorinated $C_1$-$C_4$-alkoxy), wherein at least one, e.g. 1, 2, 3, 4 or all of the hydrogen atoms are replaced by a halogen atoms, in particular fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_4$-Alkylcarbonyl is a straight-chain or branched alkyl group having from 1 to 4 carbon atoms), which is bound to the remainder of the molecule via a carbonyl group (CO), such as in acetyl, propionyl, isopropylcarbonyl, butylcarbonyl, sec-butylcarbonyl, isobutylcarbonyl, and tert-butylcarbonyl.

$C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonyl, pentylcarbonyl, hexylcarbonyl and the constitutional isomers thereof.

$C_1$-$C_4$-Haloalkylcarbonyl is a straight-chain or branched haloalkyl group having from 1 to 4 carbon atoms as defined above, which is bound to the remainder of the molecule via a carbonyl group (CO)

$C_1$-$C_6$-Haloalkylcarbonyl is a straight-chain or branched haloalkyl group having from 1 to 6 carbon atoms as defined above, which is bound to the remainder of the molecule via a carbonyl group (CO)

$C_1$-$C_4$-Fluoroalkylcarbonyl is a straight-chain or branched fluoroalkyl group having from 1 to 4 carbon atoms as defined above, which is bound to the remainder of the molecule via a carbonyl group (CO)

$C_1$-$C_6$-fluoroalkylcarbonyl is a straight-chain or branched fluoroalkyl group having from 1 to 6 carbon atoms as defined above, which is bound to the remainder of the molecule via a carbonyl group (CO)

$C_1$-$C_6$-Alkoxycarbonyl is a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

$C_1$-$C_6$-Haloalkoxycarbonyl is a straight-chain or branched haloalkoxy group having from 1 to 6, especially 1 to 4 carbon atoms (=$C_1$-$C_4$-haloalkoxycarbonyl), in particular 1 to 3 carbon atoms (=$C_1$-$C_3$-haloalkoxycarbonyl) as defined above, which is bound to the remainder of the molecule via a carbonyl group (CO).

$C_1$-$C_6$-Fluoroalkoxycarbonyl is a straight-chain or branched fluorooalkoxy group having from 1 to 6, especially 1 to 4 carbon atoms (=$C_1$-$C_4$-fluoroalkoxycarbonyl), in particular 1 to 3 carbon atoms (=$C_1$-$C_3$-fluoroalkoxycarbonyl) as defined above, which is bound to the remainder of the molecule via a carbonyl group (CO).

$C_3$-$C_6$-Cycloalkyl is a cycloaliphatic radical having from 3 to 6 C atoms, such as cyclopropyl, cyclobutyl, cyclopentyl and cyclohexyl. $C_3$-$C_4$-cycloalkyl is a cycloaliphatic radical having from 3 to 4 C atoms, such as cyclopropyl and cyclobutyl.

$C_3$-$C_7$-Cycloalkyl is a cycloaliphatic radical having from 3 to 7 C atoms, such as cyclopropyl, cyclobutyl, cyclopentyl, cyclohexyl and cycloheptyl.

$C_3$-$C_6$-Halocycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a halogen atoms, preferably by fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_7$-Halocycloalkyl is a cycloaliphatic radical having from 3 to 7 C atoms, such as cyclopropyl, cyclobutyl, cyclopentyl, cyclohexyl and cycloheptyl, wherein at least one, e.g. 1, 2, 3, 4 or all of the hydrogen atoms are replaced by a halogen atoms, preferably by fluorine atoms. Examples include, apart those listed above for $C_3$-$C_6$-fluorocycloalkyl, 1-fluorocycloheptyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

$C_2$-$C_4$-Alkenyl is a singly unsaturated hydrocarbon radical having 2, 3 or 4 C-atoms and one C—C double bond, e.g. vinyl, allyl (2-propen-1-yl), 1-propen-1-yl, 2-propen-2-yl, buten-1-yl, buten-2-yl, buten-3-yl, methallyl (2-methylprop-2-en-1-yl) and the like.

$C_2$-$C_4$-Haloalkenyl is a singly unsaturated hydrocarbon radical having 2, 3 or 4 C-atoms, wherein at least one, e.g. 1, 2, 3, 4 or all of the hydrogen atoms are replaced by halogen atoms, preferably by fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

Examples for 5- or 6-membered N- or C-bound heteroaromatic radicals comprising one nitrogen atom and optionally 1, 2 or 3 further heteroatoms independently selected from O, S and N as ring members are pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-3-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for 5- or 6-membered N- or C-bound heteroaromatic radicals comprising 1, 2 or 3 heteroatoms independently selected from O, S and N as ring members are furan-2-yl, furan-3-yl, thien-2-yl, thien-3-yl, pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-3-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for N-bound 3-, 4-, 5-, 6- or 7-membered saturated or unsaturated aromatic or non-aromatic N-heterocyclic rings, which may contain 1 further heteroatom or heteroatom-containing group selected from the group consisting of O, S, SO, $SO_2$ and N as a ring member (thus as rings formed by $R^a$ and $R^b$ together with the nitrogen atom to which they are bound), are aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-1-yl, [1,2,3]-triazolidin-1-yl, [1,2,3]-triazolidin-2-yl, [1,2,4]-triazolidin-1-yl, [1,2,4]-triazolidin-4-yl, piperidin-1-yl, piperazin-1-yl, morpholin-4-yl, thiomorpholin-1-yl, 1-oxohiomorpholin-1-yl, 1,1-dioxothiomorpholin-1-yl, azepan-1-yl, azirin-1-yl, azetin-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

Examples for C-bound saturated or partially unsaturated monocyclic 3-, 4-, 5-, 6- or 7-membered heterocyclic ring containing 1, 2 or 3 heteroatoms or heteroatom-containing groups selected from O, N, S, NO, SO and $SO_2$ as ring members (i.e. for rings $R^4$) are C-bound oxiranyl, thiiranyl, aziridinyl, oxetanyl, azetidinyl, dihydrofuranyl, tetrahydrofuranyl, dihydrothienyl, tetrahydrothienyl, dihydrothienyl-1-oxide, tetrahydrothienyl-1-oxide, pyrrolinyl, pyrrolidinyl, pyrazolinyl, pyrazolidinyl, imidazolinyl, imidazolidinyl, triazolinyl, triazolidinyl, oxazolinyl, oxazolidinyl, isoxazolinyl isoxazolidinyl, oxadiazolinyl, oxadiazolidinyl, thiazolinyl, thiazolidinyl, isothiazolinyl, isothiazolidinyl, thiadiazolinyl, thiadiazolidinyl, dihydropyranyl, tetrahydropyranyl, dihydrothiopyranyl, tetrahydropyranyl, dihydropyridinyl, tetrahydropyridinyl, piperidinyl, dihydropyridazinyl, tetrahydropyridazinyl, hexahydropyridazinyl, dihydropyrimidinyl, tetrahydropyrimidinyl, hexa-hydropyrimidinyl, dihydropyrazinyl, tetrahydropyrazinyl, piperazinyl, dihydro-[1,4]-oxazinyl, morpholinyl, dihydro-[1,4]-thiazinyl, thiomorpholinyl, thiomorpholinyl-1-oxide, thiomorpholinyl-1-dioxide, dihydroazepinyl, tetrahydroazepinyl, azepanyl, dihydrodiazepinyl, tetrahydrodiazepinyl, diazepanyl and the like.

More precisely, examples for C-bound saturated or partially unsaturated monocyclic 3-, 4-, 5-, 6- or 7-membered heterocyclic ring containing 1, 2 or 3 heteroatoms or heteroatom-containing groups selected from O, N, S, NO, SO and $SO_2$ as ring members (i.e. for rings $R^4$) comprise the following structures:

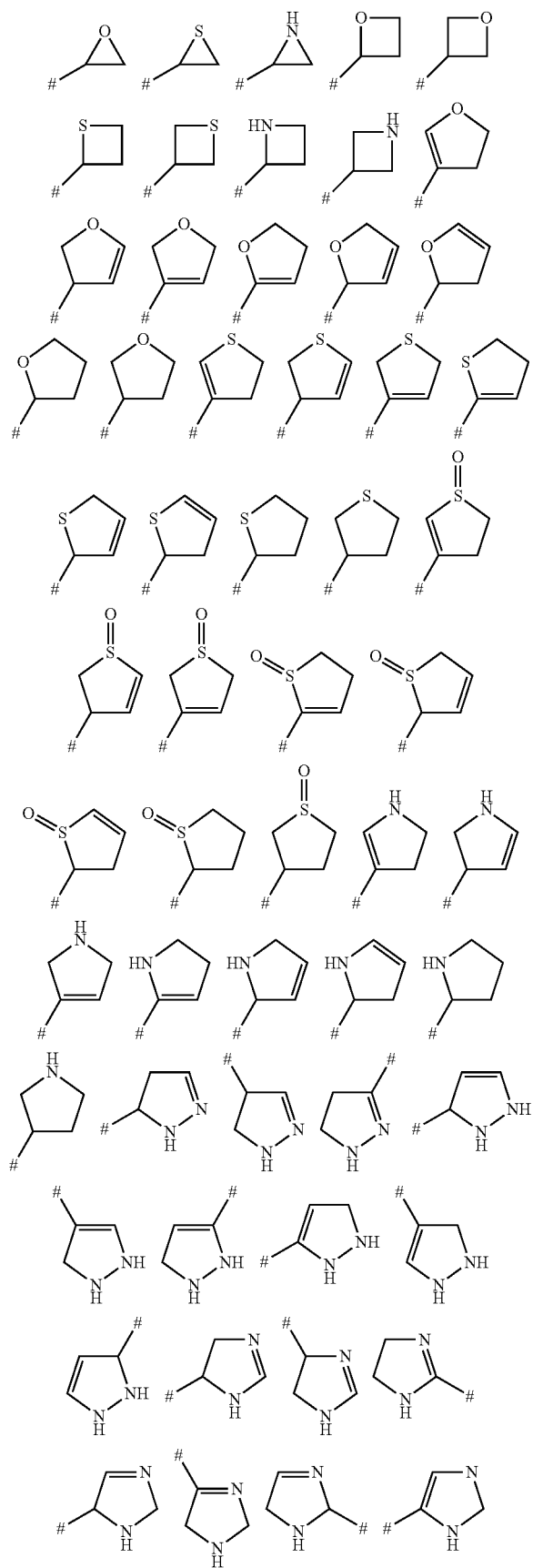
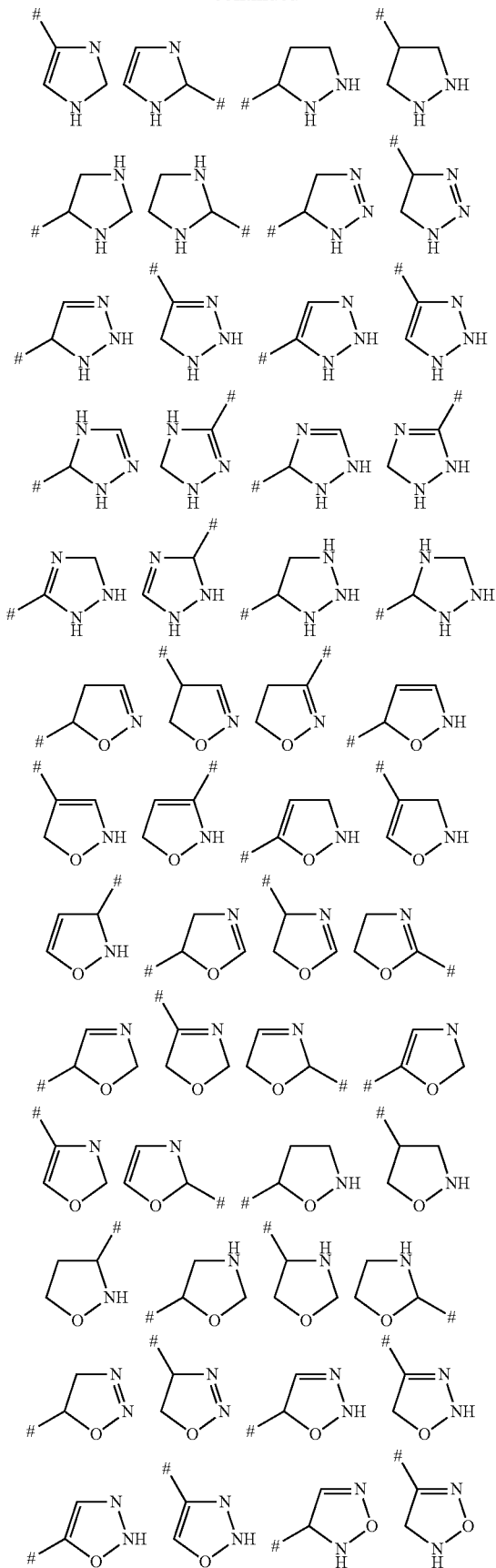

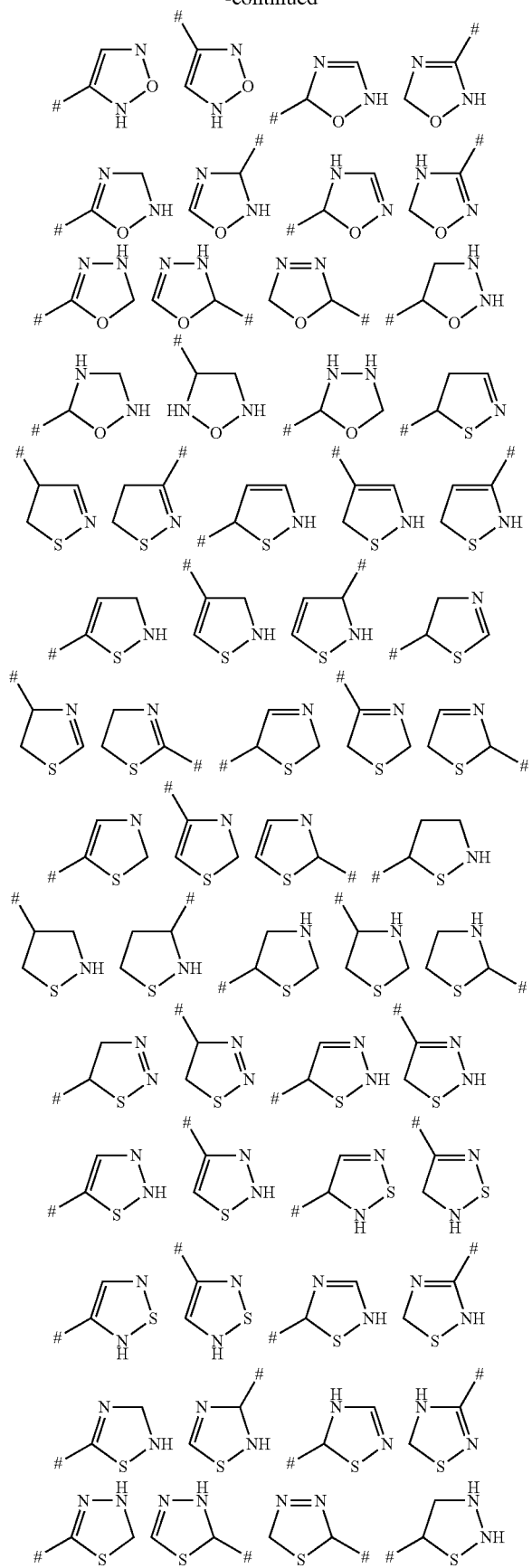
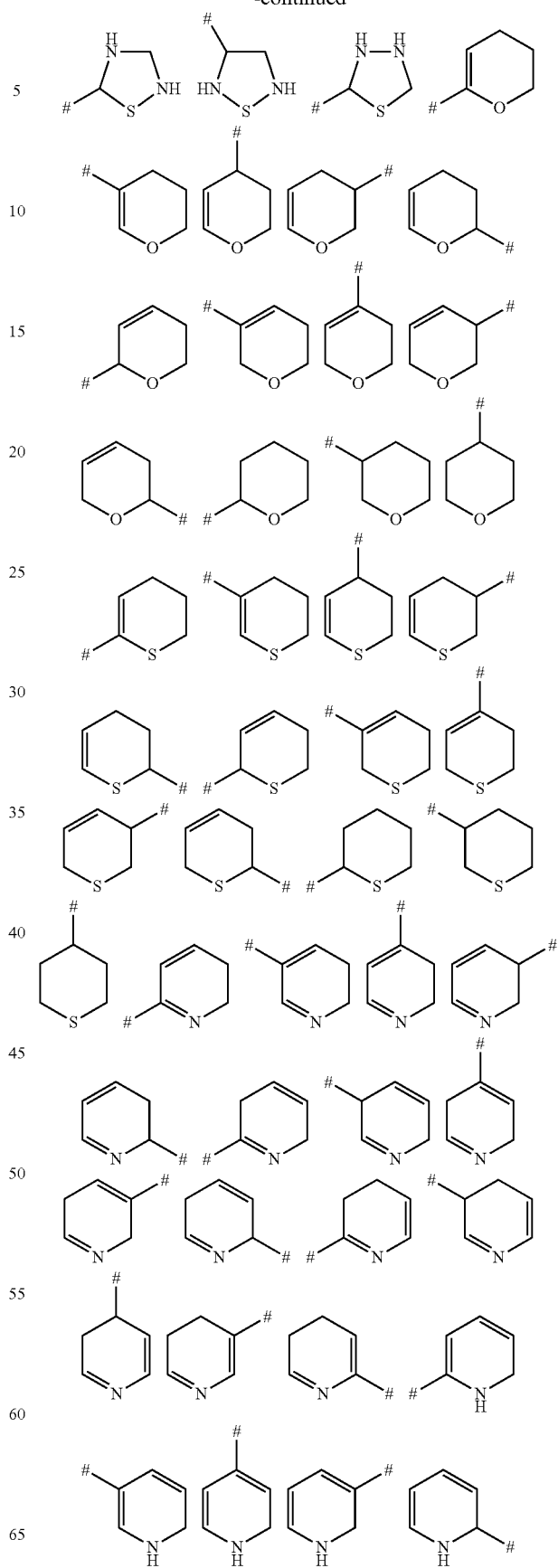

-continued
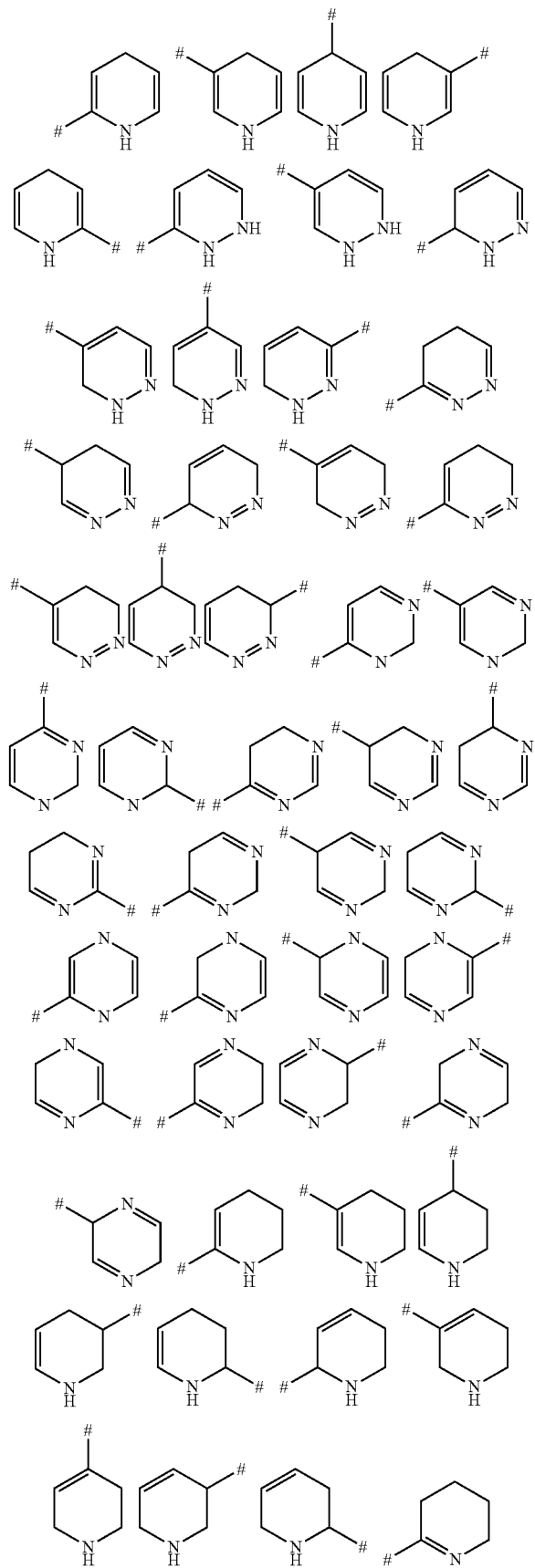
-continued
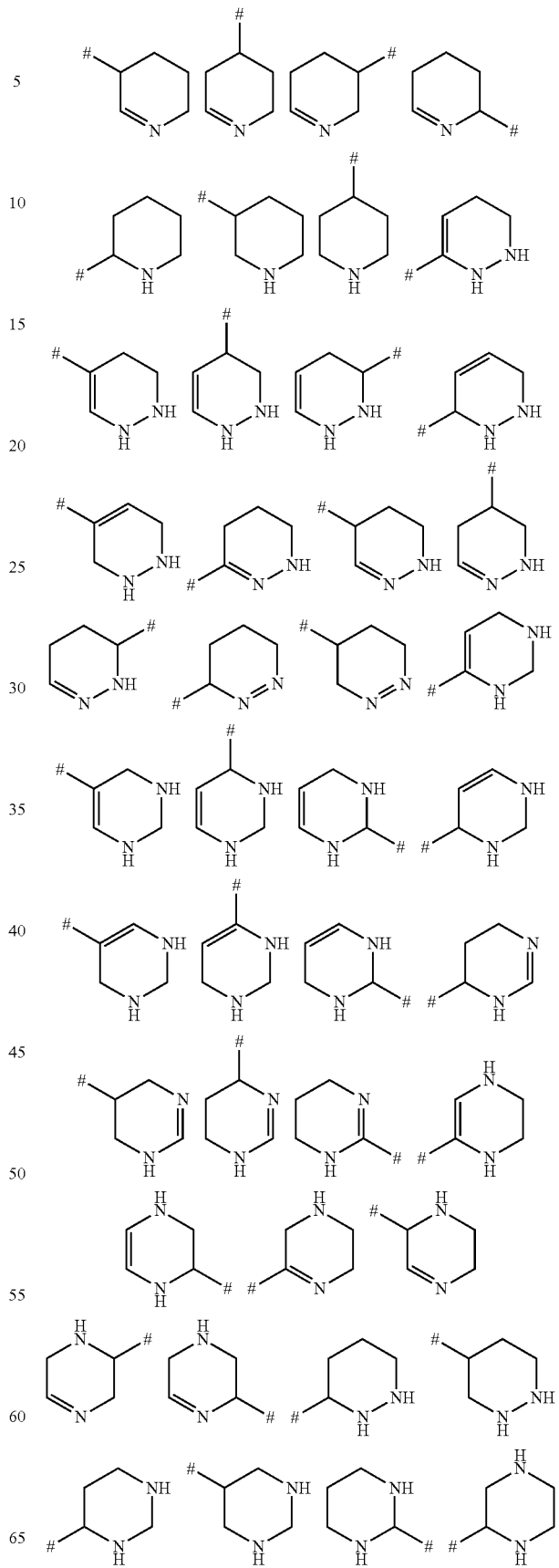

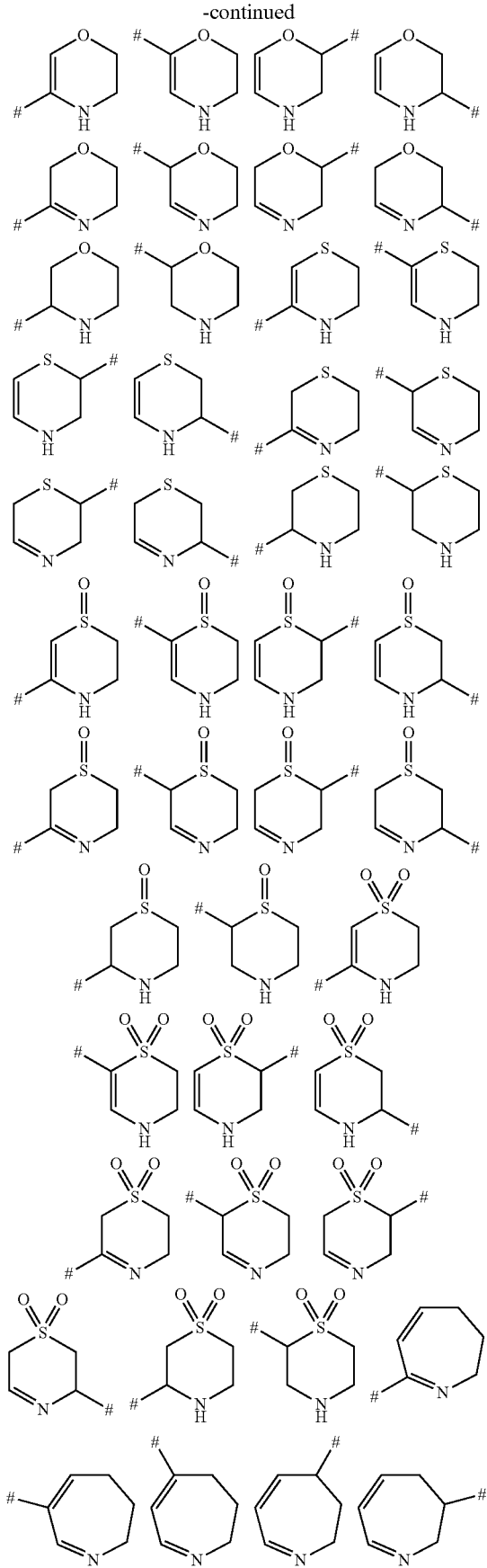
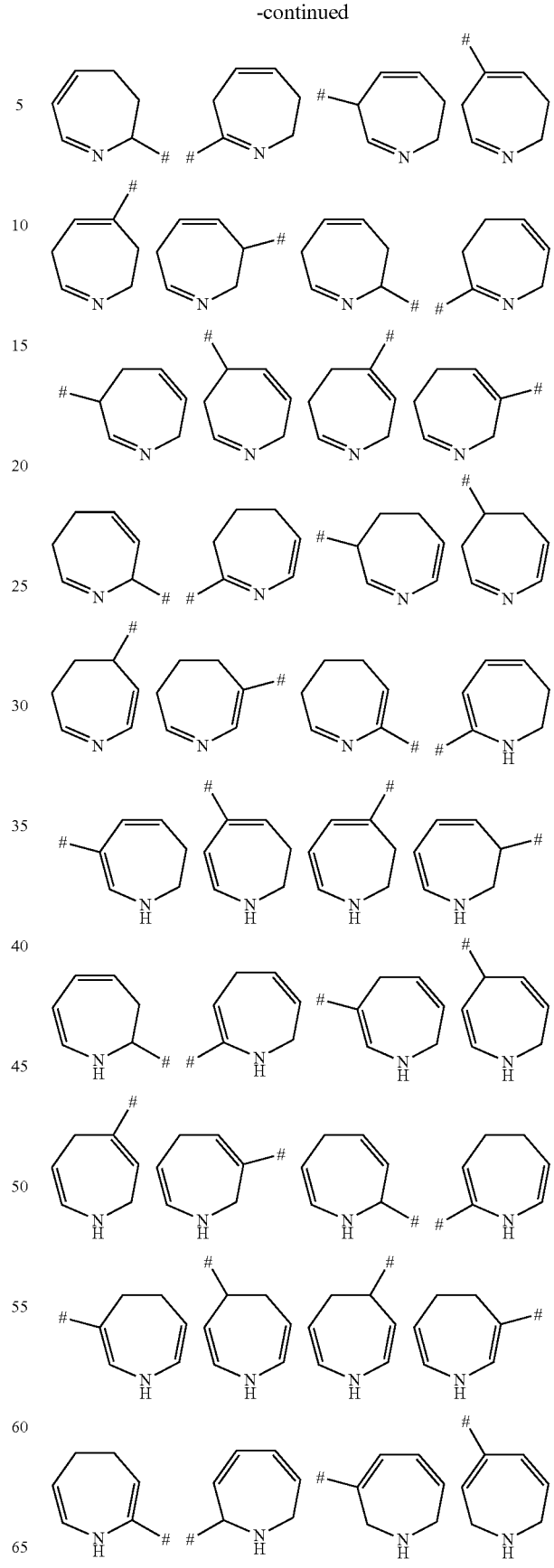

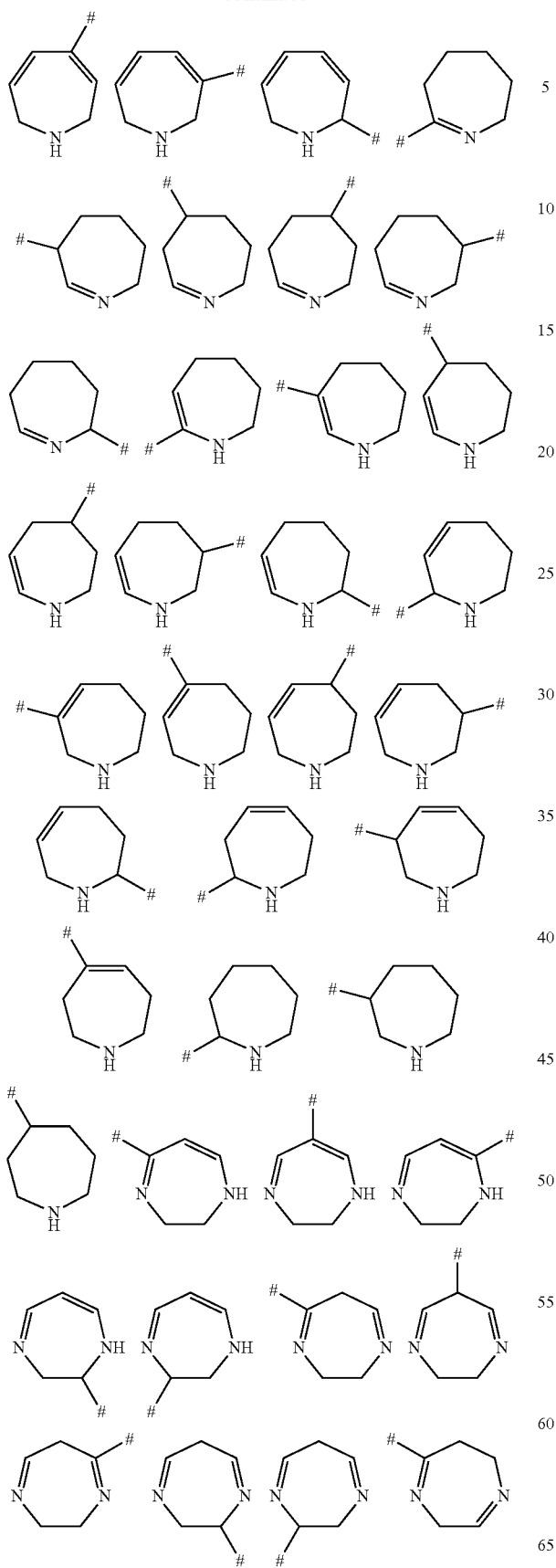
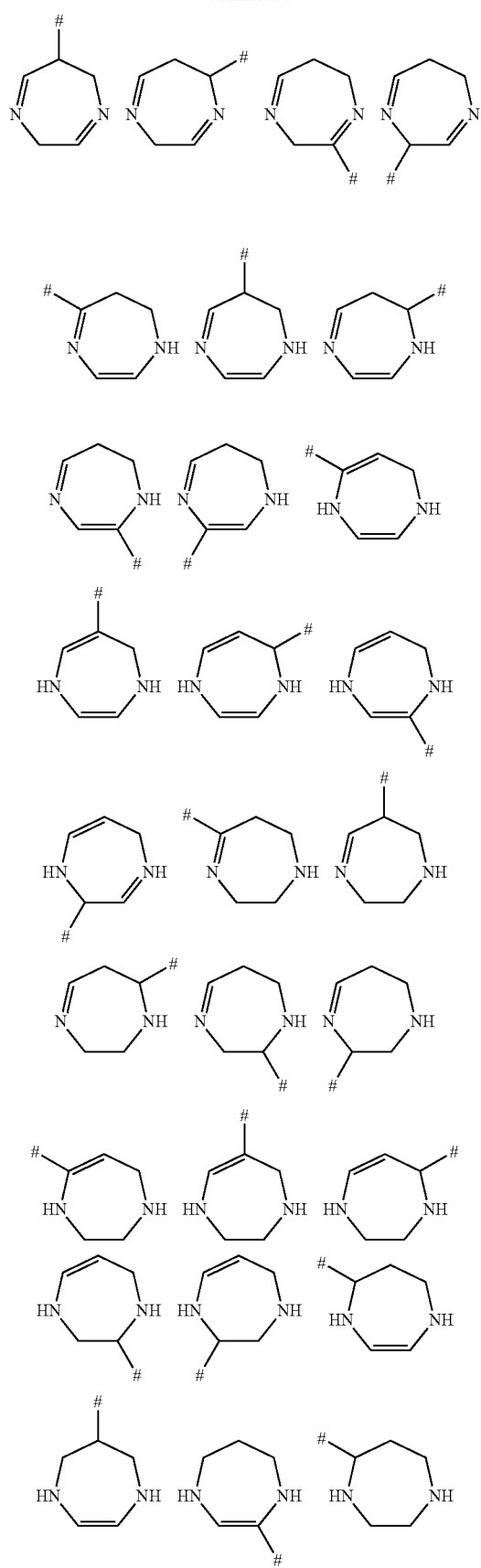

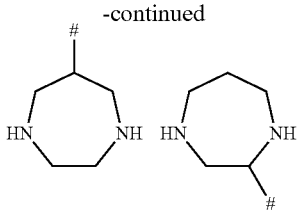

where # is the attachment point to the remainder of the molecule.

The remarks made above and in the following with respect to preferred aspects of the invention, e.g. to preferred meanings of the variables $X^1, X^2, X^3, X^4, X^5, X^6, Y^1, Y^2, Y^3, Y^4, R^1, R^2, R^3, R^4, R^5, R^6, R^7, R^8, R^a, R^b, R^{A1}, R^{A2}, R^B$ of compounds I, to preferred compounds I and to preferred embodiments of the method or the use according to the invention, apply in each case on their own or in particular to combinations thereof.

In one embodiment of the invention one of $Y^1, Y^2, Y^3$ and $Y^4$ is $CR^4$ if none of $X^3, X^4, X^5$ and $X^6$ is $CR^4$.

In another embodiment of the invention one of $Y^1, Y^2, Y^3$ and $Y^4$ is $C-CF_3$ if none of $X^3, X^4, X^5$ and $X^6$ is $CR^4$.

In a preferred embodiment of the invention, either one of $X^3, X^4, X^5$ and $X^6$ is $CR^4$ and none of $Y^1, Y^2, Y^3$ and $Y^4$ is $CR^4$, or one of $Y^1, Y^2, Y^3$ and $Y^4$ is $CR^4$ and none of $X^3, X^4, X^5$ and $X^6$ is $CR^4$. In other words, either the condensed ring system (with $X^1$-$X^6$ as ring members) carries one group $R^4$ or the ring with $Y^1$-$Y^4$ as ring members carries one group $R^4$.

In an alternatively preferred embodiment of the invention, one of $Y^1, Y^2, Y^3$ and $Y^4$ is $C-CF_3$ and none of $X^3, X^4, X^5$ and $X^6$ is $CR^4$.

If the condensed ring system (with $X^1$-$X^6$ as ring members) carries one group $R^4$, this is preferably bound in the position of $X^4$ or $X^5$.

If the ring with $Y^1$-$Y^4$ as ring members carries one group $R^4$, this is preferably bound in the position of $Y^4$.

$R^4$ is preferably selected from a C-bound saturated or partially unsaturated monocyclic 4-, 5- or 6-membered heterocyclic ring containing 1 or 2 or 3 heteroatoms selected from O, N, S and SO, as ring members, where the heterocyclic ring optionally carries 1, 2 or 3 substituents $R^8$.

More preferably, $R^4$ is selected from C-bound oxetanyl, thietanyl, azetidinyl, tetrahydrofuranyl, tetrahydrothienyl, tetrahydrothienyl-1-oxide, pyrrolidinyl, pyrrolinyl, pyrazolidinyl, pyrazolinyl, imidazolidinyl, imidazolinyl, tetrahydropyranyl, dihydropyranyl, piperidinyl, tetrahydropyridinyl, dihydropyridinyl, piperazinyl and morpholinyl, where the heterocyclic ring optionally carries 1, 2 or 3 substituents $R^8$.

Preferably, these cyclic structures have the following formulae:

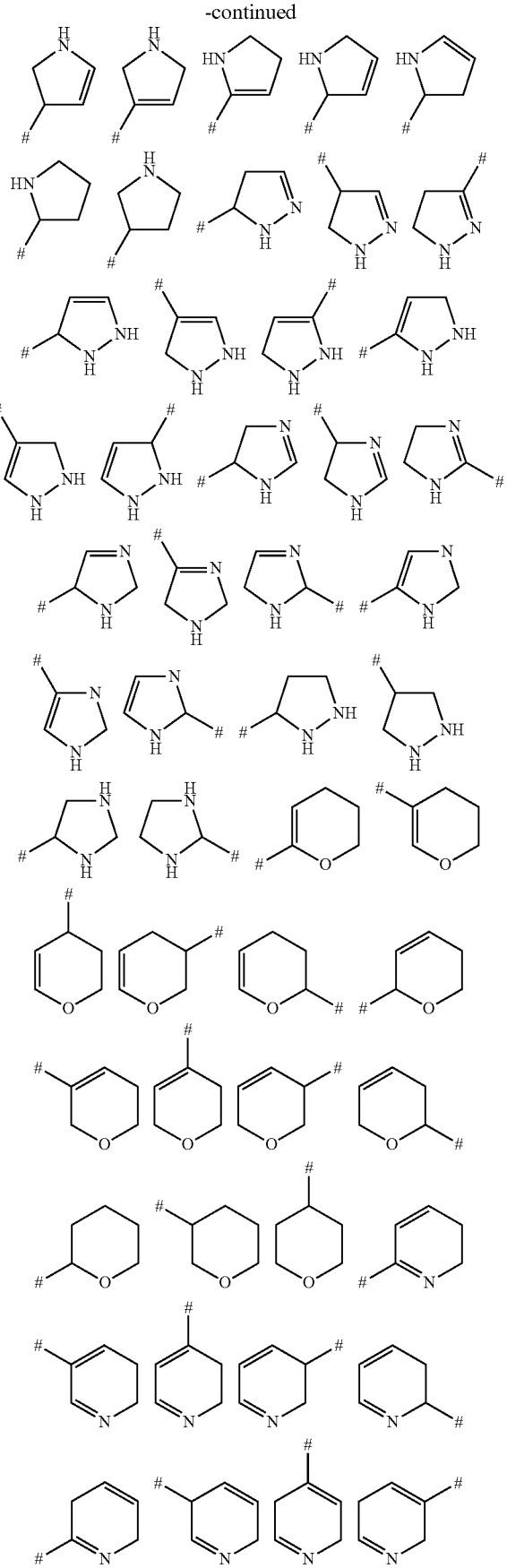

-continued

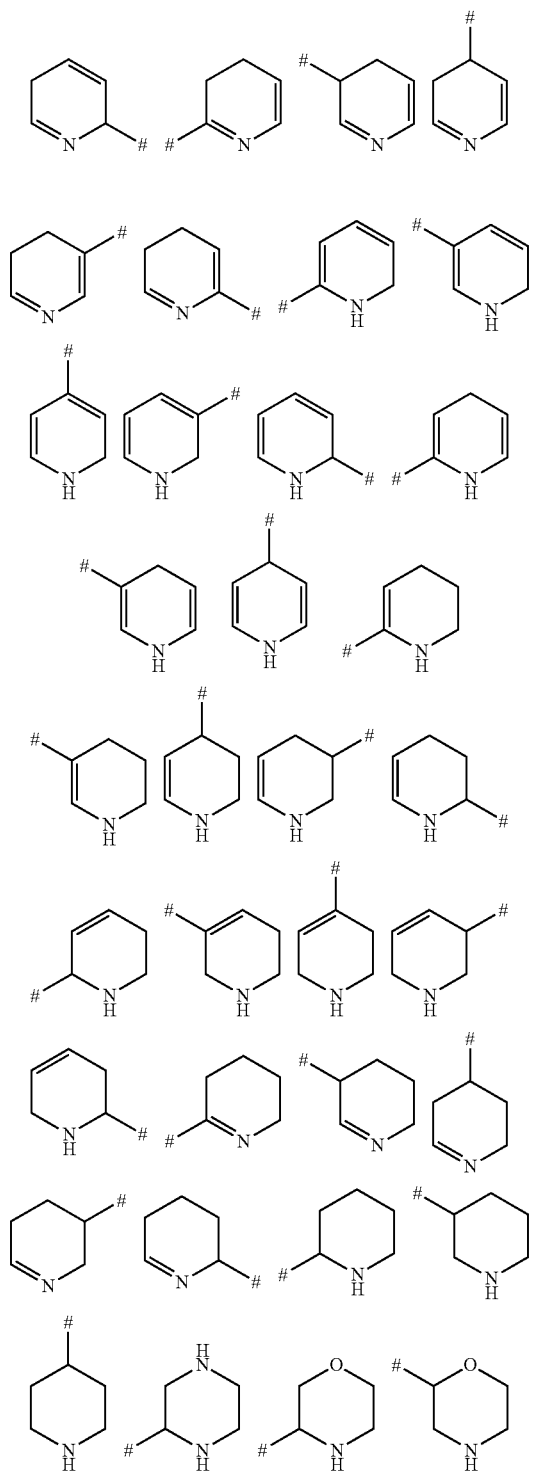

where the above cyclic structures optionally carry 1, 2 or 3 substituents $R^8$, where $R^8$ may be bound to a carbon ring atom or to a nitrogen ring atom, and where # is the attachment point to the remainder of the molecule.

Among the above partially saturated rings preference is given to those having one or more C=C bonds and where one carbon atom of such a C=C double bond forms the attachment point to the remainder of the molecule.

Thus, even more preferably $R^4$ is selected from the following structures

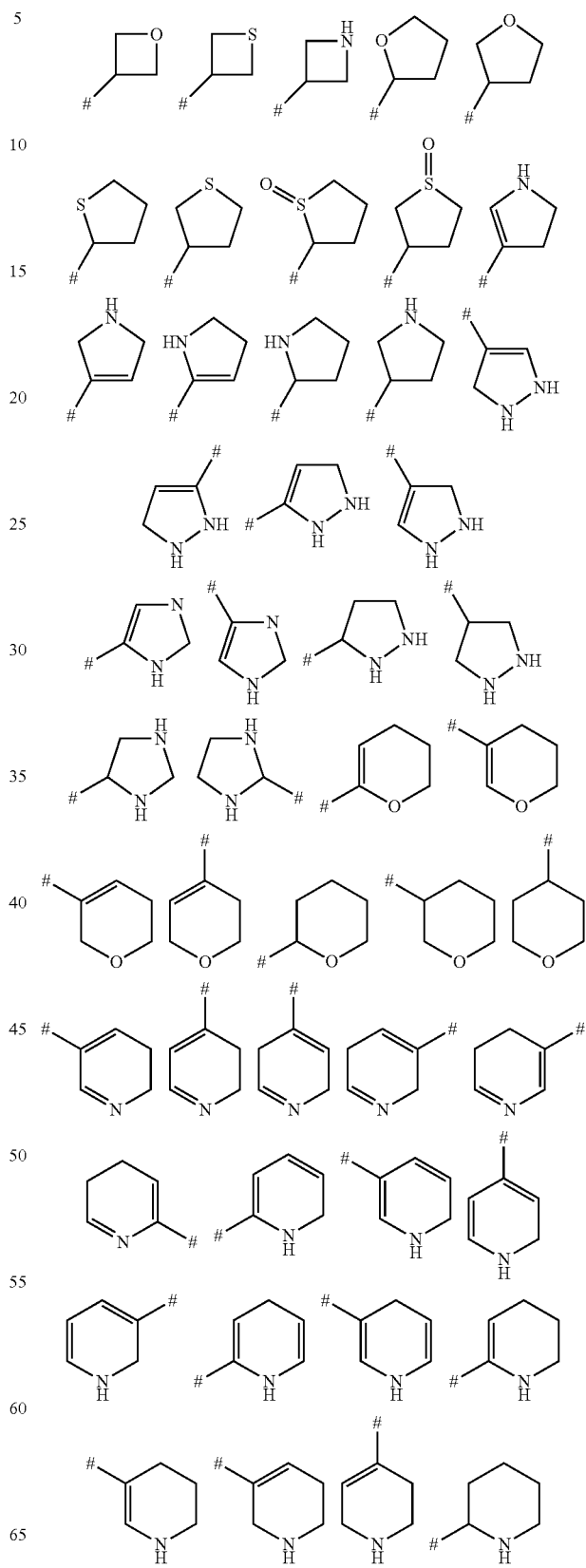

-continued

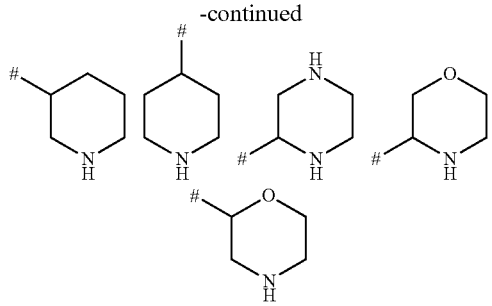

where the above cyclic structures optionally carry 1, 2 or 3 substituents $R^8$, where $R^8$ may be bound to a carbon ring atom or to a nitrogen ring atom, and where # is the attachment point to the remainder of the molecule.

Particularly preferably, $R^4$ is selected from azetidin-3-yl, tetrahydrofuran-3-yl, pyrrolidin-3-yl, pyrrolin-3-yl, tetrahydropyran-4-yl, tetrahydropyran-3-yl, dihydropyran-4-yl, dihydropyran-3-yl, piperidin-4-yl, 1,2,5,6-tetrahydropyridin-4-yl and 1,2-dihydropyridin-4-yl, where the heterocyclic ring optionally carries 1, 2 or 3 substituents $R^8$.

Preferably, these cyclic structures have the following formulae:

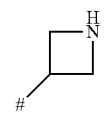  a

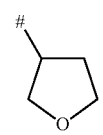  b

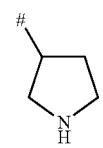  c

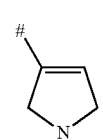  d

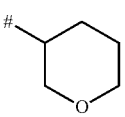  e

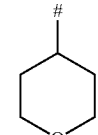  f

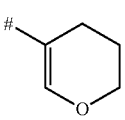  g

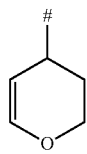  h

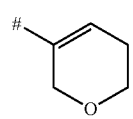  i

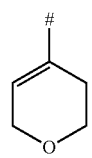  j

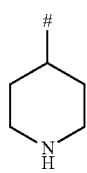  k

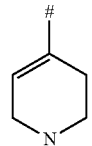  l

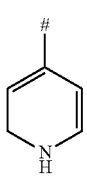  m where the above cyclic structures optionally carry 1, 2 or 3 substituents $R^8$, where $R^8$ may be bound to a carbon ring atom or to a nitrogen ring atom, and where # is the attachment point to the remainder of the molecule.

Among these, more preference is given to structures c, d, e, f, g, j, k and l.

$R^8$ is preferably selected from $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl and benzyl and is more preferably $C_1$-$C_6$-alkyl, $C_1$-$C_6$-haloalkyl or $C_1$-$C_6$-alkoxycarbonyl. Even more preferably, $R^8$ is $C_1$-$C_4$-alkyl, $C_1$-$C_4$-haloalkyl, especially fluorinated $C_1$-$C_4$-alkyl, or tert-butoxycarbonyl, and is in particular $C_1$-$C_2$-alkyl, $C_1$-$C_2$-haloalkyl, especially fluorinated $C_1$-$C_2$-alkyl, or tert-butoxycarbonyl.

Preferably, $R^8$ is N-bound; i.e. it is bound to a nitrogen ring atom.

Specifically, $R^4$ is selected from following structures:

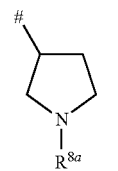
c.1

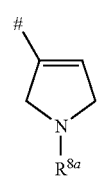
d.1

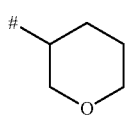
e.1

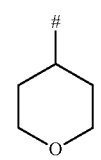
f.1

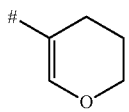
g.1

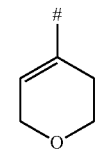
j.1

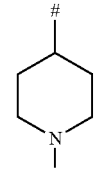
k.1

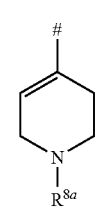
l.1 where $R^{8a}$ is hydrogen or has one of the general or, in particular, one of the preferred meanings given above for $R^8$; and # is the attachment point to the remainder of the molecule.

Preferably, at most one of $X^1$, $X^2$, $X^3$, $X^4$, $X^5$ and $X^6$ is N. If one of $X^1$, $X^2$, $X^3$, $X^4$, $X^5$ and $X^6$ is N, this is preferably $X^3$ or $X^4$ and more preferably $X^3$.

In one particular embodiment, none of $X^1$, $X^2$, $X^3$, $X^4$, $X^5$ and $X^6$ is N. In other words, more preferably $X^1$ and $X^2$ are $CR^2$ and $X^3$, $X^4$, $X^5$ and $X^6$ are $CR^3$ or $CR^4$.

In another particular embodiment, $X^1$ and $X^2$ are $CR^2$, $X^3$ is N and $X^4$, $X^5$ and $X^6$ are $CR^3$ or $CR^4$.

If one of $Y^1$, $Y^2$, $Y^3$ and $Y^4$ is N, this is preferably $Y^2$. In other words, preferably $Y^1$, $Y^2$, $Y^3$ and $Y^4$ are $CR^4$ or $CR^5$, or $Y^2$ is N and $Y^1$, $Y^3$ and $Y^4$ are $CR^4$ or $CR^5$, of course with the proviso that at most one of $Y^1$, $Y^2$, $Y^3$ and $Y^4$ is $CR^4$.

A is preferably $NR^B$. $R^B$ is preferably hydrogen or $C_1$-$C_4$-alkyl, more preferably hydrogen or methyl and specifically hydrogen. Thus, A is specifically NH.

$R^1$ is preferably hydrogen or $C_1$-$C_4$-alkyl, more preferably hydrogen or methyl and in particular hydrogen.

$R^2$ is preferably hydrogen.

$R^3$ is preferably selected from hydrogen, CN, halogen (preferably F or Cl, more preferably F), $C_1$-$C_6$-alkyl, $C_1$-$C_6$-haloalkyl, $C_3$-$C_7$-cycloalkyl, $C_3$-$C_7$-halocycloalkyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl and $C_1$-$C_6$-haloalkoxycarbonyl, more preferably from hydrogen, CN, F, Cl, $C_1$-$C_6$-alkyl, $C_1$-$C_6$-haloalkyl, $C_1$-$C_6$-alkoxy and $C_1$-$C_6$-haloalkoxy and is in particular selected from hydrogen, CN, F, $C_1$-$C_6$-alkyl, $C_1$-$C_6$-haloalkyl, $C_1$-$C_6$-alkoxy and $C_1$-$C_6$-haloalkoxy, specifically hydrogen, F, $C_1$-$C_2$-alkyl, $C_1$-$C_2$-haloalkyl, $C_1$-$C_2$-alkoxy and $C_1$-$C_2$-haloalkoxy.

Preferably, 0, 1 or 2 of the radicals $R^3$ is different from hydrogen.

Specifically, $R^3$ is hydrogen if one or two of $X^3$, $X^4$, $X^5$ and $X^6$ are $CR^4$.

In particular, at most two of the radicals $R^3$ are different from hydrogen, if none of $X^3$, $X^4$, $X^5$ and $X^6$ are $CR^4$, in particular if also none of $Y^1$, $Y^2$, $Y^3$ and $Y^4$ is $CR^4$, provided, of course, that in this particular case one of $Y^1$, $Y^2$, $Y^3$ and $Y^4$ is C—$CF_3$.

$R^5$ is preferably selected from hydrogen, CN, halogen (preferably F or Cl, more preferably F), $C_1$-$C_6$-alkyl, $C_1$-$C_6$-haloalkyl, $C_3$-$C_7$-cycloalkyl, $C_3$-$C_7$-halocycloalkyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl and $C_1$-$C_6$-haloalkoxycarbonyl, more preferably from hydrogen, halogen, $C_1$-$C_4$-haloalkyl, $C_3$-$C_7$-cycloalkyl and $C_3$-$C_7$-halocycloalkyl, even more preferably from hydrogen, F, Cl, $C_1$-$C_4$-haloalkyl, $C_3$-$C_7$-cycloalkyl and $C_3$-$C_7$-halocycloalkyl, in particular from hydrogen, F, $C_1$-$C_4$-haloalkyl, $C_3$-$C_7$-cycloalkyl and $C_3$-$C_7$-halocycloalkyl and specifically from hydrogen, fluorinated $C_1$-$C_2$-alkyl and $C_3$-$C_6$-cycloalkyl.

Preferably, at most one of the radicals $R^5$ is different from hydrogen.

If none of $X^3$, $X^4$, $X^5$ and $X^6$ are $CR^4$ and if also none of $Y^1$, $Y^2$, $Y^3$ and $Y^4$ is $CR^4$, one of $Y^1$, $Y^2$, $Y^3$ and $Y^4$ is C—$CF_3$. In this particular embodiment, $Y^4$ is preferably C—$CF_3$. Likewise, it is preferred that in this particular embodiment $X^1$ is $CR^2$, $X^2$ is $CR^2$, $X^3$, $X^4$, $X^5$ and $X^6$ are $CR^3$ while $Y^1$, $Y^2$, $Y^4$ and $Y^4$ are independently of each other are selected from $CR^5$ and N, where $R^2$, $R^3$ and $R^5$ are as defined herein, provided that at most one and in particular none of $Y^1$, $Y^2$, $Y^4$ and $Y^4$ is N and one of $Y^1$, $Y^2$, $Y^4$ and $Y^4$ is C—$CF_3$, preferably with $Y^4$ being C—$CF_3$. In this particular embodiment, preferably 0, 1 or 2 radicals $R^3$ are different from hydrogen. In this particular case, $R^2$ is preferably hydrogen.

In a particularly preferred embodiment of the invention the compounds of formula I are compounds of formula I-1

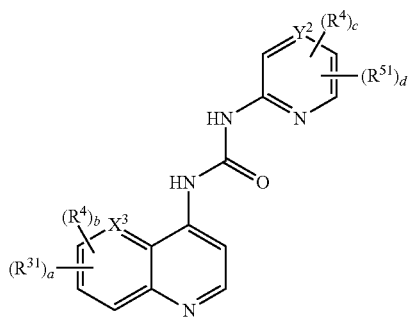

(I-1)

where
X³ is N or CH;
Y² is N or CH;
R³¹ has one of the general or, in particular, one of the preferred meanings given above for R³ except for hydrogen, and is preferably halogen, $C_1$-$C_4$-alkyl or $C_1$-$C_4$-alkoxy and more preferably F, $C_1$-$C_4$-alkyl or $C_1$-$C_4$-alkoxy;
R⁴ has one of the general or, in particular, one of the preferred meanings given above;
R⁵¹ has one of the general or, in particular, one of the preferred meanings given above for R⁵ except for hydrogen; and
a is 0, 1 or 2; and
b, c and d are independently of each other 0 or 1, with the proviso that one of b and c is 1.
Preferably, a is 0 if b is 1.

In another particularly preferred embodiment of the invention the compounds of formula I are compounds of formula I-2

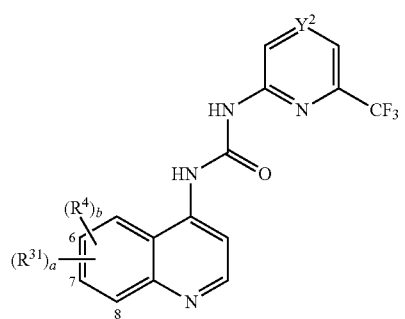

(I-2)

where
Y² is N or in particular CH;
R³¹ if present, has one of the meanings given for R³ except for hydrogen and has preferably one of the preferred meanings;
R⁴ if present, has one of the meanings given herein;
a is 0, 1 or 2;
b is 0 or 1, in particular 0.

Amongst the compounds of formula I-2, a particular embodiment relates to those compounds, where Y² is CH.

Amongst the compounds of formula I-2, a particular embodiment relates to those compounds, where R³¹, if present, is selected from the group consisting of halogen, trifluoromethyl, cyano and methoxy.

If n is 1 or 2, R³¹ is in particular located in the 6-, 7- or 8-position of formula I-2.

Amongst the compounds of formula I-2, a particular embodiment relates to those compounds, where b is 0. However, if b is 1, R⁴ is preferably located in the 7-position as indicated.

Suitable compounds I are those of formulae I.a to I.1, the stereoisomers, N-oxides, prodrugs, tautomers and/or physiologically tolerated acid addition salts thereof, wherein Y² is N or CH, R⁴ has the above-defined general or preferred meanings, R³ᵃ, R³ᵇ, R³ᶜ and R³ᵈ are hydrogen or have one of the above-defined general or preferred meanings given for R³ and R⁵ᵃ and R⁵ᵇ are hydrogen or have one of the above-defined general or preferred meanings given for R⁵. Particularly preferred meanings of R³ᵃ, R³ᵇ, R³ᶜ, R³ᵈ, R⁴, R⁵ᵃ, R⁵ᵇ and Y² specifically in compounds of formulae I.a to I.1 are as defined below.

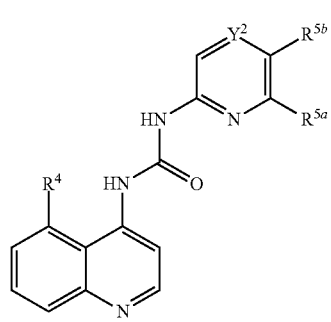

I.a

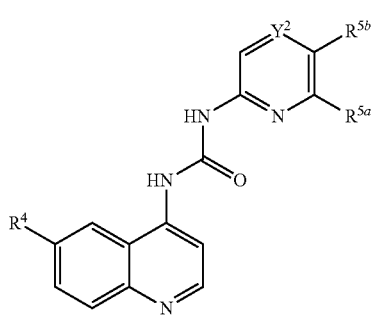

I.b

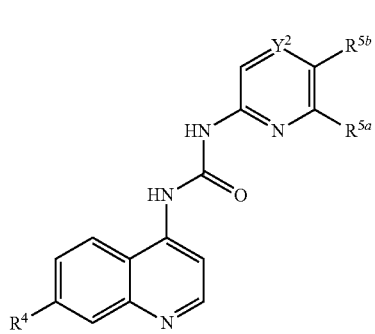

I.c

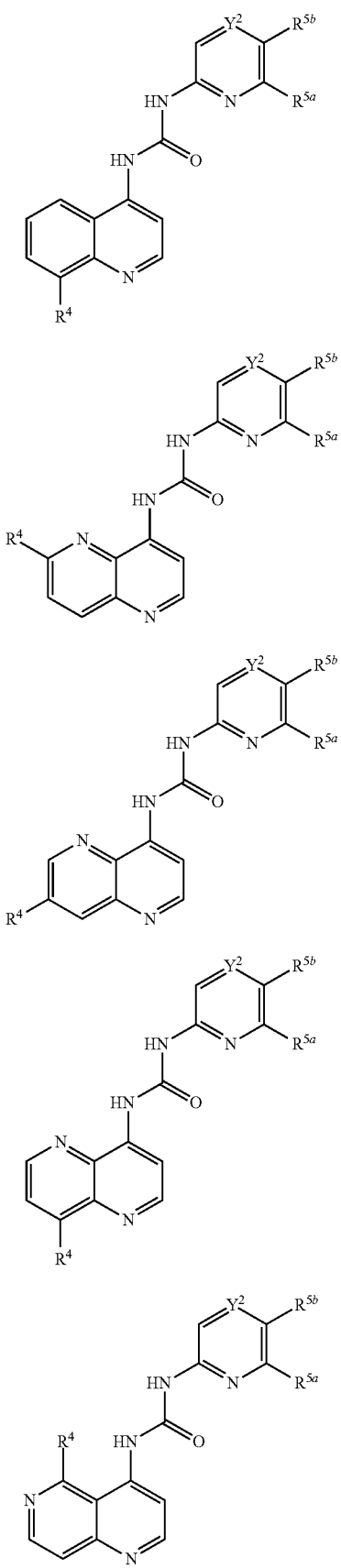
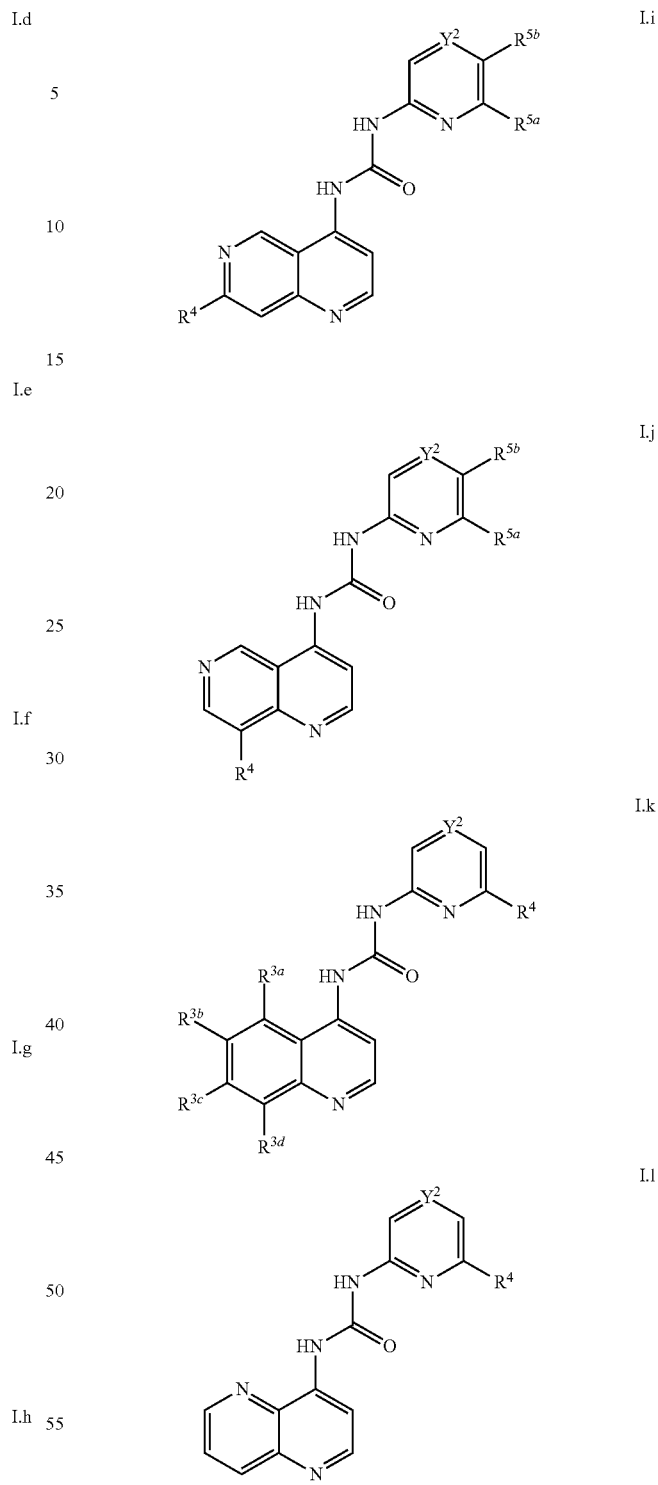

Examples of preferred compounds which are represented by the formulae I.a to I.l are the individual compounds compiled in the tables 1 to 418 below, where the variable $R^4$ has the meanings given in one row of Table A. Moreover, the meanings mentioned for the individual variables in the tables are per se, independently of the combination in which they are mentioned, a particularly preferred embodiment of the substituents in question.

Table 1
Compounds of the formula I.a in which $Y^2$ is CH, $R^{5a}$ and $R^{5b}$ are H and $R^4$ for a compound corresponds in each case to one row of Table A.
Table 2
Compounds of the formula I.a in which $Y^2$ is CH, $R^{5a}$ is F, $R^{5b}$ is H and $R^4$ for a compound corresponds in each case to one row of Table A.
Table 3
Compounds of the formula I.a in which $Y^2$ is CH, $R^{5a}$ is Cl, $R^{5b}$ is H and $R^4$ for a compound corresponds in each case to one row of Table A.
Table 4
Compounds of the formula I.a in which $Y^2$ is CH, $R^{5a}$ is Br, $R^{5b}$ is H and $R^4$ for a compound corresponds in each case to one row of Table A.
Table 5
Compounds of the formula I.a in which $Y^2$ is CH, $R^{5a}$ is $CH_3$, $R^{5b}$ is H and $R^4$ for a compound corresponds in each case to one row of Table A.
Table 6
Compounds of the formula I.a in which $Y^2$ is CH, $R^{5a}$ is $CF_3$, $R^{5b}$ is H and $R^4$ for a compound corresponds in each case to one row of Table A.
Table 7
Compounds of the formula I.a in which $Y^2$ is CH, $R^{5a}$ is $OCH_3$, $R^{5b}$ is H and $R^4$ for a compound corresponds in each case to one row of Table A.
Table 8
Compounds of the formula I.a in which $Y^2$ is CH, $R^{5a}$ is $OCF_3$, $R^{5b}$ is H and $R^4$ for a compound corresponds in each case to one row of Table A.
Table 9
Compounds of the formula I.a in which $Y^2$ is CH, $R^{5a}$ is cyclopropyl, $R^{5b}$ is H and $R^4$ for a compound corresponds in each case to one row of Table A.
Table 10
Compounds of the formula I.a in which $Y^2$ is CH, $R^{5a}$ is H, $R^{5b}$ is F and $R^4$ for a compound corresponds in each case to one row of Table A.
Table 11
Compounds of the formula I.a in which $Y^2$ is CH, $R^{5a}$ is H, $R^{5b}$ is Cl and $R^4$ for a compound corresponds in each case to one row of Table A.
Table 12
Compounds of the formula I.a in which $Y^2$ is CH, $R^{5a}$ is H, $R^{5b}$ is Br and $R^4$ for a compound corresponds in each case to one row of Table A.
Table 13
Compounds of the formula I.a in which $Y^2$ is CH, $R^{5a}$ is H, $R^{5b}$ is $CH_3$ and $R^4$ for a compound corresponds in each case to one row of Table A.
Table 14
Compounds of the formula I.a in which $Y^2$ is CH, $R^{5a}$ is H, $R^{5b}$ is $CF_3$ and $R^4$ for a compound corresponds in each case to one row of Table A.
Table 15
Compounds of the formula I.a in which $Y^2$ is CH, $R^{5a}$ is H, $R^{5b}$ is $OCH_3$ and $R^4$ for a compound corresponds in each case to one row of Table A.
Table 16
Compounds of the formula I.a in which $Y^2$ is CH, $R^{5a}$ is H, $R^{5b}$ is $OCF_3$ and $R^4$ for a compound corresponds in each case to one row of Table A.
Table 17
Compounds of the formula I.a in which $Y^2$ is CH, $R^{5a}$ is H, $R^{5b}$ is cyclopropyl and $R^4$ for a compound corresponds in each case to one row of Table A.
Table 18
Compounds of the formula I.a in which $Y^2$ is N, $R^{5a}$ and $R^{5b}$ are H and $R^4$ for a compound corresponds in each case to one row of Table A.
Table 19
Compounds of the formula I.a in which $Y^2$ is N, $R^{5a}$ is F, $R^{5b}$ is H and $R^4$ for a compound corresponds in each case to one row of Table A.
Table 20
Compounds of the formula I.a in which $Y^2$ is N, $R^{5a}$ is Cl, $R^{5b}$ is H and $R^4$ for a compound corresponds in each case to one row of Table A.
Table 21
Compounds of the formula I.a in which $Y^2$ is N, $R^{5a}$ is Br, $R^{5b}$ is H and $R^4$ for a compound corresponds in each case to one row of Table A.
Table 22
Compounds of the formula I.a in which $Y^2$ is N, $R^{5a}$ is $CH_3$, $R^{5b}$ is H and $R^4$ for a compound corresponds in each case to one row of Table A.
Table 23
Compounds of the formula I.a in which $Y^2$ is N, $R^{5a}$ is $CF_3$, $R^{5b}$ is H and $R^4$ for a compound corresponds in each case to one row of Table A.
Table 24
Compounds of the formula I.a in which $Y^2$ is N, $R^{5a}$ is $OCH_3$, $R^{5b}$ is H and $R^4$ for a compound corresponds in each case to one row of Table A.
Table 25
Compounds of the formula I.a in which $Y^2$ is N, $R^{5a}$ is $OCF_3$, $R^{5b}$ is H and $R^4$ for a compound corresponds in each case to one row of Table A.
Table 26
Compounds of the formula I.a in which $Y^2$ is N, $R^{5a}$ is cyclopropyl, $R^{5b}$ is H and $R^4$ for a compound corresponds in each case to one row of Table A.
Table 27
Compounds of the formula I.a in which $Y^2$ is N, $R^{5a}$ is H, $R^{5b}$ is F and $R^4$ for a compound corresponds in each case to one row of Table A.
Table 28
Compounds of the formula I.a in which $Y^2$ is N, $R^{5a}$ is H, $R^{5b}$ is Cl and $R^4$ for a compound corresponds in each case to one row of Table A.
Table 29
Compounds of the formula I.a in which $Y^2$ is N, $R^{5a}$ is H, $R^{5b}$ is Br and $R^4$ for a compound corresponds in each case to one row of Table A.
Table 30
Compounds of the formula I.a in which $Y^2$ is N, $R^{5a}$ is H, $R^{5b}$ is $CH_3$ and $R^4$ for a compound corresponds in each case to one row of Table A.
Table 31
Compounds of the formula I.a in which $Y^2$ is N, $R^{5a}$ is H, $R^{5b}$ is $CF_3$ and $R^4$ for a compound corresponds in each case to one row of Table A.
Table 32
Compounds of the formula I.a in which $Y^2$ is N, $R^{5a}$ is H, $R^{5b}$ is $OCH_3$ and $R^4$ for a compound corresponds in each case to one row of Table A.

Table 33
Compounds of the formula I.a in which $Y^2$ is N, $R^{5a}$ is H, $R^{5b}$ is $OCF_3$ and $R^4$ for a compound corresponds in each case to one row of Table A.

Table 34
Compounds of the formula I.a in which $Y^2$ is N, $R^{5a}$ is H, $R^{5b}$ is cyclopropyl and $R^4$ for a compound corresponds in each case to one row of Table A.

Tables 35 to 68
Compounds of the formula I.b in which the combination of $Y^2$, $R^{5a}$ and $R^{5b}$ is as defined in tables 1 to 34 and $R^4$ for a compound corresponds in each case to one row of Table A.

Tables 69 to 102
Compounds of the formula I.c in which the combination of $Y^2$, $R^{5a}$ and $R^{5b}$ is as defined in tables 1 to 34 and $R^4$ for a compound corresponds in each case to one row of Table A.

Tables 103 to 136
Compounds of the formula I.d in which the combination of $Y^2$, $R^{5a}$ and $R^{5b}$ is as defined in tables 1 to 34 and $R^4$ for a compound corresponds in each case to one row of Table A.

Tables 137 to 170
Compounds of the formula I.e in which the combination of $Y^2$, $R^{5a}$ and $R^{5b}$ is as defined in tables 1 to 34 and $R^4$ for a compound corresponds in each case to one row of Table A.

Tables 171 to 204
Compounds of the formula I.f in which the combination of $Y^2$, $R^{5a}$ and $R^{5b}$ is as defined in tables 1 to 34 and $R^4$ for a compound corresponds in each case to one row of Table A.

Tables 205 to 238
Compounds of the formula I.g in which the combination of $Y^2$, $R^{5a}$ and $R^{5b}$ is as defined in tables 1 to 34 and $R^4$ for a compound corresponds in each case to one row of Table A.

Tables 239 to 272
Compounds of the formula I.h in which the combination of $Y^2$, $R^{5a}$ and $R^{5b}$ is as defined in tables 1 to 34 and $R^4$ for a compound corresponds in each case to one row of Table A.

Tables 273 to 306
Compounds of the formula I.i in which the combination of $Y^2$, $R^{5a}$ and $R^{5b}$ is as defined in tables 1 to 34 and $R^4$ for a compound corresponds in each case to one row of Table A.

Tables 307 to 340
Compounds of the formula I.j in which the combination of $Y^2$, $R^{5a}$ and $R^{5b}$ is as defined in tables 1 to 34 and $R^4$ for a compound corresponds in each case to one row of Table A.

Table 341
Compounds of the formula I.k in which $Y^2$ is CH, $R^{3a}$, $R^{3b}$, $R^{3c}$ and $R^{3d}$ are H and $R^4$ for a compound corresponds in each case to one row of Table A.

Table 342
Compounds of the formula I.k in which $Y^2$ is CH, $R^{3a}$ is F, $R^{3b}$, $R^{3c}$ and $R^{3d}$ are H and $R^4$ for a compound corresponds in each case to one row of Table A.

Table 343
Compounds of the formula I.k in which $Y^2$ is CH, $R^{3a}$ is Cl, $R^{3b}$, $R^{3c}$ and $R^{3d}$ are H and $R^4$ for a compound corresponds in each case to one row of Table A.

Table 344
Compounds of the formula I.k in which $Y^2$ is CH, $R^{3a}$ is Br, $R^{3b}$, $R^{3c}$ and $R^{3d}$ are H and $R^4$ for a compound corresponds in each case to one row of Table A.

Table 345
Compounds of the formula I.k in which $Y^2$ is CH, $R^{3a}$ is $CH_3$, $R^{3b}$, $R^{3c}$ and $R^{3d}$ are H and $R^4$ for a compound corresponds in each case to one row of Table A.

Table 346
Compounds of the formula I.k in which $Y^2$ is CH, $R^{3a}$ is $CF_3$, $R^{3b}$, $R^{3c}$ and $R^{3d}$ are H and $R^4$ for a compound corresponds in each case to one row of Table A.

Table 347
Compounds of the formula I.k in which $Y^2$ is CH, $R^{3a}$ is $OCH_3$, $R^{3b}$, $R^{3c}$ and $R^{3d}$ are H and $R^4$ for a compound corresponds in each case to one row of Table A.

Table 348
Compounds of the formula I.k in which $Y^2$ is CH, $R^{3a}$ is $OCF_3$, $R^{3b}$, $R^{3c}$ and $R^{3d}$ are H and $R^4$ for a compound corresponds in each case to one row of Table A.

Table 349
Compounds of the formula I.k in which $Y^2$ is CH, $R^{3a}$ is cyclopropyl, $R^{3b}$, $R^{3c}$ and $R^{3d}$ are H and $R^4$ for a compound corresponds in each case to one row of Table A.

Table 350
Compounds of the formula I.k in which $Y^2$ is CH, $R^{3b}$ is F, $R^{3a}$, $R^{3c}$ and $R^{3d}$ are H and $R^4$ for a compound corresponds in each case to one row of Table A.

Table 351
Compounds of the formula I.k in which $Y^2$ is CH, $R^{3b}$ is Cl, $R^{3a}$, $R^{3c}$ and $R^{3d}$ are H and $R^4$ for a compound corresponds in each case to one row of Table A.

Table 352
Compounds of the formula I.k in which $Y^2$ is CH, $R^{3b}$ is Br, $R^{3a}$, $R^{3c}$ and $R^{3d}$ are H and $R^4$ for a compound corresponds in each case to one row of Table A.

Table 353
Compounds of the formula I.k in which $Y^2$ is CH, $R^{3b}$ is $CH_3$, $R^{3a}$, $R^{3c}$ and $R^{3d}$ are H and $R^4$ for a compound corresponds in each case to one row of Table A.

Table 354
Compounds of the formula I.k in which $Y^2$ is CH, $R^{3b}$ is $CF_3$, $R^{3a}$, $R^{3c}$ and $R^{3d}$ are H and $R^4$ for a compound corresponds in each case to one row of Table A.

Table 355
Compounds of the formula I.k in which $Y^2$ is CH, $R^{3b}$ is $OCH_3$, $R^{3a}$, $R^{3c}$ and $R^{3d}$ are H and $R^4$ for a compound corresponds in each case to one row of Table A.

Table 356
Compounds of the formula I.k in which $Y^2$ is CH, $R^{3b}$ is $OCF_3$, $R^{3a}$, $R^{3c}$ and $R^{3d}$ are H and $R^4$ for a compound corresponds in each case to one row of Table A.

Table 357
Compounds of the formula I.k in which $Y^2$ is CH, $R^{3b}$ is cyclopropyl, $R^{3a}$, $R^{3c}$ and $R^{3d}$ are H and $R^4$ for a compound corresponds in each case to one row of Table A.

Table 358
Compounds of the formula I.k in which $Y^2$ is CH, $R^{3c}$ is F, $R^{3a}$, $R^{3b}$ and $R^{3d}$ are H and $R^4$ for a compound corresponds in each case to one row of Table A.

Table 359
Compounds of the formula I.k in which $Y^2$ is CH, $R^{3c}$ is Cl, $R^{3a}$, $R^{3b}$ and $R^{3d}$ are H and $R^4$ for a compound corresponds in each case to one row of Table A.

Table 360
Compounds of the formula I.k in which $Y^2$ is CH, $R^{3c}$ is Br, $R^{3a}$, $R^{3b}$ and $R^{3d}$ are H and $R^4$ for a compound corresponds in each case to one row of Table A.

Table 361
Compounds of the formula I.k in which $Y^2$ is CH, $R^{3c}$ is $CH_3$, $R^{3a}$, $R^{3b}$ and $R^{3d}$ are H and $R^4$ for a compound corresponds in each case to one row of Table A.

Table 362
Compounds of the formula I.k in which $Y^2$ is CH, $R^{3c}$ is $CF_3$, $R^{3a}$, $R^{3b}$ and $R^{3d}$ are H and $R^4$ for a compound corresponds in each case to one row of Table A.
Table 363
Compounds of the formula I.k in which $Y^2$ is CH, $R^{3c}$ is $OCH_3$, $R^{3a}$, $R^{3b}$ and $R^{3d}$ are H and $R^4$ for a compound corresponds in each case to one row of Table A.
Table 364
Compounds of the formula I.k in which $Y^2$ is CH, $R^{3c}$ is $OCF_3$, $R^{3a}$, $R^{3b}$ and $R^{3d}$ are H and $R^4$ for a compound corresponds in each case to one row of Table A.
Table 365
Compounds of the formula I.k in which $Y^2$ is CH, $R^{3c}$ is cyclopropyl, $R^{3a}$, $R^{3b}$ and $R^{3d}$ are H and $R^4$ for a compound corresponds in each case to one row of Table A.
Table 366
Compounds of the formula I.k in which $Y^2$ is CH, $R^{3d}$ is F, $R^{3a}$, $R^{3b}$ and $R^{3c}$ are H and $R^4$ for a compound corresponds in each case to one row of Table A.
Table 367
Compounds of the formula I.k in which $Y^2$ is CH, $R^{3d}$ is Cl, $R^{3a}$, $R^{3b}$ and $R^{3c}$ are H and $R^4$ for a compound corresponds in each case to one row of Table A.
Table 368
Compounds of the formula I.k in which $Y^2$ is CH, $R^{3d}$ is Br, $R^{3a}$, $R^{3b}$ and $R^{3c}$ are H and $R^4$ for a compound corresponds in each case to one row of Table A.
Table 369
Compounds of the formula I.k in which $Y^2$ is CH, $R^{3d}$ is $CH_3$, $R^{3a}$, $R^{3b}$ and $R^{3c}$ are H and $R^4$ for a compound corresponds in each case to one row of Table A.
Table 370
Compounds of the formula I.k in which $Y^2$ is CH, $R^{3d}$ is $CF_3$, $R^{3a}$, $R^{3b}$ and $R^{3c}$ are H and $R^4$ for a compound corresponds in each case to one row of Table A.
Table 371
Compounds of the formula I.k in which $Y^2$ is CH, $R^{3d}$ is $OCH_3$, $R^{3a}$, $R^{3b}$ and $R^{3c}$ are H and $R^4$ for a compound corresponds in each case to one row of Table A.
Table 372
Compounds of the formula I.k in which $Y^2$ is CH, $R^{3d}$ is $OCF_3$, $R^{3a}$, $R^{3b}$ and $R^{3c}$ are H and $R^4$ for a compound corresponds in each case to one row of Table A.
Table 373
Compounds of the formula I.k in which $Y^2$ is CH, $R^{3d}$ is cyclopropyl, $R^{3a}$, $R^{3b}$ and $R^{3c}$ are H and $R^4$ for a compound corresponds in each case to one row of Table A.
Table 374
Compounds of the formula I.k in which $Y^2$ is CH, $R^{3b}$ is $CH_3$, $R^{3d}$ is Cl, $R^{3a}$ and $R^{3c}$ are H and $R^4$ for a compound corresponds in each case to one row of Table A.
Table 375
Compounds of the formula I.k in which $Y^2$ is CH, $R^{3b}$ is Cl, $R^{3d}$ is Cl, $R^{3a}$ and $R^{3c}$ are H and $R^4$ for a compound corresponds in each case to one row of Table A.
Table 376
Compounds of the formula I.k in which $Y^2$ is CH, $R^{3b}$ is F, $R^{3d}$ is F, $R^{3a}$ and $R^{3c}$ are H and $R^4$ for a compound corresponds in each case to one row of Table A.
Table 377
Compounds of the formula I.k in which $Y^2$ is CH, $R^{3b}$ is $OCH_3$, $R^{3d}$ is F, $R^{3a}$ and $R^{3c}$ are H and $R^4$ for a compound corresponds in each case to one row of Table A.
Table 378
Compounds of the formula I.k in which $Y^2$ is CH, $R^{3a}$ is F, $R^{3d}$ is F, $R^{3b}$ and $R^{3c}$ are H and $R^4$ for a compound corresponds in each case to one row of Table A.
Tables 379 to 416
Compounds of the formula I.k in which $Y^2$ is N, the combination of $R^{3a}$, $R^{3b}$, $R^{3c}$ and $R^{3d}$ is as defined in tables 341 to 378 and $R^4$ for a compound corresponds in each case to one row of Table A.
Table 417
Compounds of the formula I.l in which $Y^2$ is CH and $R^4$ for a compound corresponds in each case to one row of Table A.
Table 418
Compounds of the formula I.l in which $Y^2$ is N and $R^4$ for a compound corresponds in each case to one row of Table A.

TABLE A

| No. | $R^4$ |
|---|---|
| A-1 | oxetan-3-yl (O in 4-ring) |
| A-2 | azetidin-3-yl (H—N) |
| A-3 | 1-methyl-azetidin-3-yl ($H_3C$—N) |
| A-4 | 1-ethyl-azetidin-3-yl ($CH_3CH_2$—N) |
| A-5 | 1-$CF_3$-azetidin-3-yl ($CF_3$—N) |
| A-6 | 1-(2-fluoroethyl)-azetidin-3-yl ($CH_2FCH_2$—N) |
| A-7 | 1-(2,2-difluoroethyl)-azetidin-3-yl ($CHF_2CH_2$—N) |
| A-8 | 1-(2,2,2-trifluoroethyl)-azetidin-3-yl ($CF_3CH_2$—N) |
| A-9 | tetrahydrofuran-3-yl |
| A-10 | tetrahydrothiophen-3-yl |
| A-11 | 1-oxo-tetrahydrothiophen-3-yl (O=S) |
| A-12 | pyrrolidin-3-yl (HN) |

TABLE A-continued
| No. | R⁴ |
|---|---|
| A-13 | 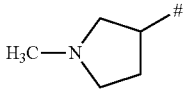 |
| A-14 | 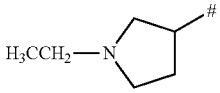 |
| A-15 | 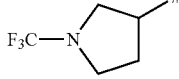 |
| A-16 | 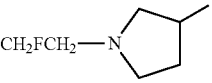 |
| A-17 | 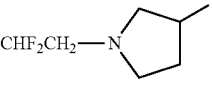 |
| A-18 | 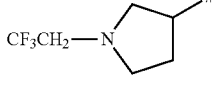 |
| A-19 | 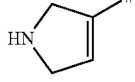 |
| A-20 | 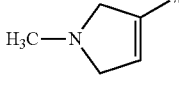 |
| A-21 | 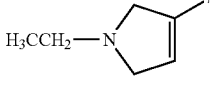 |
| A-22 | 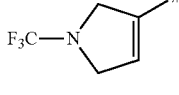 |
| A-23 | 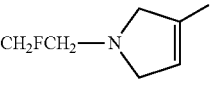 |
| A-24 | 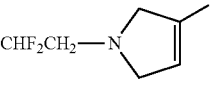 |
| A-25 | 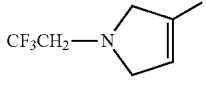 |
| A-26 | 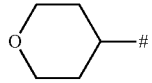 |
| A-27 | 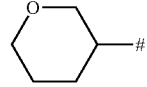 |
| A-28 | 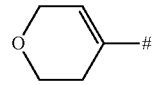 |
| A-29 | 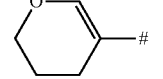 |
| A-30 | 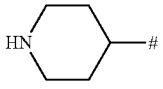 |
| A-31 | 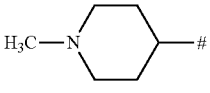 |
| A-32 | 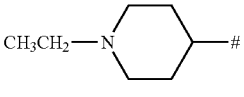 |
| A-33 | 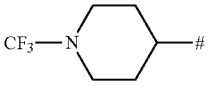 |
| A-34 | 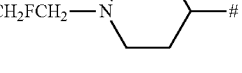 |
| A-35 | 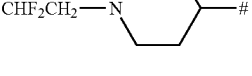 |
| A-36 | 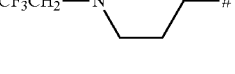 |
| A-37 | 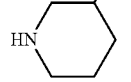 |
| A-38 | 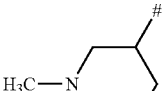 |
| A-39 |  |
| A-40 | 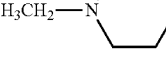 |

TABLE A-continued

| No. | R⁴ |
|---|---|
| A-41 | CH₂FCH₂—N(piperidine)—# (3-position) |
| A-42 | CHF₂CH₂—N(piperidine)—# (3-position) |
| A-43 | CF₃CH₂—N(piperidine)—# (3-position) |
| A-44 | HN(tetrahydropyridine)—# |
| A-45 | H₃C—N(tetrahydropyridine)—# |
| A-46 | CH₃CH₂—N(tetrahydropyridine)—# |
| A-47 | CF₃—N(tetrahydropyridine)—# |
| A-48 | CH₂FCH₂—N(tetrahydropyridine)—# |
| A-49 | CHF₂CH₂—N(tetrahydropyridine)—# |
| A-50 | CF₃CH₂—N(tetrahydropyridine)—# |
| A-51 | HN(morpholine)—# (2-position) |
| A-52 | H₃C—N(morpholine)—# (2-position) |
| A-53 | CH₃CH₂—N(morpholine)—# (2-position) |
| A-54 | CF₃—N(morpholine)—# (2-position) |
| A-55 | CH₂FCH₂—N(morpholine)—# (2-position) |
| A-56 | CHF₂CH₂—N(morpholine)—# (2-position) |
| A-57 | CF₃CH₂—N(morpholine)—# (2-position) |

Among the above compounds, preference is given to compounds of formulae I.b, I.c, I.k and I.l.

Suitable compounds I are also those of formula I.m, the stereoisomers, N-oxides, prodrugs, tautomers and/or physiologically tolerated acid addition salts thereof, wherein $Y^2$ is N or CH, $R^{3a}$, $R^{3b}$ and $R^{3c}$ have one of the above-defined general or preferred meanings given for $R^3$ and are in particular selected from the group consisting of hydrogen, halogen, trifluoromethyl, cyano and methoxy. Particularly preferred meanings of $R^{3a}$, $R^{3b}$ and $R^{3c}$ and $Y^2$ specifically in compounds of formula I.m are as defined in the table below.

I.m

Table 417

Compounds of the formula I.m, in which $Y^2$ is CH and $R^{3a}$, $R^{3b}$ and $R^{3c}$ correspond in each case to one row of Table B.

Table 418

Compounds of the formula I.m, in which $Y^2$ is CH and $R^{3a}$, $R^{3b}$ and $R^{3c}$ correspond in each case to one row of Table B.

TABLE B

| No. | $R^{3a}$ | $R^{3b}$ | $R^{3c}$ |
|---|---|---|---|
| B-1 | H | H | H |
| B-2 | F | H | H |
| B-3 | H | F | H |
| B-4 | H | H | F |
| B-5 | F | F | H |
| B-6 | F | H | F |
| B-7 | H | F | F |
| B-8 | Cl | H | H |
| B-9 | H | Cl | H |
| B-10 | H | H | Cl |
| B-11 | Cl | Cl | H |
| B-12 | Cl | H | Cl |
| B-13 | H | Cl | Cl |
| B-14 | Br | H | H |
| B-15 | H | Br | H |
| B-16 | H | H | Br |
| B-17 | I | H | H |
| B-18 | H | I | H |
| B-19 | H | H | I |
| B-20 | $CF_3$ | H | H |
| B-21 | H | $CF_3$ | H |
| B-22 | H | H | $CF_3$ |
| B-23 | $CF_3$ | $CF_3$ | H |
| B-24 | $CF_3$ | H | $CF_3$ |
| B-25 | H | $CF_3$ | $CF_3$ |
| B-26 | $OCH_3$ | H | H |
| B-27 | H | $OCH_3$ | H |
| B-28 | H | H | $OCH_3$ |
| B-29 | $OCH_3$ | $OCH_3$ | H |
| B-30 | $OCH_3$ | H | $OCH_3$ |
| B-31 | H | $OCH_3$ | $OCH_3$ |
| B-32 | CN | H | H |
| B-33 | H | CN | H |
| B-34 | H | H | CN |
| B-35 | H | H | I |

The compounds of the present invention can be prepared by analogy to routine techniques a skilled person is familiar with. In particular, the compounds of the formula I can be prepared according to the following schemes, wherein the variables, if not stated otherwise, are as defined above and Z indicates a halogen atom, especially Br or I.

Compounds I wherein A is $NR^B$ can be prepared as described in schemes 1 to 4 and 6 to 8.

Scheme 1:

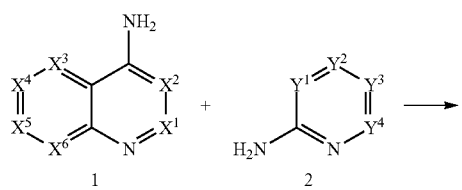

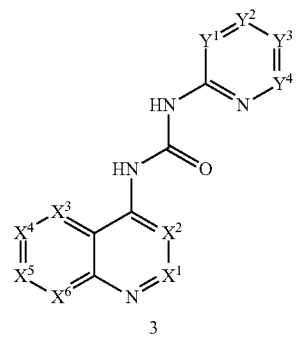

The bicyclic amine 1 can be reacted with amine 2 in the presence of triphosgene (or phosgene or other equivalent reagent), together with a non-alkylating base such as triethylamine. The reaction is carried out in the presence of a suitable solvent such as toluene or N,N-dimethylformamide. The reaction is usually carried out at temperatures of from −30 to 50° C. to give substituted ureas of general formula 3.

Disubstituted urea compounds of the general formula 3 can also be prepared according to a route depicted in scheme 2.

Scheme 2:

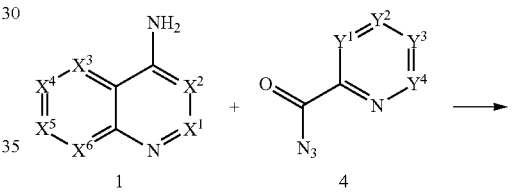

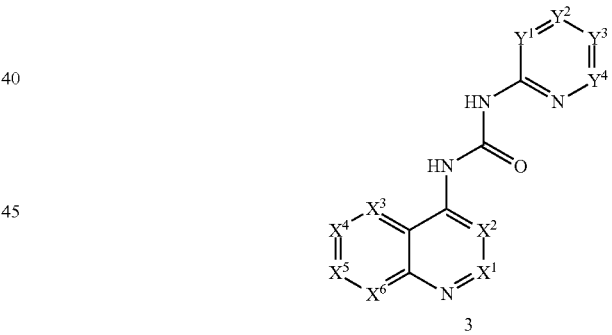

The amine 1 can be acylated by reaction with an acyl azide 4 (prepared by reaction of the corresponding acyl halide with a metal azide salt according to standard methods of organic chemistry) to give disubstituted ureas of general formula 3. The reaction is carried out in the presence of a suitable solvent such as toluene or N,N-dimethylformamide. The reaction is usually carried out at temperatures of from 20-120° C. Other conditions for this transformation (known as the Curtius rearrangement) are described in the following articles: Journal of Organic Chemistry, 1986, 51, 3007 & 5123; Journal of Organic Chemistry, 1987, 52, 4875; Tetrahedron Letters, 1984, 25, 3515; and Organic Reactions, 1947, 3, 337.

Disubstituted urea compounds of the general formula 3 can also be prepared according to a route depicted in scheme 3.

Scheme 3:

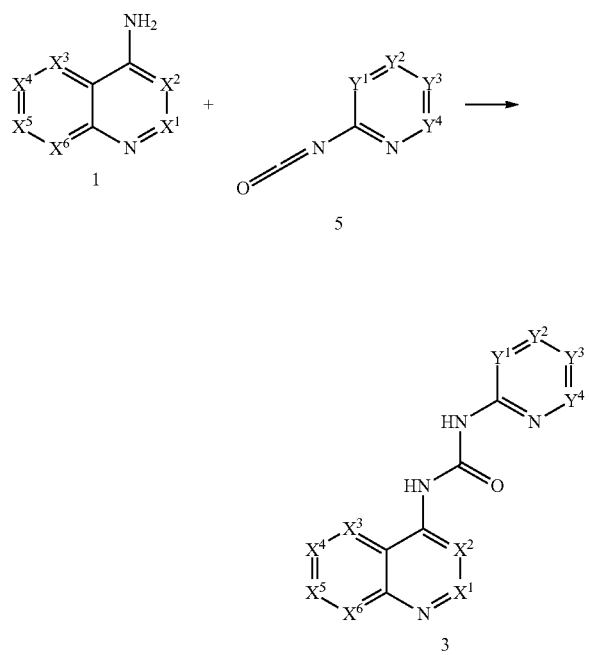

The amine 1 can be acylated by reaction with an isocyanate 5 to give disubstituted ureas of general formula 3. The reaction is carried out in the presence of a suitable solvent such as toluene or N,N-dimethylformamide. The reaction is usually carried out at temperatures of from 20-120° C.

Scheme 4:

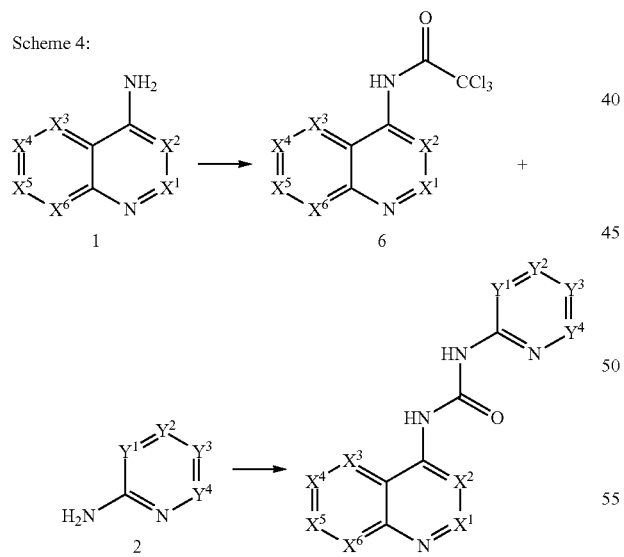

The bicyclic amine 1 can be converted to trichloroacetamide 6 by reaction with trichloroacetyl chloride. The reaction is carried out in the presence of a suitable solvent such as toluene or N,N-dimethylformamide. The reaction is usually carried out at temperatures of from 20-120° C. The trichloroacetamide 6 can be reacted with an amine 2 to give substituted ureas of general formula 3.

Compounds I wherein $R^B$ and/or $R^1$ are different from H can be prepared by N-alkylating compound 3.

Compounds I wherein A is $CH_2$ can be prepared as described in schemes 5 to 8.

Scheme 5:

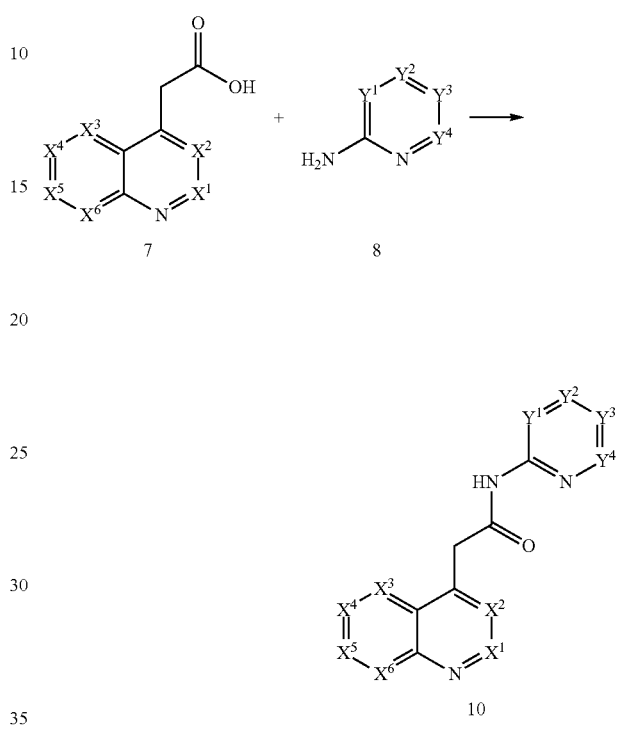

The carboxylic acid 7 can be converted into the amide 10 by reaction with an amine 8 using standard amide formation conditions familiar to those skilled in the art. The reaction is carried out in the presence of a suitable solvent such dimethylacetamide, N,N-dimethylformamide or THF. The reaction is usually carried out at temperatures of from 20 to 120° C. Coupling reagents such as HOBT or carbonyl diimidazole are employed.

Compounds I, wherein A is $CR^{A1}R^{A2}$ can be prepared analogously.

The introduction of the group $R^4$ can be accomplished as shown in the following schemes.

Scheme 6

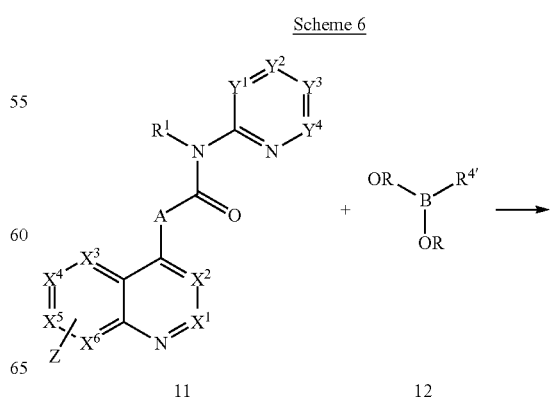

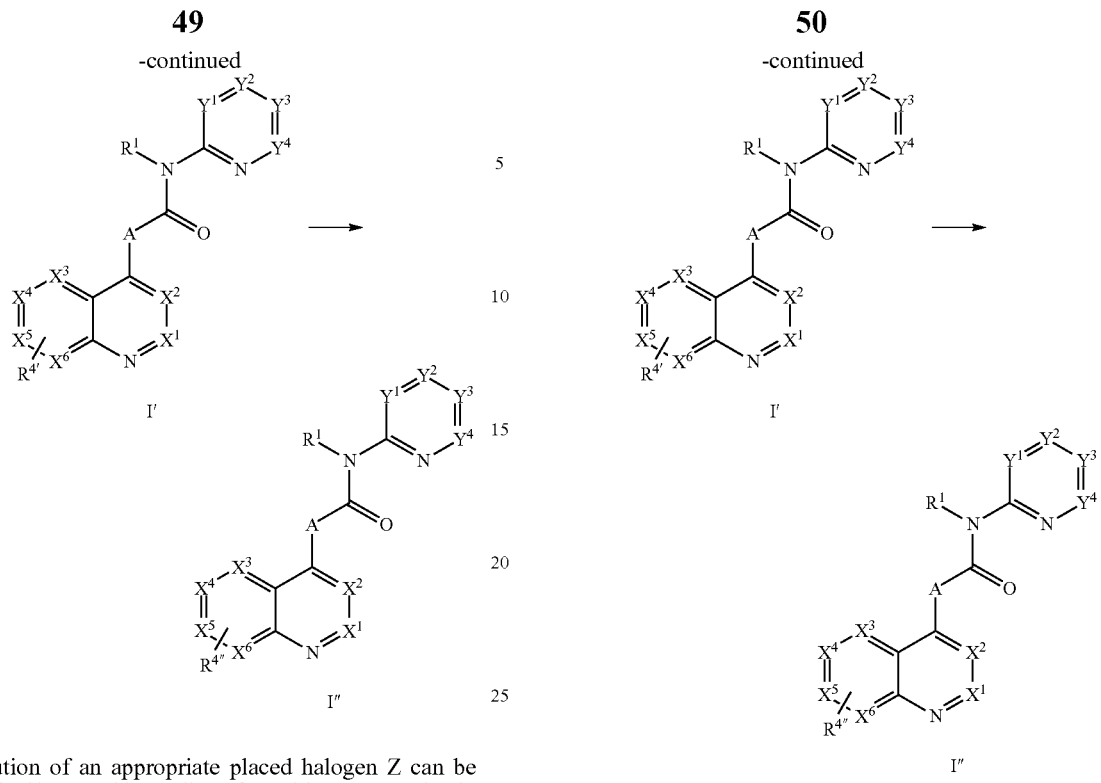

Substitution of an appropriate placed halogen Z can be accomplished by Suzuki coupling of 11 with an appropriately substituted boronic acid (R=H) or ester (R≠H) 12, wherein $R^{4'}$ is a C-bound partially (C=C) unsaturated monocyclic 3-, 4-, 5-, 6- or 7-membered heterocyclic ring containing 1, 2 or 3 heteroatoms or heteroatom-containing groups selected from O, N, S, NO, SO and $SO_2$ as ring members, where the heterocyclic ring optionally carries 1, 2 or 3 C- or N-bound substituents $R^8$, where the ring has the C=C bond in α-position to the attachment point to the boron atom (so that the C=C double bond is a vinylic bond to B) to give substituted products of the general structure I'. The substitution may be conducted via a palladium-mediated coupling using a catalyst such as tetrakis(triphenylphosphine)palladium(0) in the presence of a base (e.g. $Na_2CO_3$) in a solvent such as DMF. The unsaturated compound I' may be reduced to the saturated product I'', wherein $R^{4''}$ is a C-bound saturated monocyclic 3-, 4-, 5-, 6- or 7-membered heterocyclic ring containing 1, 2 or 3 heteroatoms or heteroatom-containing groups selected from O, N, S, NO, SO and $SO_2$ as ring members, where the heterocyclic ring optionally carries 1, 2 or 3 C- or N-bound substituents $R^8$, by reduction of I' in the presence of a catalyst (e.g. Pd on carbon) in the presence of hydrogen.

Scheme 7:

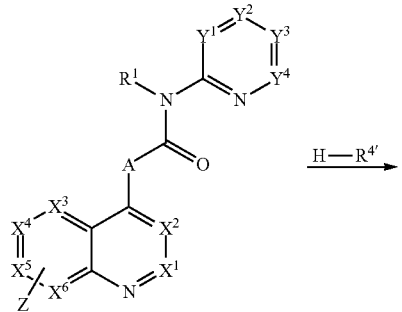

A similar sequence may be accomplished by reaction of 11 in a Heck coupling with a partially unsaturated ring H—$R^{4'}$ to give substituted products of general structure I' which can in turn be reduced to the saturated product I'' as already described.

Starting compound 11 in schemes 6 and 7 can be obtained by using in the reactions of schemes 1 to 5 compounds 1 or 7 yet carrying a halogen atom Z in the desired position.

Scheme 8

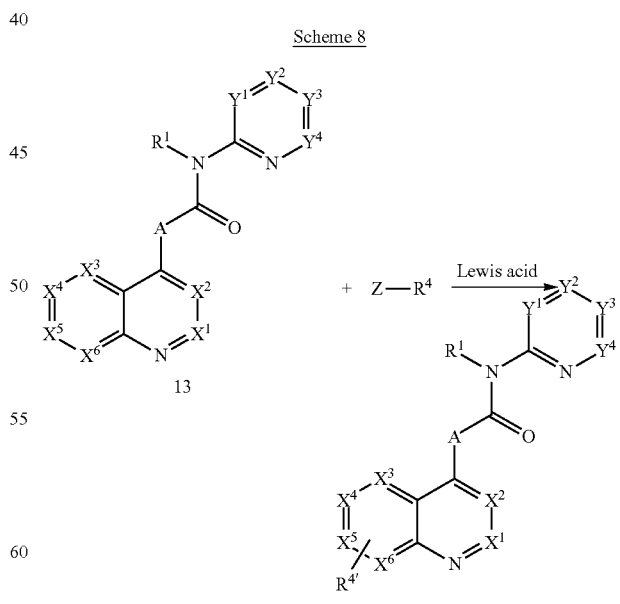

Groups $R^4$ can moreover be introduced in an alkylation reaction, e.g. by reacting the compound 13 under the reaction conditions of a Friedel-Crafts alkylation with a compound Z—R⁴, where Z is a halogen atom, especially Cl or Br. Suitable Lewis acids are for example AlCl₃, FeCl₃, SbCl₅, SnCl₄, BF₃, TiCl₄ and ZnCl₂.

Compounds I where R⁴ is bound to the ring containing Y¹ to Y⁴ as ring members can be prepared in analogy to the reactions shown in schemes 6 to 8 by starting from a compound 14, wherein Z is a halogen atom, especially Br or I.

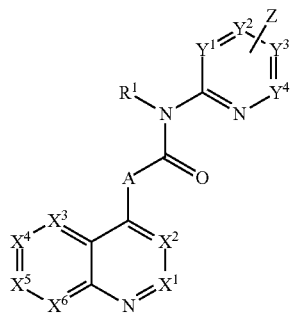

14

Compound 14 can be prepared by using in the reactions of schemes 1 to 5 starting compounds 2, 4, 5 or 8 yet carrying a halogen atom Z in the desired position.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds I are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The present invention moreover relates to compounds of formula I as defined above, wherein at least one of the atoms has been replaced by its stable, non-radioactive isotope (e.g., hydrogen by deuterium, ¹²C by ¹³C, ¹⁴N by ¹⁵N, ¹⁶O by ¹⁸O) and preferably wherein at least one hydrogen atom has been replaced by a deuterium atom.

Of course, the compounds according to the invention contain more of the respective isotope than this naturally occurs and thus is anyway present in the compounds I. Stable isotopes (e.g., deuterium, ¹³C, ¹⁵N, ¹⁸O) are nonradioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

Incorporation of a heavy atom, particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as $pK_a$ and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet. Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammal, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201:

357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising at least one compound of formula I, a stereoisomer, prodrug, tautomer and/or physiologically tolerated acid addition salt thereof and optionally at least one physiologically acceptable carrier and/or auxiliary substance.

The invention also relates to compounds of formula I or the stereoisomers, N-oxides, prodrugs, tautomers or physiologically tolerated acid addition salts thereof for use as a medicament, and to compounds of formula I or the stereoisomers, N-oxides, prodrugs, tautomers or physiologically tolerated acid addition salts thereof for use in the treatment of a medical disorder susceptible to the treatment with a compound that modulates, preferably inhibits, the activity of glycogen synthase kinase 3β.

The invention also relates to the use of the compounds of formula I or of a stereoisomer, prodrug, tautomer or physiologically tolerated acid addition salt thereof for the preparation of a medicament for the treatment of a disorder susceptible to the treatment with a compound that modulates, preferably inhibits, the activity of glycogen synthase kinase 3β.

Furthermore, the invention relates to a method for treating a medical disorder susceptible to treatment with a compound that modulates glycogen synthase kinase 3β activity, said method comprising administering an effective amount of at least one compound of formula I or of a stereoisomer, prodrug, tautomer or physiologically tolerated acid addition salt thereof or of a pharmaceutical composition as defined above to a subject in need thereof.

The compounds of the of formula I according to the present invention, as well as the stereoisomers, the tautomers, the prodrugs and physiologically tolerated acid addition salts thereof, are capable of modulating the activity on glycogen synthase kinase 3β. In particular, the compounds of the of formula I, as well as the stereoisomers, the tautomers, the prodrugs and physiologically tolerated acid addition salts thereof, have an inhibitory activity on glycogen synthase kinase 3β. Amongst the compounds of formula I those are preferred which achieve effective inhibition at low concentrations. In particular, compounds of the formula I are preferred which inhibit glycogen synthase kinase 3β at a level of $IC_{50}<1$ µMol, more preferably at a level of $IC_{50}<0.5$ µMol, particularly preferably at a level of $IC_{50}<0.2$ µMol and most preferably at a level of $IC_{50}<0.1$ µMol.

Therefore the compounds of the of formula I according to the present invention, their stereoisomers, tautomers, their prodrugs and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formula I, a steroisomer, tautomer, prodrug and/or a physiologically tolerated acid addition salt thereof, include in particular neurodegenerative diseases such as Alzheimer's disease. In addition, the compounds of the present invention are also useful for treatment of other neurodegenerative diseases such as behavioural psychiatric symptoms of dementia, Parkinson's disease, tauopathies (e.g. frontotemporoparietal dementia, corticobasal degeneration, Pick's disease, progressive supranuclear palsy, argyophilic brain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma. In addition, the compounds of the present invention are also useful for treatment of schizophrenia. The compounds of the present invention are also useful for treatment of pain.

Diseases which can be treated by supplying the compound of the of formula I, a steroisomer, tautomer, prodrug and/or a physiologically tolerated acid addition salt thereof, include furthermore inflammatory diseases, such as rheumatoid arthritis and osteoarthritis.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formula I involves a method. In this method, an effective quantity of one or more compounds I, a steroisomer, tautomer, prodrug or physiologically tolerable acid addition salt thereof, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to pharmaceutical compositions for treating an individual, preferably a mammal, in particular a human being, productive animal or domestic animal. Thus, the compounds according to the invention are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the pharmaceutical compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

EXAMPLES

The compounds were either characterized via proton-NMR in d$_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Abbreviations:
DCM dichloromethane
DMSO dimethylsulfoxide
DMF dimethylformamide
MeOH methanol
AcOH acetic acid
TFA trifluoroacetic acid
RT room temperature
quant. quantitative I. Preparation Examples Example 1

1-(6-(3,6-Dihydro-2H-pyran-4-yl)pyridin-2-yl)-3-(8-fluoroquinolin-4-yl)urea

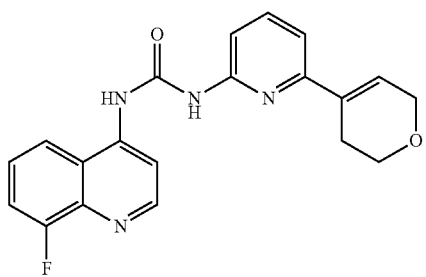 [SMILES: O=C(Nc1cccc(C2=CCOCC2)n1)Nc1ccnc2c(F)cccc12]

1-(8-Fluoroquinolin-4-yl)-3-(6-iodopyridin-2-yl)urea (250 mg, 0.582 mmol), 2-(3,6-dihydro-2H-pyran-4-yl)-4,4,5,5-tetramethyl-1,3,2-dioxaborolane (187 mg, 0.873 mmol), sodium carbonate solution (2M, 1.31 mL, 2.62 mmol) and tetrakis(triphenylphosphine)-palladium(0) (68 mg, 0.058 mmol) were dissolved in 5 ml of DMF under an argon atmosphere and the mixture was stirred at 80° C., in a microwave oven, for one hour. After the solvent had been evaporated down to dryness, the resulting residue was treated with water and the mixture was then extracted with ethyl acetate. After the combined organic phases had been dried over sodium sulfate and the solvent had been filtered and evaporated down to dryness, the resulting residue was purified by column chromatography to give the title product (50 mg, 19%).

$^1$H-NMR (d$_6$-DMSO, 400 MHz) δ 3.32 (m, 5H), 3.95 (s, 2H), 4.21 (s, 2H), 6.65 (s, 1H), 7.19 (m, 1H), 7.60 (m, 4H), 7.78 (m, 1H), 8.01 (m, 1H), 8.32 (s, 1H), 8.80 (m, 1H), 9.98 (s, 1H), 10.70 (s, 1H); MS (APCI+) m/z 365.1 (M+H+, 100%).

Example 2

1-(8-Fluoroquinolin-4-yl)-3-(6-(tetrahydro-2H-pyran-4-yl)pyridin-2-yl)urea

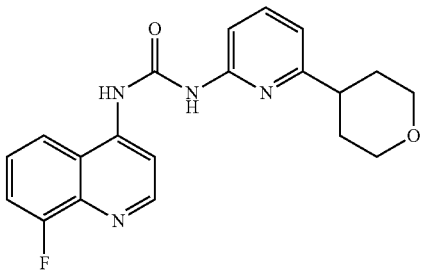

A solution of (1-(6-(3,6-dihydro-2H-pyran-4-yl)pyridin-2-yl)-3-(8-fluoroquinolin-4-yl)urea (21 mg, 0.058 mmol) and 12.3 mg of palladium on charcoal in 20 mL of methanol together with 1 mL of DMF and 1 drop of AcOH was stirred under 1 atm of hydrogen for 18 h. Filtration and evaporation to dryness afforded 21 mg (99%) of the desired title product.

$^1$H-NMR (d$_6$-DMSO, 400 MHz) δ 1.15 (m, 2H), 1.78 (m, 4H), 2.95 (m, 1H), 3.95 (d, 2H), 6.97 (d, 1H), 7.48 (br s, 1H), 7.65 (m, 2H), 7.75 (t, 1H), 8.08 (m, 1H), 8.35 (d, 1H), 9.82 (m, 1H), 10.11 (s, 1H); MS (APCI+) m/z 367.1 (M+H+, 100%).

Example 3

1-(6-(3,4-Dihydro-2H-pyran-5-yl)pyridin-2-yl)-3-(8-fluoroquinolin-4-yl)urea

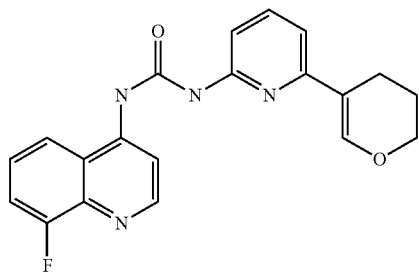 [SMILES: O=C(Nc1cccc(C2=COCCC2)n1)Nc1ccnc2c(F)cccc12]

Prepared by the method described for Example 1. MS (APCI+) m/z 365.1 (M+H+, 100%).

Example 4

1-(6-(3,6-Dihydro-2H-pyran-4-yl)pyridin-2-yl)-3-(7-methoxyquinolin-4-yl)urea

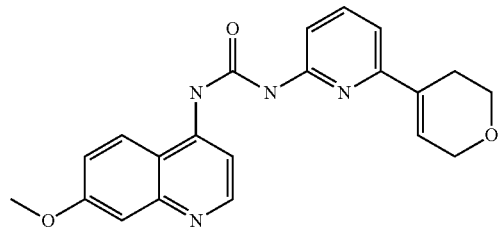 [SMILES: COc1ccc2c(NC(=O)Nc3cccc(C4=CCOCC4)n3)ccnc2c1]

Prepared by the method described for Example 1. MS (APCI+) m/z 377.1 (M+H+, 100%).

Example 5

1-(6-(3,4-Dihydro-2H-pyran-5-yl)quinolin-4-yl)-3-(6-(trifluoromethyl)pyridin-2-yl)urea

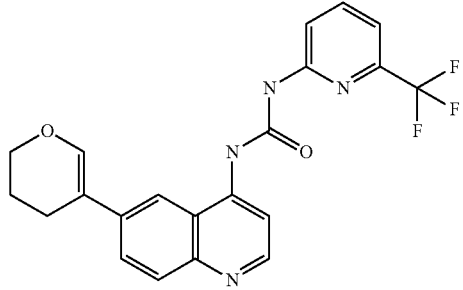 [SMILES: O=C(Nc1cccc(C(F)(F)F)n1)Nc1ccnc2ccc(C3=COCCC3)cc12]

Prepared by the method described for Example 1. MS (APCI+) m/z 415.1 (M+H+, 100%).

Example 6

1-(7-(3,6-Dihydro-2H-pyran-4-yl)quinolin-4-yl)-3-(6-(trifluoromethyl)pyridin-2-yl)urea

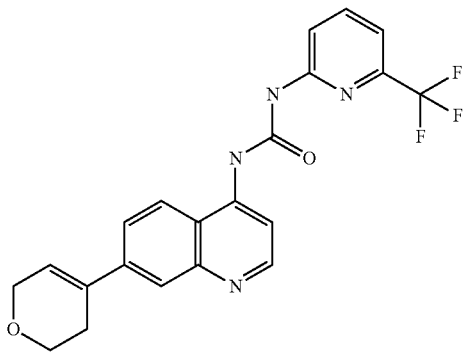 [SMILES: O=C(Nc1cccc(C(F)(F)F)n1)Nc1ccnc2cc(C3=CCOCC3)ccc12]

Prepared by the method described for Example 1.
MS (APCI+) m/z 415.1 (M+H⁺, 100%).

Example 7

1-(6-(Tetrahydro-2H-pyran-4-yl)quinolin-4-yl)-3-(6-(trifluoromethyl)pyridin-2-yl)urea

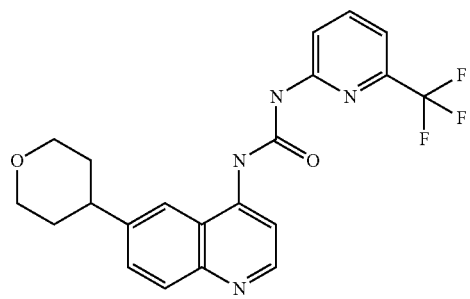

Prepared by the method described for Example 2.
MS (APCI+) m/z 417.1 (M+H⁺, 100%).

Example 8

1-(7-Methoxyquinolin-4-yl)-3-(6-(tetrahydro-2H-pyran-4-yl)pyridin-2-yl)urea

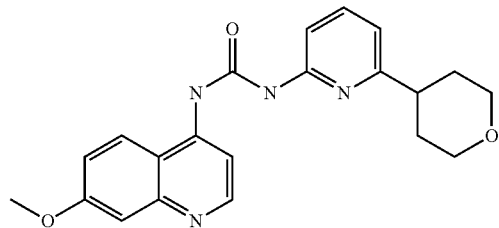 [SMILES: COc1ccc2c(NC(=O)Nc3cccc(C4CCOCC4)n3)ccnc2c1]

Prepared by the method described for Example 2.
MS (APCI+) m/z 379.1 (M+H⁺, 100%).

Example 9

1-(7-(Tetrahydro-2H-pyran-4-yl)quinolin-4-yl)-3-(6-(trifluoromethyl)pyridin-2-yl)urea

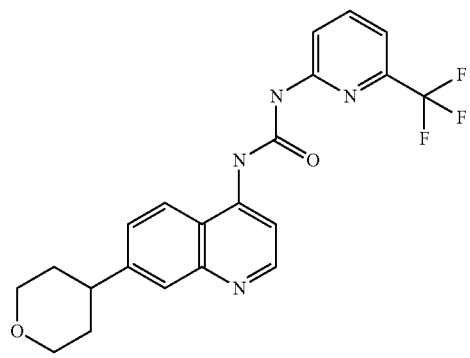 [SMILES: O=C(Nc1cccc(C(F)(F)F)n1)Nc1ccnc2cc(C3CCOCC3)ccc12]

Prepared by the method described for Example 2.
MS (APCI+) m/z 417.1 (M+H⁺, 100%).

Example 10

1-(6-(Tetrahydro-2H-pyran-3-yl)quinolin-4-yl)-3-(6-(trifluoromethyl)pyridin-2-yl)urea

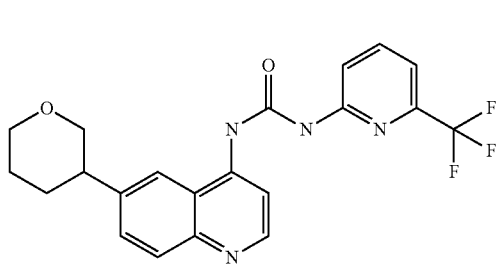 [SMILES: O=C(Nc1cccc(C(F)(F)F)n1)Nc1ccnc2ccc(C3CCCOC3)cc12]

Prepared by the method described for Example 2.
MS (APCI+) m/z 417.1 (M+H⁺, 100%).

Example 11

1-(7-(3,6-Dihydro-2H-pyran-4-yl)quinolin-4-yl)-3-(pyrazin-2-yl)urea

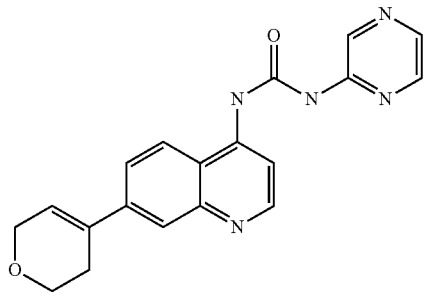 [SMILES: O=C(Nc1cnccn1)Nc1ccnc2cc(C3=CCOCC3)ccc12]

Prepared by the method described for Example 1.
MS (APCI+) m/z 348.1 (M+H⁺, 100%).

Example 12

1-(6-(3,4-Dihydro-2H-pyran-5-yl)pyridin-2-yl)-3-(7-methoxyquinolin-4-yl)urea

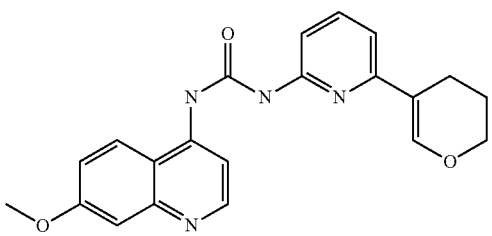 [SMILES: COc1ccc2c(NC(=O)Nc3cccc(C4=COCCC4)n3)ccnc2c1]

Prepared by the method described for Example 1.
MS (APCI+) m/z 377.1 (M+H⁺, 100%).

Example 13

1-(7-Methoxyquinolin-4-yl)-3-(6-(tetrahydro-2H-pyran-3-yl)pyridin-2-yl)urea

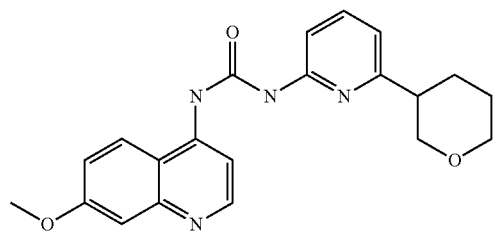 [SMILES: COc1ccc2c(NC(=O)Nc3cccc(C4CCCOC4)n3)ccnc2c1]

Prepared by the method described for Example 2.
MS (APCI+) m/z 379.2 (M+H⁺, 100%).

Example 14

1-(Pyrazin-2-yl)-3-(7-(tetrahydro-2H-pyran-4-yl)quinolin-4-yl)urea

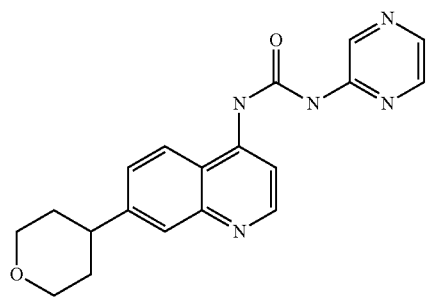 [SMILES: O=C(Nc1cnccn1)Nc1ccnc2cc(C3CCOCC3)ccc12]

Prepared by the method described for Example 2.
MS (APCI+) m/z 350.2 (M+H⁺, 100%).

Example 15

1-(7-(3,4-Dihydro-2H-pyran-5-yl)quinolin-4-yl)-3-(6-(trifluoromethyl)pyridin-2-yl)urea

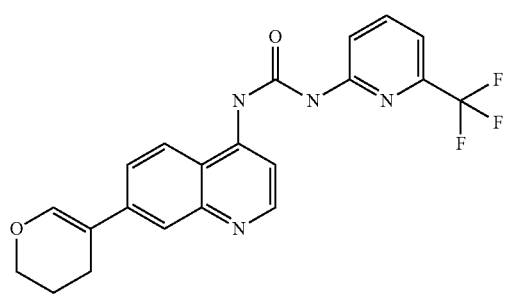 [SMILES: O=C(Nc1cccc(C(F)(F)F)n1)Nc1ccnc2cc(C3=COCCC3)ccc12]

Prepared by the method described for Example 1.
MS (APCI+) m/z 415.1 (M+H⁺, 100%).

Example 16

1-(6-Bromo-quinolin-4-yl)-3-(6-trifluoromethyl-pyridin-2-yl)-urea

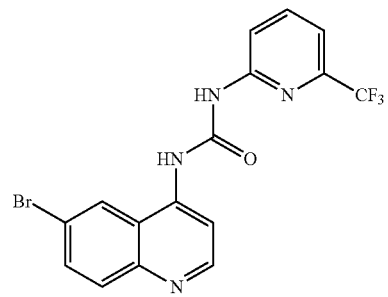 [SMILES: O=C(Nc1cccc(C(F)(F)F)n1)Nc1ccnc2ccc(Br)cc12]

366 mg of bis(trichloromethyl)carbonate (1.234 mmol) were dissolved in 7 ml of dichloromethane (DCM) and cooled to 0° C. To this mixture a solution of 400 mg 6-(trifluoromethyl)pyridin-2-amine (2.467 mmol) and 379 µl triethylamine (5.43 mmol) in 9.7 ml DCM was slowly added over 60 minutes at 0° C. and stirring was then continued for additional 60 minutes at 23° C. 550 mg 6-bromoquinolin-4-amine (2.467 mmol) and 379 µl triethylamine (5.43 mmol) were suspended in 9.7 ml DCM and the suspension was slowly added to the reaction mixture at 23° C., which became a clear solution after 45 minutes. After stirring over night the reaction mixture was poured into ice water and stirred for 2 h. The precipitate formed was filtered off and dried in vacuo for 24 h. 810 mg of the desired product were obtained as off white powder (yield: 80%). The already quite pure raw material was used without further purification.

$^1$H NMR (DMSO-d$^6$, 400 MHz): δ [ppm]: 10.26 (s, 1H), 9.70 (s, 1H), 8.79 (d, 1H), 8.44 (d, 1H), 8.28 (d, 1H), 8.19 (d, 1H), 8.09 (dd, 1H), 7.88 (dd, 1H), 7.93 (d, 1H), 7.57 (d, 1H)
ESI-MS [M+H⁺]: 413.0

Example 17

1-(6-(Trifluoromethyl)pyridin-2-yl)-3-quinolin-4-yl-urea

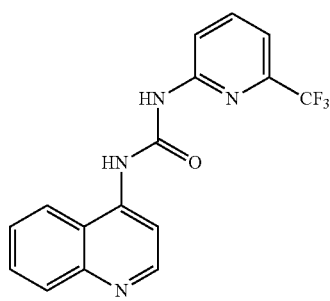 [SMILES: O=C(Nc1cccc(C(F)(F)F)n1)Nc1ccnc2ccccc12]

The title compound was prepared as described in example 16, substituting 6-bromoquinolin-4-amine by quinolin-4-ylamine.
ESI-MS [M+H⁺]: 333.1

Example 18

1-(6,8-Difluoroquinolin-4-yl)-3-(6-trifluoromethyl-pyridin-2-yl)-urea

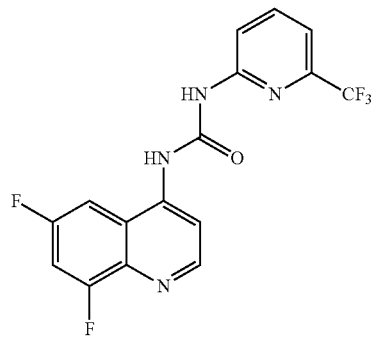 [SMILES: O=C(Nc1cccc(C(F)(F)F)n1)Nc1ccnc2c(F)cc(F)cc12]

The title compound was prepared as described in example 16, substituting 6-bromoquinolin-4-amine by 6,8-difluoro-quinolin-4-ylamine.
ESI-MS [M+H$^+$]: 369.0

Example 19

1-(7-Bromoquinolin-4-yl)-3-(6-trifluoromethyl-pyridin-2-yl)-urea

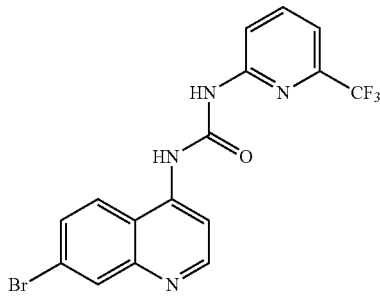 [SMILES: O=C(Nc1cccc(C(F)(F)F)n1)Nc1ccnc2cc(Br)ccc12]

The title compound was prepared as described in example 16, substituting 6-bromoquinolin-4-amine by 7-bromoquinolin-4-amine.
ESI-MS [M+H$^+$]: 410.9/412.9

Example 20

1-(7-Trifluoromethylquinolin-4-yl)-3-(6-trifluoromethyl-pyridin-2-yl)-urea

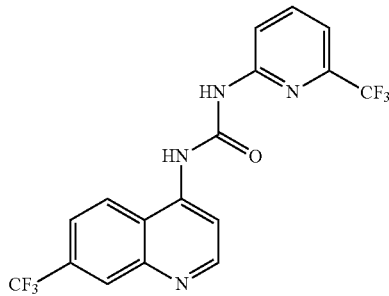 [SMILES: O=C(Nc1cccc(C(F)(F)F)n1)Nc1ccnc2cc(C(F)(F)F)ccc12]

The title compound was prepared as described in example 16, substituting 6-bromoquinolin-4-amine by 7-trifluoromethyl-quinolin-4-ylamine.

ESI-MS [M+H$^+$]: 401.1

Example 21

1-(7-Methoxyquinolin-4-yl)-3-(6-trifluoromethyl-pyridin-2-yl)-urea

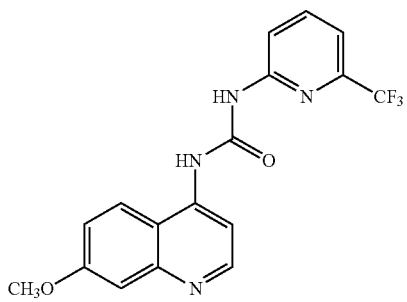

The title compound was prepared as described in example 16, substituting 6-bromoquinolin-4-amine by 7-methoxy-quinolin-4-ylamine.

ESI-MS [M+H$^+$]: 363.1

Example 22

1-(8-Trifluoromethylquinolin-4-yl)-3-(6-trifluoromethyl-pyridin-2-yl)-urea

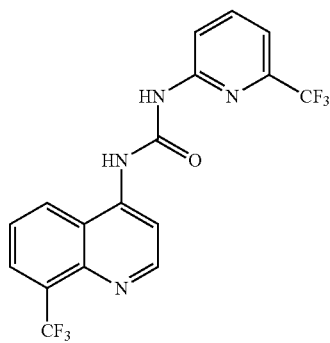 [SMILES: O=C(Nc1cccc(C(F)(F)F)n1)Nc1ccnc2c(C(F)(F)F)cccc12]

The title compound was prepared as described in example 16, substituting 6-bromoquinolin-4-amine by 8-trifluoromethyl-quinolin-4-ylamine.
ESI-MS [M+H$^+$]: 401.1

Example 23

1-(8-Cyanoquinolin-4-yl)-3-(6-trifluoromethyl)pyridin-2-yl)-urea

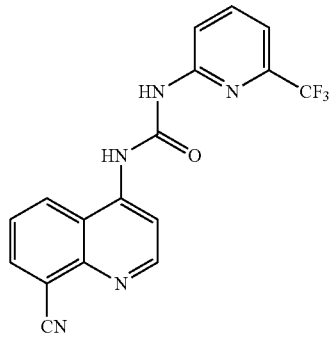 [SMILES: N#Cc1cccc2c(NC(=O)Nc3cccc(C(F)(F)F)n3)ccnc12]

The title compound was prepared as described in example 16, substituting 6-bromoquinolin-4-amine by 8-cyano-quinolin-4-ylamine.
ESI-MS [M+H$^+$]: 358.1

Example 24

1-(8-Iodoquinolin-4-yl)-3-(6-trifluoromethyl-pyridin-2-yl)-urea

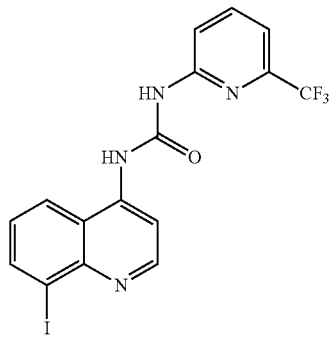 [SMILES: O=C(Nc1cccc(C(F)(F)F)n1)Nc1ccnc2c(I)cccc12]

The title compound was prepared as described in example 16, substituting 6-bromoquinolin-4-amine by 8-iodo-quinolin-4-ylamine.
ESI-MS [M+H$^+$]: 459.0/459.9

Example 25

1-(8-Cyanoquinolin-4-yl)-3-pyrazin-2-yl-urea

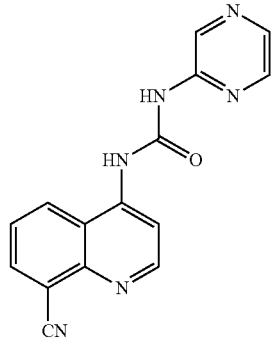 [SMILES: N#Cc1cccc2c(NC(=O)Nc3cnccn3)ccnc12]

The title compound was prepared as described in example 16, substituting 6-bromoquinolin-4-amine by 8-cyano-quinolin-4-ylamine and 6-trifluoromethylpyridine-2-amine by pyrazine-2-ylamine.
ESI-MS [M+H$^+$]: 291.1

Example 26

1-(7-Methoxyquinolin-4-yl)-3-pyrazin-2-yl-urea

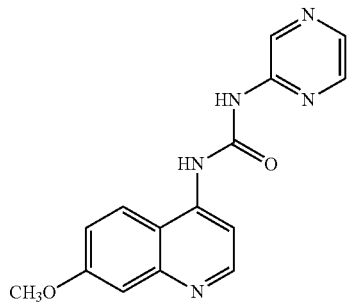

The title compound was prepared as described in example 16, substituting 6-bromoquinolin-4-amine by 7-methoxy-quinolin-4-ylamine and 6-trifluoromethylpyridine-2-amine by pyrazine-2-ylamine.
ESI-MS [M+H$^+$]: 296.1

Example 27 tert-Butyl 4-{4-[3-(6-trifluoromethyl-pyridin-2-yl)-ureido]quinolin-6-yl}-3,6-dihydro-2H-pyridine-1-carboxylate

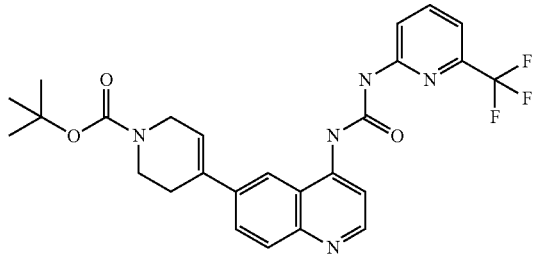 [SMILES: CC(C)(C)OC(=O)N1CC=C(c2ccc3nccc(NC(=O)Nc4cccc(C(F)(F)F)n4)c3c2)CC1]

Step 1: 1-(6-Bromo-quinolin-4-yl)-3-(6-trifluoromethyl-pyridin-2-yl)-urea 366 mg of bis(trichloromethyl)carbonate (1.234 mmol) were dissolved in 7 ml of DCM and cooled to 0° C. To this mixture the solution of 400 mg of 6-(trifluoromethyl)pyridin-2-amine (2.467 mmol) and 379 µl of triethylamine (5.43 mmol) in 9.7 ml DCM was slowly added over 60 minutes at 0° C., and stirring was continued for an additional 60 minutes at room temperature. 550 mg of 6-bromoquinolin-4-amine (2.467 mmol) and 379 µl of triethylamine (5.43 mmol) were suspended in 9.7 ml and subsequently slowly added to the reaction mixture at RT, which became a clear solution after 45 minutes. After stirring over night the reaction mixture was poured into ice water and stirred for 2 h. The precipitation formed was filtered off and dried in vacuum for 24 h. 810 mg of the desired product were obtained as an off white powder (yield: 80%). The quite pure raw material was used without further purification in the next step.

¹H NMR (DMSO-d₆, 400 MHz): δ [ppm]: 10.26 (s, 1H), 9.70 (s, 1H), 8.79 (d, 1H), 8.44 (d, 1H), 8.28 (d, 1H), 8.19 (d, 1H), 8.09 (dd, 1H), 7.88 (dd, 1H), 7.93 (d, 1H), 7.57 (d, 1H)
ESI-MS [M+H⁺]: 413.0

Step 2: tert-Butyl 4-{4-[3-(6-trifluoromethyl-pyridin-2-yl)-ureido]quinolin-6-yl}-3,6-dihydro-2H-pyridine-1-carboxylate 1.500 g of 1-(6-bromo-quinolin-4-yl)-3-(6-trifluoromethyl-pyridin-2-yl)-urea (3.65 mmol), 1.692 g of tert-butyl 4-(4,4,5,5-tetramethyl-1,3,2-dioxaborolan-2-yl)-5,6-dihydropyridine-1(2H)-carboxylate (5.47 mmol), 0.422 g of tetrakis(triphenylphosphine)palladium(0) (0.365 mmol) and 8.21 ml of a 2M sodium carbonate solution (16.42 mmol) were dissolved/suspended in 32 ml DMF in a microwave vessel, flushed with vacuum/argon, and subsequently heated in the microwave for 1 h at 80° C. HPLC/MSD indicated almost complete formation of the desired product. The reaction mixture was poured on ice, stirred for 1 h, and the precipitation formed was filtered off and dried in vacuum for 24 h. 2 g of the desired product were obtained as an off white powder (yield: quant.). The quite pure raw material was used without further purification in the next step.
ESI-MS [M+H⁺]: 514.2

Example 28

1-[6-(1,2,3,6-Tetrahydro-pyridin-4-yl)-quinolin-4-yl]-3-(6-trifluoromethyl-pyridin-2-yl)-urea

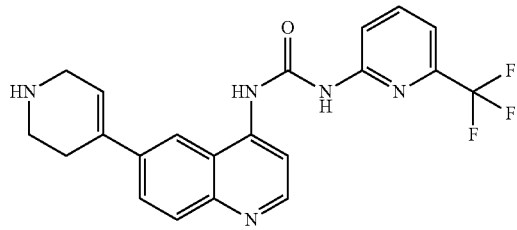 [SMILES: O=C(Nc1cccc(C(F)(F)F)n1)Nc1ccnc2ccc(C3=CCNCC3)cc12]

0.2 g of tert-butyl 4-{4-[3-(6-trifluoromethyl-pyridin-2-yl)-ureido]-quinolin-6-yl}-3,6-dihydro-2H-pyridine-1-carboxylate (0.389 mmol) were dissolved in 0.6 ml DCM (yellow solution). 0.300 ml of TFA (3.89 mmol) were added and the reaction mixture was stirred for 2 h at RT. After evaporation of the solvent and excess TFA in vacuum, water was added to the residue, the acidic mixture extracted with ethyl acetate, the water phase adjusted to pH 9 with 1M NaOH and subsequently extracted three times with DCM. The combined DCM solutions were washed with a small amount of brine, dried over sodium sulphate and the solvent was removed in vacuum. 130 mg of the desired product were obtained as light yellow powder (yield: 81%).

¹H NMR (DMSO-d₆, 500 MHz): δ [ppm]: 10.81 (broad s, 1H), 10.11 (broad s, 1H), 8.67 (d, 1H), 8.28 (d, 1H), 8.23 (s, 1H), 8.20 (d, 1H), 8.06 (dd, 1H), 7.88 and 7.91 (2d, 2H), 7.53 (d, 1H), 6.47 (broad s, 1H), 3.45 (broad s, 2H), 3.3 (very broad s), 3.00 (t, 2H), 2.56 (broad s, 2H)
ESI-MS [M+H⁺]: 414.1

Example 29

1-(6-(Piperidin-4-yl)quinolin-4-yl)-3-(6-(trifluoromethyl)pyridin-2-yl)urea

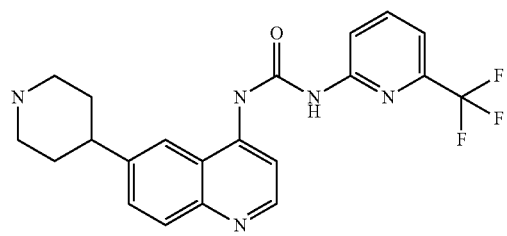 [SMILES: O=C(Nc1cccc(C(F)(F)F)n1)Nc1ccnc2ccc(C3CCNCC3)cc12]

0.59 g of 1-(6-(1,2,3,6-tetrahydropyridin-4-yl)quinolin-4-yl)-3-(6-(trifluoromethyl)pyridin-2-yl)urea (0.427 mmol) were dissolved in a mixture of 143 ml of dioxane and 10 ml of ethanol. After addition of 0.152 g of Pd/C (1.427 mmol) and 0.082 ml of acetic acid (1.427 mmol), hydrogenation was performed for 7 h at 60° C. and over night at room temperature, which led to complete double bond hydrogenation according to HPLC/MSD analysis. The catalyst was filtered off, the solvent removed under reduced pressure and the residue extracted three times with ethyl acetate after adding water and a small amount of NaOH (pH 9). The combined organic phases were washed with a small amount of brine, dried over sodium sulfate and the solvent was removed under reduced pressure. 593 mg of the desired product were obtained as light yellow powder (yield: 64%).

¹H NMR (DMSO-d₆, 500 MHz): δ [ppm]: 10.64 (broad s, 1H), 9.79 (broad s, 1H), 8.70 (d, 1H), 8.21-8.24 (m, 2H), 8.05-8.09 (m, 2H), 7.93 (d, 1H), 7.66 (d, 1H), 7.54 (d, 1H), 3.74 (very broad s), 3.16 (broad d, 2H), 2.82-2.89 (m, 1H), 2.69-2.77 (m, 2H), 1.75-1.89 (m, 4H),
ESI-MS [M+H⁺]: 416.2

Example 30

1-[6-(1-Methyl-1,2,3,6-tetrahydro-pyridin-4-yl)-quinolin-4-yl]-3-(6-trifluoromethyl-pyridin-2-yl)-urea

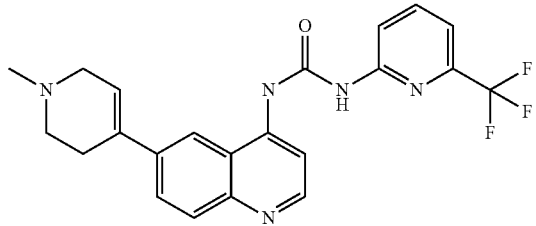 [SMILES: CN1CC=C(c2ccc3nccc(NC(=O)Nc4cccc(C(F)(F)F)n4)c3c2)CC1]

To 0.12 g of 1-[6-(1,2,3,6-tetrahydro-pyridin-4-yl)-quinolin-4-yl]-3-(6-trifluoromethyl-pyridin-2-yl)-urea (0.290 mmol) were added subsequently 2 ml of methanol, 0.366 ml of formaldehyde (4.64 mmol) and a solution of 0.055 g of sodium borohydride (1.451 mmol) in 0.8 ml of water. The reaction was slightly exotherm. A small amount of 2M HCl was added to the reaction mixture up to a pH of 3 to destroy the excess of sodium borohydride. After neutralization with sodium bicarbonate, methanol was evaporated under reduced pressure, water added to the residue, the reaction mixture extracted three times with ethylacetate, the organic phases combined and dried over sodium sulfate and the solvent evaporated under reduced pressure. 120 mg of the desired product were obtained as an off white powder (yield: 97%).

$^1$H NMR (DMSO-d$_6$, 500 MHz): δ [ppm]: 10.45 (broad s, 1H), 9.47 (broad s, 1H), 8.67 (d, 1H), 8.28 (d, 1H), 8.22 (d, 1H), 8.10 (s, 1H), 8.06 (dd, 1H), 7.89 (dd, 2H), 7.53 (d, 1H), 6.39 (broad s, 1H), 3.40 (s, 3H), 3.09 (s, 2H), 2.68 (broad s, 2H), 2.64-2.66 (m, 2H).
ESI-MS [M+H$^+$]: 428.2

Example 31

1-[6-(1-Methyl-piperidin-4-yl)-quinolin-4-yl]-3-(6-trifluoromethyl-pyridin-2-yl)-urea

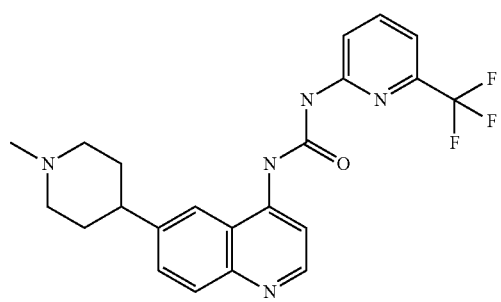 [SMILES: CN1CCC(c2ccc3nccc(NC(=O)Nc4cccc(C(F)(F)F)n4)c3c2)CC1]

The title compound was prepared as described in example 29, substituting 1-(6-(1,2,3,6-tetrahydropyridin-4-yl)quinolin-4-yl)-3-(6-(trifluoromethyl)pyridin-2-yl)urea by 1-[6-(1-Methyl-1,2,3,6-tetrahydro-pyridin-4-yl)-quinolin-4-yl]-3-(6-trifluoromethyl-pyridin-2-yl)-urea.
ESI-MS [M+H$^+$]: 430.1

Example 32

1-{6-[1-(2-Fluoro-ethyl)-piperidin-4-yl]-quinolin-4-yl}-3-(6-trifluoromethyl-pyridin-2-yl)-urea

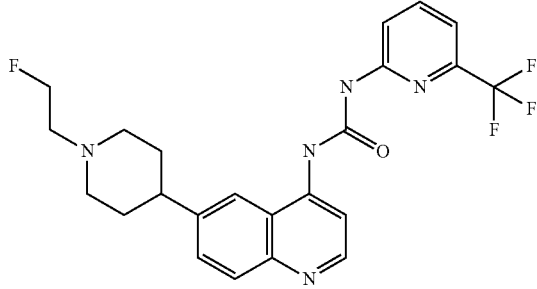 [SMILES: O=C(Nc1cccc(C(F)(F)F)n1)Nc1ccnc2ccc(C3CCN(CCF)CC3)cc12]

The reaction mixture containing 0.27 g of 1-(6-(piperidin-4-yl)quinolin-4-yl)-3-(6-(trifluoromethyl)pyridin-2-yl)urea (0.650 mmol), 0.073 ml of 1-bromo-2-fluoroethane (0.975 mmol), 1.059 g of cesium carbonate (3.25 mmol) and 6.5 of dioxane was shaken in a flask at 60° C. for 4 h. Due to non complete reaction, additional 0.049 ml of 1-bromo-2-fluoroethane (0.650 mmol) were added and the reaction mixture was shaken at 60° C. for 18 h. Saturated sodium bicarbonate solution was added and the mixture extracted three times with ethyl acetate. The combined organic phases were washed once with brine, dried over sodiumsulfat and the solvent removed under reduced pressure. After purifying of the raw material (190 mg) by column chromatography (silica gel, DCM/MeOH 95:5) 90 mg of the desired product were obtained as beige powder (yield: 30%).
ESI-MS [M+H$^+$]: 462.2

Example 33

1-{6-[1-(2,2-Difluoro-ethyl)-piperidin-4-yl]-quinolin-4-yl}-3-(6-trifluoromethyl-pyridin-2-yl)-urea

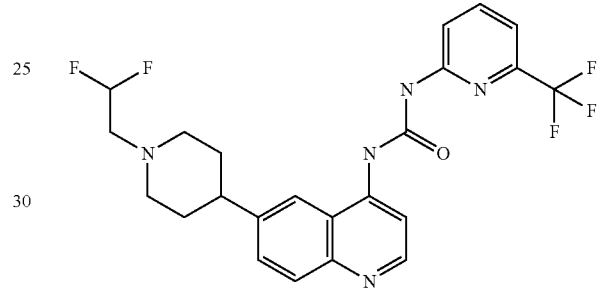

The title compound was prepared as described in example 32, substituting 1-bromo-2-fluoroethane by 1,1-difluoro-2-iodoethane.
ESI-MS [M+H$^+$]: 480.2

Example 34

1-[6-(3,6-Dihydro-2H-pyran-4-yl)-quinolin-4-yl]-3-(6-trifluoromethyl-pyridin-2-yl)-urea

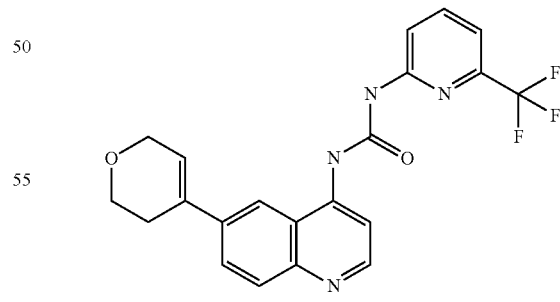

The title compound was prepared as described in example 27 step 2, substituting tert-butyl 4-(4,4,5,5-tetramethyl-1,3,2-dioxaborolan-2-yl)-5,6-dihydropyridine-1(2H)-carboxylate by 2-(3,6-dihydro-2H-pyran-4-yl)-4,4,5,5-tetramethyl-1,3,2-dioxaborolane.
ESI-MS [M+H$^+$]: 415.1

Example 35

1-[6-(3,6-Dihydro-2H-pyran-4-yl)-quinolin-4-yl]-3-pyrazin-2-yl-urea

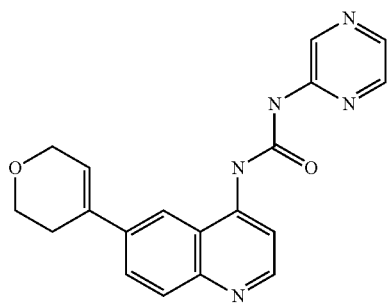 [SMILES: O=C(Nc1cnccn1)Nc1ccnc2ccc(C3=CCOCC3)cc12]

Step 1: 1-(6-Bromoquinolin-4-yl)-3-(pyrazin-2-yl)urea

The title compound was prepared as described in example 27 step 1, substituting 6-(trifluoromethyl)pyridin-2-amine by 6-bromoquinolin-4-amine and 6-bromoquinolin-4-amine by pyrazin-2-amine.

ESI-MS [M+H$^+$]: 345.9

Step 2: 1-[6-(3,6-Dihydro-2H-pyran-4-yl)-quinolin-4-yl]-3-pyrazin-2-yl-urea

The title compound was prepared as described in example 27 step 2, substituting 1-(6-bromo-quinolin-4-yl)-3-(6-trifluoromethyl-pyridin-2-yl)-urea by 1-(6-bromoquinolin-4-yl)-3-(pyrazin-2-yl)urea and tert-butyl 4-(4,4,5,5-tetramethyl-1,3,2-dioxaborolan-2-yl)-5,6-dihydropyridine-1(2H)-carboxylate by 2-(3,6-dihydro-2H-pyran-4-yl)-4,4,5,5-tetramethyl-1,3,2-dioxaborolane.

ESI-MS [M+H$^+$]: 348.1

Example 36 tert-Butyl 4-[4-(3-pyrazin-2-ylureido)quinolin-6-yl]-5,6-dihydropyridine-1(2H)-carboxylate

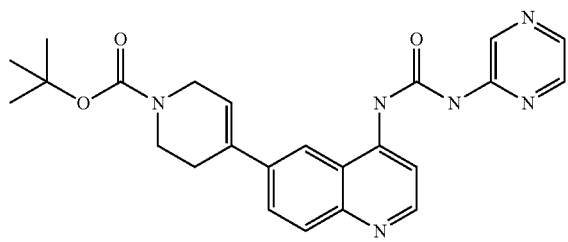 [SMILES: CC(C)(C)OC(=O)N1CC=C(c2ccc3nccc(NC(=O)Nc4cnccn4)c3c2)CC1]

The title compound was prepared as described in example 27 step 2, substituting 1-(6-bromo-quinolin-4-yl)-3-(6-trifluoromethyl-pyridin-2-yl)-urea by 1-(6-bromoquinolin-4-yl)-3-(pyrazin-2-yl)urea (example 35 step 1).

ESI-MS [M+H$^+$]: 447.2

Example 37

1-Pyrazin-2-yl-3-[6-(1,2,3,6-tetrahydro-pyridin-4-yl)-quinolin-4-yl]-urea

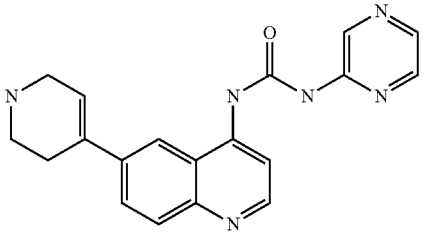 [SMILES: O=C(Nc1cnccn1)Nc1ccnc2ccc(C3=CCNCC3)cc12]

The title compound was prepared as described in example 28, substituting tert-butyl 4-{4-[3-(6-trifluoromethyl-pyridin-2-yl)-ureido]quinolin-6-yl}-3,6-dihydro-2H-pyridine-1-carboxylate by tert-butyl 4-[4-(3-pyrazin-2-ylureido)quinolin-6-yl]-5,6-dihydropyridine-1(2H)-carboxylate (example 36).

ESI-MS [M+H$^+$]: 347.1

Example 38

1-(6-Piperidin-4-yl-quinolin-4-yl)-3-pyrazin-2-yl-urea

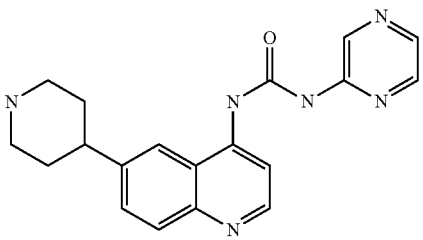 [SMILES: O=C(Nc1cnccn1)Nc1ccnc2ccc(C3CCNCC3)cc12]

The title compound was prepared as described in example 29, substituting 1-(6-(1,2,3,6-tetrahydropyridin-4-yl)quinolin-4-yl)-3-(6-(trifluoromethyl)pyridin-2-yl)urea by 1-pyrazin-2-yl-3-[6-(1,2,3,6-tetrahydro-pyridin-4-yl)-quinolin-4-yl]-urea (example 37).

ESI-MS [M+H$^+$]: 349.2

Example 39

1-{6-[1-(2-Fluoro-ethyl)-piperidin-4-yl]-quinolin-4-yl}-3-pyrazin-2-yl-urea

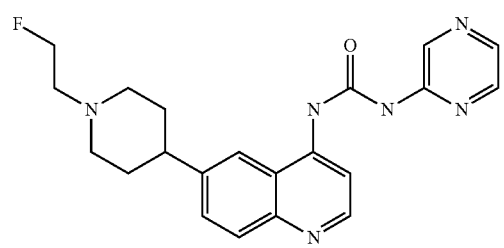 [SMILES: O=C(Nc1cnccn1)Nc1ccnc2ccc(C3CCN(CCF)CC3)cc12]

The title compound was prepared as described in example 32, substituting 1-(6-(piperidin-4-yl)quinolin-4-yl)-3-(6-(trifluoromethyl)pyridin-2-yl)urea by 1-(6-piperidin-4-yl-quinolin-4-yl)-3-pyrazin-2-yl-urea (example 38).

ESI-MS [M+H$^+$]: 395.2

Example 40

1-[6-(1-Methyl-piperidin-4-yl)-quinolin-4-yl]-3-pyrazin-2-yl-urea

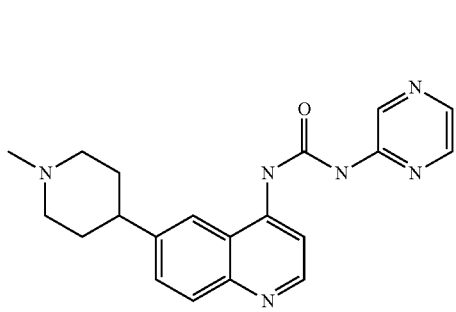 [SMILES: CN1CCC(c2ccc3nccc(NC(=O)Nc4cnccn4)c3c2)CC1]

The title compound was prepared as described in example 30, substituting 1-[6-(1,2,3,6-tetrahydro-pyridin-4-yl)-quinolin-4-yl]-3-(6-trifluoromethyl-pyridin-2-yl)-urea by 1-(6-piperidin-4-yl-quinolin-4-yl)-3-pyrazin-2-yl-urea (example 38).

ESI-MS [M+H$^+$]: 363.2

Example 41 tert-Butyl 4-{4-[3-(6-cyclopropyl-pyrazin-2-yl)-ureido]-quinolin-6-yl}-3,6-dihydro-2H-pyridine-1-carboxylate

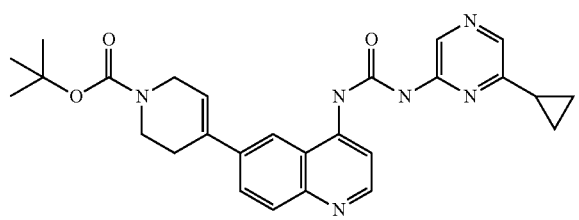 [SMILES: CC(C)(C)OC(=O)N1CC=C(c2ccc3nccc(NC(=O)Nc4cncc(C5CC5)n4)c3c2)CC1]

Step 1: 1-(6-Bromoquinolin-4-yl)-3-(6-cyclopropylpyrazin-2-yl)urea

The title compound was prepared as described in example 27 step 1, substituting 6-(trifluoromethyl)pyridin-2-amine by 6-bromoquinolin-4-amine and 6-bromoquinolin-4-amine by 6-cyclopropylpyrazin-2-amine.

ESI-MS [M+H$^+$]: 386.0

Step 2: Tert-butyl 4-{4-[3-(6-cyclopropyl-pyrazin-2-yl)-ureido]-quinolin-6-yl}-3,6-dihydro-2H-pyridine-1-carboxylate The title compound was prepared as described in example 27 step 2, substituting 1-(6-bromo-quinolin-4-yl)-3-(6-trifluoromethyl-pyridin-2-yl)-urea by 1-(6-bromoquinolin-4-yl)-3-(6-cyclopropylpyrazin-2-yl)urea (example 15 step 1).

ESI-MS [M+H$^+$]: 487.2

Example 42 tert-Butyl 4-{4-[3-(6-cyclopropyl-pyrazin-2-yl)-ureido]-quinolin-6-yl}-piperidine-1-carboxylate

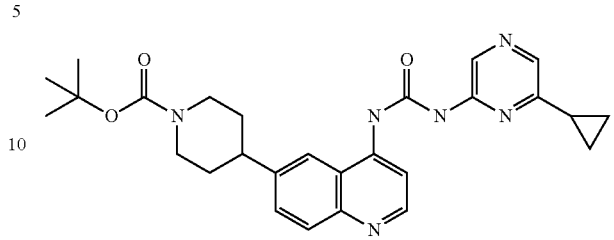

The title compound was prepared as described in example 29, substituting 1-(6-(1,2,3,6-tetrahydropyridin-4-yl)quinolin-4-yl)-3-(6-(trifluoromethyl)pyridin-2-yl)urea by tert-butyl 4-{4-[3-(6-cyclopropyl-pyrazin-2-yl)-ureido]-quinolin-6-yl}-3,6-dihydro-2H-pyridine-1-carboxylate (example 41).

ESI-MS [M+H$^+$]: 489.2

Example 43

1-(6-Cyclopropyl-pyrazin-2-yl)-3-(6-piperidin-4-yl-quinolin-4-yl)-urea

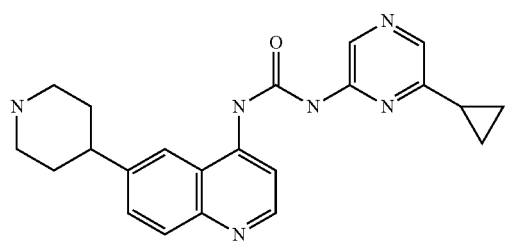 [SMILES: O=C(Nc1cncc(C2CC2)n1)Nc1ccnc2ccc(C3CCNCC3)cc12]

The title compound was prepared as described in example 28, substituting tert-butyl 4-{(4-[3-(6-trifluoromethyl-pyridin-2-yl)-ureido]-quinolin-6-yl}-3,6-dihydro-2H-pyridine-1-carboxylate by tert-butyl 4-{4-[3-(6-cyclopropyl-pyrazin-2-yl)-ureido]-quinolin-6-yl}-piperidine-1-carboxylate (example 42).

ESI-MS [M+H$^+$]: 389.2

Example 44

1-(6-Cyclopropyl-pyrazin-2-yl)-3-[6-(1-methyl-piperidin-4-yl)-quinolin-4-yl]-urea

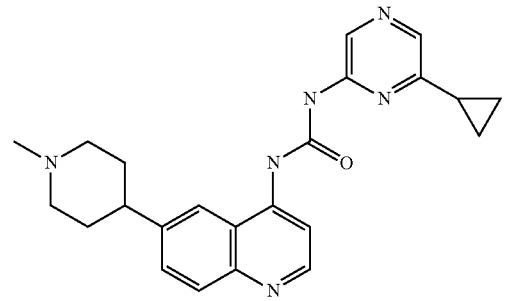 [SMILES: CN1CCC(c2ccc3nccc(NC(=O)Nc4cncc(C5CC5)n4)c3c2)CC1]

The title compound was prepared as described in example 30, substituting 1-[6-(1,2,3,6-tetrahydro-pyridin-4-yl)-quinolin-4-yl]-3-(6-trifluoromethyl-pyridin-2-yl)-urea by 1-(6-cyclopropyl-pyrazin-2-yl)-3-(6-piperidin-4-yl-quinolin-4-yl)-urea (example 43).

ESI-MS [M+H$^+$]: 403.1

Example 45 tert-Butyl 3-{4-[3-(6-Trifluoromethyl-pyridin-2-yl)-ureido]-quinolin-6-yl}-2,5-dihydro-pyrrole-1-carboxylate

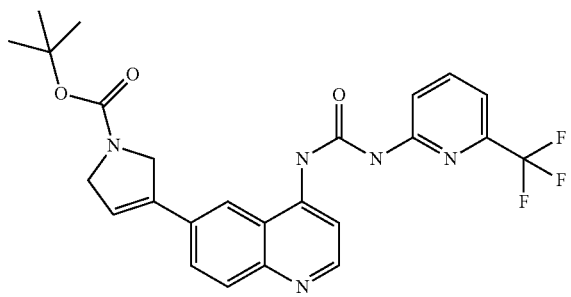 [SMILES: CC(C)(C)OC(=O)N1CC=C(c2ccc3nccc(NC(=O)Nc4cccc(C(F)(F)F)n4)c3c2)C1]

The title compound was prepared as described in example 27 step 2, substituting tert-butyl 4-(4,4,5,5-tetramethyl-1,3,2-dioxaborolan-2-yl)-5,6-dihydropyridine-1(2H)-carboxylate by tert-butyl 3-(4,4,5,5-tetramethyl-1,3,2-dioxaborolan-2-yl)-2,5-dihydro-1H-pyrrole-1-carboxylate.
ESI-MS [M+H+]: 500.2

Example 46

1-[6-(2,5-Dihydro-1H-pyrrol-3-yl)-quinolin-4-yl]-3-(6-trifluoromethyl-pyridin-2-yl)-urea

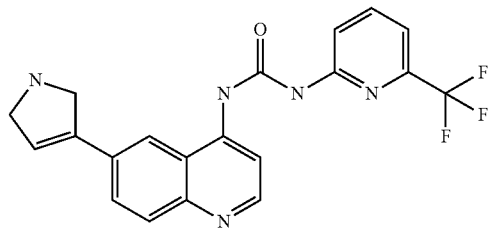 [SMILES: O=C(Nc1cccc(C(F)(F)F)n1)Nc1ccnc2ccc(C3=CCNC3)cc12]

The title compound was prepared as described in example 28, substituting tert-butyl 4-{4-[3-(6-trifluoromethyl-pyridin-2-yl)-ureido]-quinolin-6-yl}-3,6-dihydro-2H-pyridine-1-carboxylate by tert-butyl 3-{4-[3-(6-trifluoromethyl-pyridin-2-yl)-ureido]-quinolin-6-yl}-2,5-dihydro-pyrrole-1-carboxylate (example 45).
ESI-MS [M+H+]: 400.1

Example 47

1-[6-(3,6-Dihydro-2H-pyran-4-yl)-pyridin-2-yl]-3-(8-fluoro-quinolin-4-yl)-urea

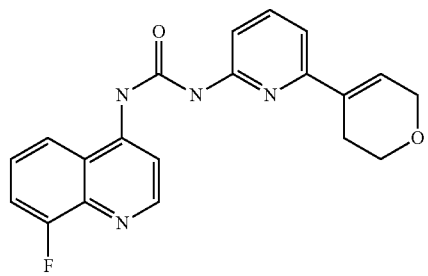

Step 1: 1-(8-Fluoroquinolin-4-yl)-3-(6-iodopyridin-2-yl)urea

The title compound was prepared as described in example 27 step 1, substituting 6-(trifluoromethyl)pyridin-2-amine by 4-amino-8-fluoroquinoline and 6-bromoquinolin-4-amine by 6-iodopyridin-2-amine.
ESI-MS [M+H+]: 409.0

Step 2: 1-[6-(3,6-Dihydro-2H-pyran-4-yl)-pyridin-2-yl]-3-(8-fluoro-quinolin-4-yl)-urea The title compound was prepared as described in example 27 step 2, substituting 1-(6-bromo-quinolin-4-yl)-3-(6-trifluoromethyl-pyridin-2-yl)-urea by 1-(8-fluoroquinolin-4-yl)-3-(6-iodopyridin-2-yl)urea (example 47, step 1) and tert-butyl 4-(4,4,5,5-tetramethyl-1,3,2-dioxaborolan-2-yl)-5,6-dihydropyridine-1(2H)-carboxylate by 2-(3,6-dihydro-2H-pyran-4-yl)-4,4,5,5-tetramethyl-1,3,2-dioxaborolane.
ESI-MS [M+H+]: 365.1

Example 48

1-(8-Fluoro-quinolin-4-yl)-3-[6-(tetrahydro-pyran-4-yl)-pyridin-2-yl]-urea

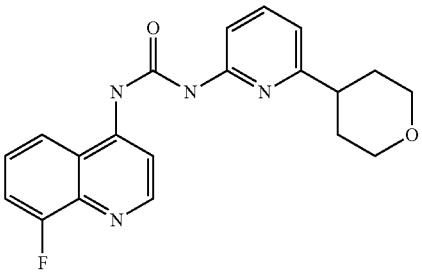 [SMILES: O=C(Nc1cccc(C2CCOCC2)n1)Nc1ccnc2c(F)cccc12]

The title compound was prepared as described in example 29, substituting 1-(6-(1,2,3,6-tetrahydropyridin-4-yl)quinolin-4-yl)-3-(6-(trifluoromethyl)pyridin-2-yl)urea by 1-[6-(3,6-dihydro-2H-pyran-4-yl)-pyridin-2-yl]-3-(8-fluoro-quinolin-4-yl)-urea (example 47) and by performing the hydrogenation at room temperature for at least 24 h.
ESI-MS [M+H+]: 367.15

Example 49

1-(8-Chloro-6-methyl-quinolin-4-yl)-3-[6-(tetrahydro-pyran-4-yl)-pyridin-2-yl]-urea

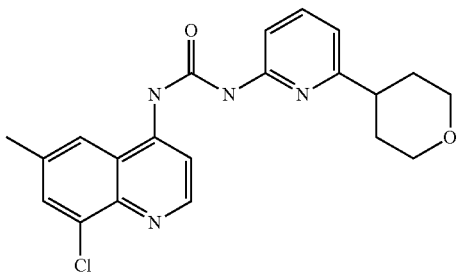 [SMILES: Cc1cc(Cl)c2nccc(NC(=O)Nc3cccc(C4CCOCC4)n3)c2c1]

The title compound was prepared as described in example 27 step 1, substituting 6-(trifluoromethyl)pyridin-2-amine by 4-amino-8-chloro-6-methylquinoline and 6-bromoquinolin-4-amine by 6-(tetrahydro-2H-pyran-4-yl)pyridin-2-amine.
ESI-MS [M+H+]: 397.1

Example 50

1-(6,8-Dichloro-quinolin-4-yl)-3-[6-(tetrahydro-pyran-4-yl)-pyridin-2-yl]-urea

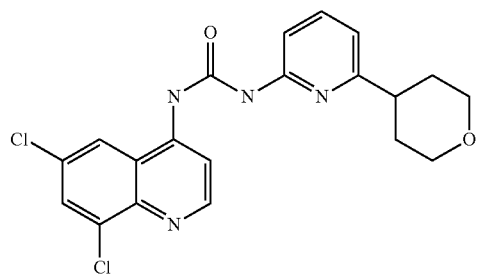 [SMILES: O=C(Nc1cccc(C2CCOCC2)n1)Nc1ccnc2c(Cl)cc(Cl)cc12]

The title compound was prepared as described in example 27 step 1, substituting 6-(trifluoromethyl)pyridin-2-amine by 6-(tetrahydro-2H-pyran-4-yl)pyridin-2-amine and 6-bromo-quinolin-4-amine by 4-amino-6,8-dichloroquinoline.
ESI-MS [M+H$^+$]: 418.1

Example 51

1-(6,8-Difluoro-quinolin-4-yl)-3-[6-(tetrahydro-pyran-4-yl)-pyridin-2-yl]-urea

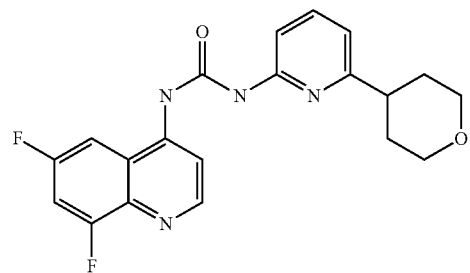 [SMILES: O=C(Nc1cccc(C2CCOCC2)n1)Nc1ccnc2c(F)cc(F)cc12]

The title compound was prepared as described in example 27 step 1, substituting 6-(trifluoromethyl)pyridin-2-amine by 4-amino-6,8-difluoroquinoline and 6-bromoquinolin-4-amine by 6-(tetrahydro-2H-pyran-4-yl)pyridin-2-amine.
ESI-MS [M+H$^+$]: 385.1

Example 52

1-(8-Chloro-quinolin-4-yl)-3-[6-(tetrahydro-pyran-4-yl)-pyridin-2-yl]-urea

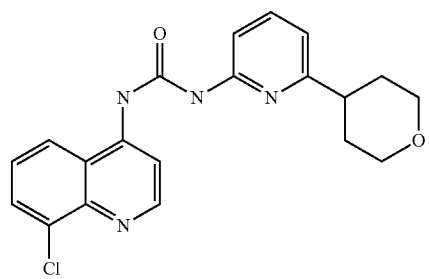

The title compound was prepared as described in example 27 step 1, substituting 6-(trifluoromethyl)pyridin-2-amine by 6-(tetrahydro-2H-pyran-4-yl)pyridin-2-amine and 6-bromo-quinolin-4-amine by 8-chloroquinolin-4-amine.
ESI-MS [M+H$^+$]: 383.2

Example 53

1-[1,5]Naphthyridin-4-yl-3-[6-(tetrahydro-pyran-4-yl)-pyridin-2-yl]-urea

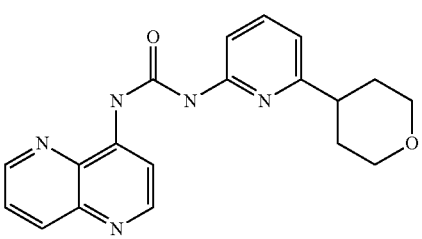 [SMILES: O=C(Nc1cccc(C2CCOCC2)n1)Nc1ccnc2cccnc12]

The title compound was prepared as described in example 27 step 1, substituting 6-(trifluoromethyl)pyridin-2-amine by 6-(tetrahydro-2H-pyran-4-yl)pyridin-2-amine and 6-bromo-quinolin-4-amine by 1,5-naphthyridin-4-amine.
ESI-MS [M+H$^+$]: 350.2

Example 54

1-(5,8-Difluoro-quinolin-4-yl)-3-[6-(tetrahydro-pyran-4-yl)-pyridin-2-yl]-urea

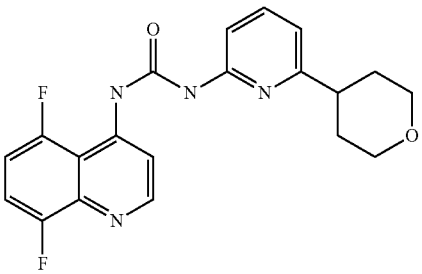 [SMILES: O=C(Nc1cccc(C2CCOCC2)n1)Nc1ccnc2c(F)ccc(F)c12]

The title compound was prepared as described in example 1 step 1, substituting 6-(trifluoromethyl)pyridin-2-amine by 5,8-difluoroquinolin-4-amine and 6-bromoquinolin-4-amine by 6-(tetrahydro-2H-pyran-4-yl)pyridin-2-amine.
ESI-MS [M+H$^+$]: 385.1

Example 55

1-(8-Fluoro-6-methoxy-quinolin-4-yl)-3-[6-(tetrahydro-pyran-4-yl)-pyridin-2-yl]-urea

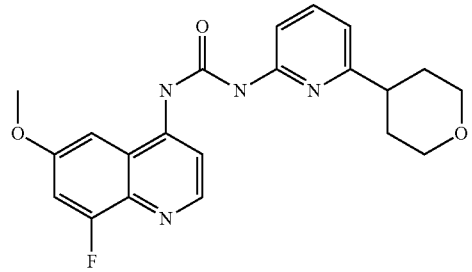

The title compound was prepared as described in example 27 step 1, substituting 6-(trifluoromethyl)pyridin-2-amine by 8-fluoro-6-methoxyquinolin-4-amine and 6-bromoquinolin-4-amine by 6-(tetrahydro-2H-pyran-4-yl)pyridin-2-amine.

ESI-MS [M+H$^+$]: 397.2

Example 56

1-[6-(5,6-Dihydro-4H-pyran-3-yl)-pyridin-2-yl]-3-(8-fluoro-quinolin-4-yl)-urea

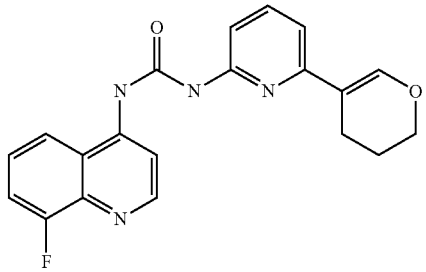

The title compound was prepared as described in example 27 step 2, substituting 1-(6-bromo-quinolin-4-yl)-3-(6-trifluoromethyl-pyridin-2-yl)-urea by 1-(8-fluoroquinolin-4-yl)-3-(6-iodopyridin-2-yl)urea (example 47, step 1) and tert-butyl 4-(4,4,5,5-tetramethyl-1,3,2-dioxaborolan-2-yl)-5,6-dihydropyridine-1(2H)-carboxylate by 2-(3,4-dihydro-2H-pyran-5-yl)-4,4,5,5-tetramethyl-1,3,2-dioxaborolane.

ESI-MS [M+H$^+$]: 365.1

Example 57

1-(8-Fluoro-quinolin-4-yl)-3-[6-(tetrahydro-pyran-3-yl)-pyridin-2-yl]-urea

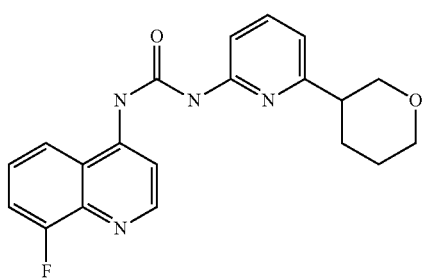

The title compound was prepared as described in example 29, substituting 1-(6-(1,2,3,6-tetrahydropyridin-4-yl)quinolin-4-yl)-3-(6-(trifluoromethyl)pyridin-2-yl)urea by 1-[6-(5,6-dihydro-4H-pyran-3-yl)-pyridin-2-yl]-3-(8-fluoro-quinolin-4-yl)-urea (example 56) and by performing the hydrogenation at room temperature for at least 24 h.

ESI-MS [M+H$^+$]: 367.15

Example 58

1-[6-(3,6-Dihydro-2H-pyran-4-yl)-pyridin-2-yl]-3-[1,5]naphthyridin-4-yl-urea

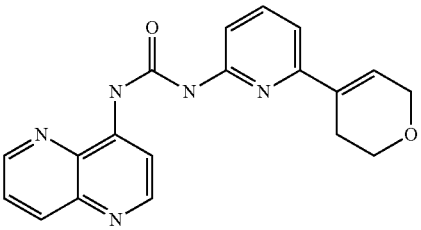 [SMILES: O=C(Nc1cccc(C2=CCOCC2)n1)Nc1ccnc2cccnc12]

Step 1: 1-(6-iodopyridin-2-yl)-3-(1,5-naphthyridin-4-yl)urea

The title compound was prepared as described in example 27 step 1, substituting 6-(trifluoromethyl)pyridin-2-amine by 6-iodopyridin-2-amine and 6-bromoquinolin-4-amine by 1,5-naphthyridin-4-ylamine.

ESI-MS [M+H$^+$]: 392.0

Step 2: 1-[6-(3,6-Dihydro-2H-pyran-4-yl)-pyridin-2-yl]-3-[1,5]naphthyridin-4-yl-urea The title compound was prepared as described in example 27 step 2, substituting 1-(6-bromo-quinolin-4-yl)-3-(6-trifluoromethyl-pyridin-2-yl)-urea by 1-(6-iodopyridin-2-yl)-3-(1,5-naphthyridin-4-yl)urea (example 58, step 1) and tert-butyl 4-(4,4,5,5-tetramethyl-1,3,2-dioxaborolan-2-yl)-5,6-dihydropyridine-1(2H)-carboxylate by 2-(3,6-dihydro-2H-pyran-4-yl)-4,4,5,5-tetramethyl-1,3,2-dioxaborolane.

ESI-MS [M+H$^+$]: 348.1

Example 59 tert-Butyl-6-[3-(8-fluoro-quinolin-4-yl)-ureido]-3',6'-dihydro-2'H-[2,4']bipyridinyl-1'-carboxylate

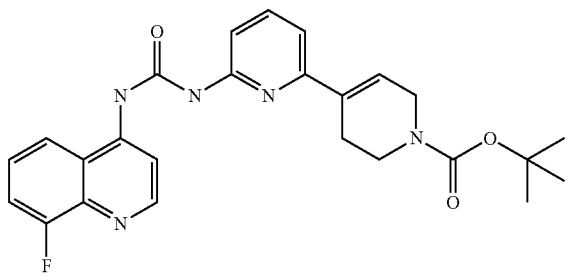 [SMILES: CC(C)(C)OC(=O)N1CC=C(c2cccc(NC(=O)Nc3ccnc4c(F)cccc34)n2)CC1]

The title compound was prepared as described in example 27 step 2, substituting 1-(6-bromo-quinolin-4-yl)-3-(6-trifluoromethyl-pyridin-2-yl)-urea by 1-(8-fluoroquinolin-4-yl)-3-(6-iodopyridin-2-yl)urea (example 47 step 1).

ESI-MS [M+H$^+$]: 464.0

Example 60

1-(8-Fluoro-quinolin-4-yl)-3-(1',2',3',6'-tetrahydro-[2,4']bipyridinyl-6-yl)-urea

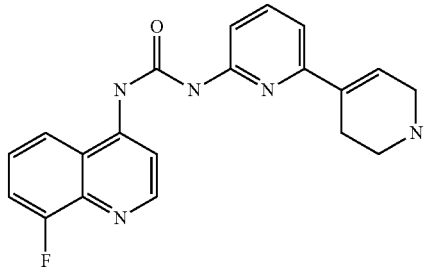 [SMILES: O=C(Nc1cccc(C2=CCNCC2)n1)Nc1ccnc2c(F)cccc12]

The title compound was prepared as described in example 28, substituting tert-butyl 4-{4-[3-(6-trifluoromethyl-pyridin-2-yl)-ureido]-quinolin-6-yl}-3,6-dihydro-2H-pyridine-1-carboxylate by tert-butyl-6-[3-(8-fluoro-quinolin-4-yl)-ureido]-3',6'-dihydro-2'H-[2,4']bipyridinyl-1'-carboxylate (example 59).

ESI-MS [M+H$^+$]: 364.0

Example 61 tert-Butyl-6-[3-(8-fluoro-quinolin-4-yl)-ureido]-3',4',5',6'-tetrahydro-2'H-[2,4']bipyridinyl-1'-carboxylate

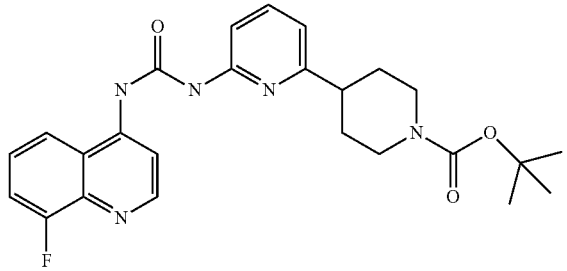 [SMILES: CC(C)(C)OC(=O)N1CCC(c2cccc(NC(=O)Nc3ccnc4c(F)cccc34)n2)CC1]

0.340 g of tert-butyl-6-[3-(8-fluoro-quinolin-4-yl)-ureido]-3',6'-dihydro-2'H-[2,4']bipyridinyl-1'-carboxylate (0.734 mmol) were dissolved in a mixture of 220 ml of DMF and 125 ml of methanol. After addition of 0.078 g of Pd/C (0.734 mmol) and 0.5 ml of acetic acid (8.73 mmol) hydrogenation was performed for 24 h at room temperature, which led to complete double bond hydrogenation according to HPLC/MSD analysis. The catalyst was filtered off, the solvent removed under reduced pressure and the residue extracted three times with ethyl acetate after adding water and a small amount of NaOH (pH 9). The combined organic phases were washed with a small amount of brine, dried over sodium sulfate and the solvent was removed under reduced pressure. 300 mg of the desired product were obtained as a powder (yield: 88%).

ESI-MS [M+H$^+$]: 466.2

Example 62

1-(8-Fluoro-quinolin-4-yl)-3-(1',2',3',4',5',6'-hexahydro-[2,4']bipyridinyl-6-yl)-urea

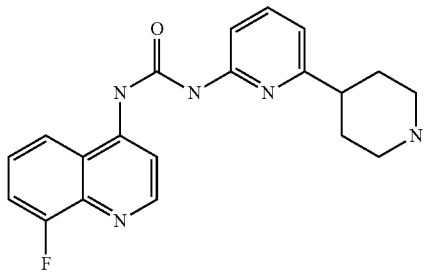 [SMILES: O=C(Nc1cccc(C2CCNCC2)n1)Nc1ccnc2c(F)cccc12]

The title compound was prepared as described in example 28, substituting tert-butyl 4-{4-[3-(6-trifluoromethyl-pyridin-2-yl)-ureido]-quinolin-6-yl}-3,6-dihydro-2H-pyridine-1-carboxylate by tert-butyl-6-[3-(8-fluoro-quinolin-4-yl)-ureido]-3',4',5',6'-tetrahydro-2'H-[2,4']bipyridinyl-1'-carboxylate (example 61).

ESI-MS [M+H$^+$]: 366.2

Example 63

1-(8-Fluoro-quinolin-4-yl)-3-(1'-methyl-1',2',3',4',5',6'-hexahydro-[2,4']bipyridinyl-6-yl)-urea

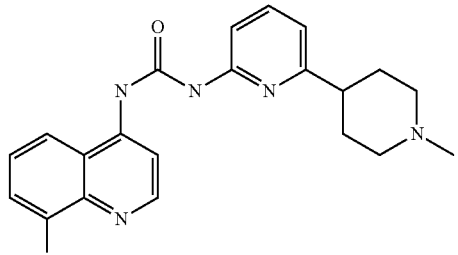

The title compound was prepared as described in example 30, substituting 1-[6-(1,2,3,6-tetrahydro-pyridin-4-yl)-quinolin-4-yl]-3-(6-trifluoromethyl-pyridin-2-yl)-urea by 1-(8-fluoro-quinolin-4-yl)-3-(1',2',3',4',5',6'-hexahydro-[2,4']bipyridinyl-6-yl)-urea (example 62).

ESI-MS [M+H$^+$]: 380.2

Example 64

1-[1'-(2-Fluoro-ethyl)-1',2',3',4',5',6'-hexahydro-[2,4']bipyridinyl-6-yl]-3-(8-fluoro-quinolin-4-yl)-urea

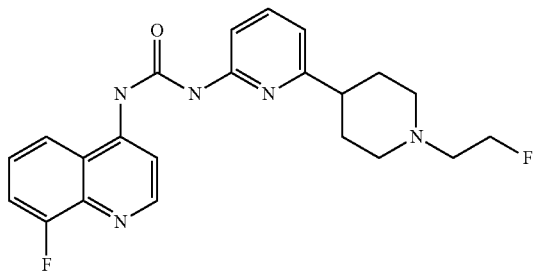 [SMILES: O=C(Nc1cccc(C2CCN(CCF)CC2)n1)Nc1ccnc2c(F)cccc12]

The title compound was prepared as described in example 32, substituting 1-(6-(piperidin-4-yl)quinolin-4-yl)-3-(6-(trifluoromethyl)pyridin-2-yl)urea by 1-(8-fluoro-quinolin-4-yl)-3-(1',2',3',4',5',6'-hexahydro-[2,4']bipyridinyl-6-yl)-urea (example 62).

ESI-MS [M+H+]: 412.2

Example 65

1-[1'-(2,2-Difluoro-ethyl)-1',2',3',4',5',6'-hexahydro-[2,4']bipyridinyl-6-yl]-3-(8-fluoro-quinolin-4-yl)-urea

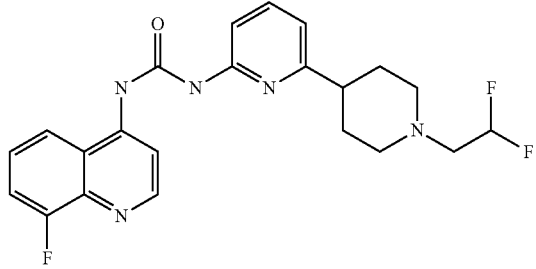 [SMILES: O=C(Nc1cccc(C2CCN(CC(F)F)CC2)n1)Nc1ccnc2c(F)cccc12]

The title compound was prepared as described in example 32, substituting 1-(6-(piperidin-4-yl)quinolin-4-yl)-3-(6-(trifluoromethyl)pyridin-2-yl)urea by 1-(8-fluoro-quinolin-4-yl)-3-(1',2',3',4',5',6'-hexahydro-[2,4']bipyridinyl-6-yl)-urea (example 62) and 1-bromo-2-fluoroethane by 1,1-difluoro-2-iodoethane.

ESI-MS [M+H+]: 430.2

Example 66

1-(8-Fluoro-quinolin-4-yl)-3-(1'-isopropyl-1',2',3',4',5',6'-hexahydro-[2,4']bipyridinyl-6-yl)-urea

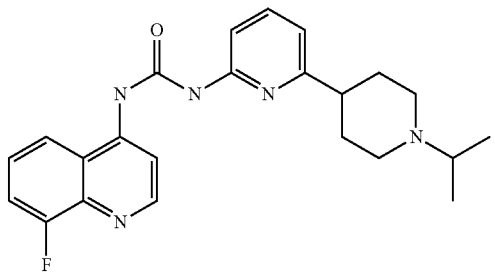 [SMILES: CC(C)N1CCC(c2cccc(NC(=O)Nc3ccnc4c(F)cccc34)n2)CC1]

To a solution of 50 mg of 1-(8-fluoro-quinolin-4-yl)-3-(1',2',3',4',5',6'-hexahydro-[2,4']bipyridinyl-6-yl)-urea (example 62) (0.137 mmol) in 50 ml of acetone were added 26 mg of sodium borohydride (0.684 mmol) in small portions. The reaction was slightly exotherm. After stirring the reaction mixture over night a small amount of 2M HCl was added to the reaction mixture up to a pH of 3 to destroy the excess of sodium borohydride. After neutralization with sodium bicarbonate, acetone was evaporated under reduced pressure, water added to the residue, the reaction mixture extracted three times with DCM, the organic phases combined and dried over sodium sulfate and the solvent evaporated under reduced pressure. 45 mg of the desired product were obtained as off white powder (yield: 81%) after column chromatography (silica gel, DCM/MeOH 98/2).

ESI-MS [M+H+]: 408.2

Example 67

1-(8-Fluoro-quinolin-4-yl)-3-[5-(tetrahydro-pyran-4-yl)-pyridin-2-yl]-urea

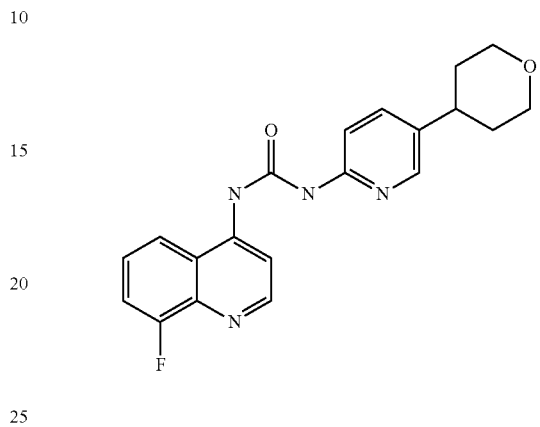

Step 1:
5-(3,6-Dihydro-2H-pyran-4-yl)pyridin-2-amine 0.220 g of 5-iodopyridin-2-amine (1.0 mmol), 0.315 g of 2-(3,6-dihydro-2H-pyran-4-yl)-4,4,5,5-tetramethyl-1,3,2-dioxaborolane (1.50 mmol), 0.116 g of tetrakis(triphenylphosphine)palladium(0) (0.100 mmol) and 2.25 ml of a 2M sodium carbonate solution (4.50 mmol) were dissolved/suspended in 8.6 ml of DMF in a microwave vessel, flushed with vacuum/argon, and subsequently heated in the microwave for 20 min at 120° C. HPLC/MSD indicated almost complete formation of the desired product. The solvent was evaporated under reduced pressure, 2M HCl was added to the residue and the mixture extracted three times with DCM. To the acidic water phase 2M NaOH was added up to pH 9 and the mixture was extracted three times with ethyl acetate. The combined ethyl acetate solutions were washed once with brine, dried over sodium sulfate and the solvent removed under reduced pressure. 195 mg of the desired product were obtained as yellow powder (yield: quant.). The quite pure raw material (about 90%) was used without further purification in the next step.

ESI-MS [M+H+]: 177.1

Step 2:
5-(Tetrahydro-2H-pyran-4-yl)pyridin-2-amine

The title compound was prepared as described in example 61, substituting tert-butyl-6-[3-(8-fluoro-quinolin-4-yl)-ureido]-3',6'-dihydro-2'H-[2,4']bipyridinyl-1'-carboxylate by 5-(3,6-dihydro-2H-pyran-4-yl)pyridin-2-amine and by using ethanol as solvent.

ESI-MS [M+H+]: 179.1

Step 3: 1-(8-Fluoro-quinolin-4-yl)-3-[5-(tetrahydro-pyran-4-yl)-pyridin-2-yl]-urea The title compound was prepared as described in example 27 step 1, substituting 6-(trifluoromethyl)pyridin-2-amine by 8-fluoroquinolin-4-amine and 6-bromoquinolin-4-amine by 5-(tetrahydro-2H-pyran-4-yl)pyridin-2-amine (example 67, step 2).

ESI-MS [M+H+]: 367.1

Example 68 tert-Butyl-3-[4-(3-pyrazin-2-yl-ureido)-quinolin-6-yl]-2,5-dihydro-pyrrole-1-carboxylate

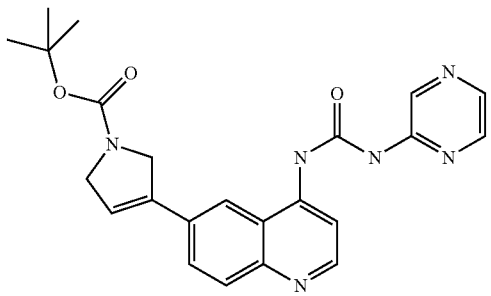 [SMILES: CC(C)(C)OC(=O)N1CC=C(c2ccc3nccc(NC(=O)Nc4cnccn4)c3c2)C1]

The title compound was prepared as described in example 27 step 2, substituting 1-(6-bromo-quinolin-4-yl)-3-(6-trifluoromethyl-pyridin-2-yl)-urea by 1-(6-bromoquinolin-4-yl)-3-(pyrazin-2-yl)urea (example 9, step 1) and tert-butyl 4-(4,4,5,5-tetramethyl-1,3,2-dioxaborolan-2-yl)-5,6-dihydropyridine-1(2H)-carboxylate by tert-butyl 3-(4,4,5,5-tetramethyl-1,3,2-dioxaborolan-2-yl)-2,5-dihydro-1H-pyrrole-1-carboxylate.

ESI-MS [M+H$^+$]: 433.2

Example 69 tert-Butyl-3-[4-(3-pyrazin-2-yl-ureido)-quinolin-6-yl]-pyrrolidine-1-carboxylate

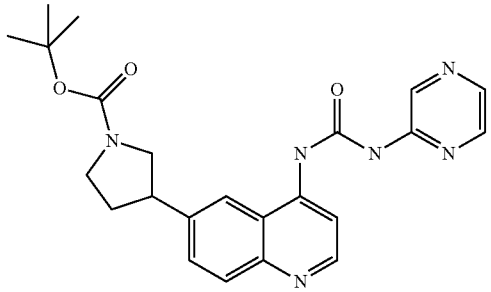 [SMILES: CC(C)(C)OC(=O)N1CCC(c2ccc3nccc(NC(=O)Nc4cnccn4)c3c2)C1]

The title compound was prepared as described in example 61, substituting tert-butyl-6-[3-(8-fluoro-quinolin-4-yl)-ureido]-3',6'-dihydro-2'H-[2,4']bipyridinyl-1'-carboxylate by tert-butyl-3-[4-(3-pyrazin-2-yl-ureido)-quinolin-6-yl]-2,5-dihydro-pyrrole-1-carboxylate (example 68).

ESI-MS [M+H+]: 435.2

Example 70

1-Pyrazin-2-yl-3-(6-pyrrolidin-3-yl-quinolin-4-yl)-urea

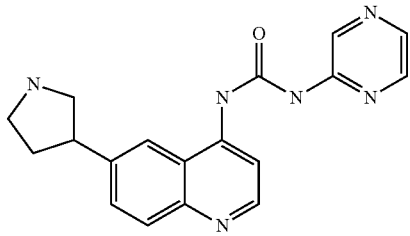 [SMILES: O=C(Nc1cnccn1)Nc1ccnc2ccc(C3CCNC3)cc12]

To a solution of 50 mg of tert-butyl-3-[4-(3-pyrazin-2-yl-ureido)-quinolin-6-yl]-pyrrolidine-1-carboxylate (example 43) (0.120 mmol) in 5 ml of DCM was added 1 ml of 6M HCl solution in propanol-2 with stirring at room temperature. After reaction over night the solvent and excess HCl was removed in vacuum, and the residue was co-distilled at least three times with propanol-2. 50 mg of the desired product were obtained as powder as the di-hydrochloride salt (yield: quant.).

ESI-MS [M+H$^+$]: 335.1

II. Biological Tests

The compounds according to the invention exhibit very good affinities for GSK-3 (<1 μM, frequently <100 nM) and exhibited good selectivity against multiple kinase targets.

Methods—Biochemical hGSK-3beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 μCi 33P-ATP, 10 μM ATP, 0.0125 U hGSK-3β(Upstate cell signaling solutions) and 1 μM substrate (biotin-YRRAAVPPSPSLSRHSSPHQ(pS)EDEEE) in 50 mM HEPES, 10 mM MgCl$_2$, 100 mM Na$_3$VO$_4$, 1 mM DTT, 0.0075% Triton, 2% DMSO (total volume 50 μL) for 30 minutes at room temperature. The incubation was stopped by addition of an equal volume of 100 mM EDTA, 4M NaCl. 80 μL of this mixture was added to streptavidin-coated Flash-plates (Perkin Elmer). Following a wash step, 33P incorporation was quantified on a MicroBeta microplate liquid scintillation counter (PerkinElmer). IC$_{50}$'s were determined by fitting a sigmoidal dose-response curve to the counts obtained at the different concentrations in GraphPad Prism.

The results of the binding tests are given in the table below.

| Example # | GSK-3β IC$_{50}$ |
|---|---|
| 1 | +++ |
| 2 | +++ |
| 3 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ | n.d. not determined

GSK-3β IC$_{50}$:

+ >10 μM

++ from 100 nM to 10 μM

+++ <100 nM

We claim:
1. A heterocyclic compound of the formula (I)

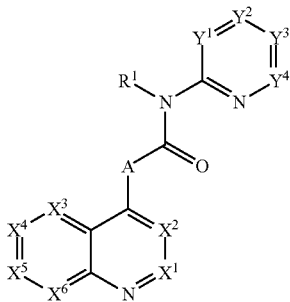

or a stereoisomer, N-oxide, tautomer and/or physiologically tolerated acid addition salt thereof,
or a compound of formula I, wherein at least one of the atoms has been replaced by its stable, non-radioactive isotope, wherein
A is $NR^B$, where $R^B$ is hydrogen;
$X^1$ and $X^2$ are $CR^2$;
$X^3$ is selected from the group consisting of $CR^3$, $CR^4$ and N;
$X^4$, $X^5$ and $X^6$ are independently of each other selected from the group consisting of $CR^3$ and $CR^4$;
with the proviso that no more than two of $X^3$, $X^4$, $X^5$ and $X^6$ are $CR^4$;
$Y^1$, $Y^2$, $Y^3$ and $Y^4$ are independently of each other selected from the group consisting of $CR^4$, $CR^5$, and N;
with the proviso that at most one of $Y^1$, $Y^2$, $Y^3$ and $Y^4$ is N and with the proviso that at most one of $Y^1$, $Y^2$, $Y^3$ and $Y^4$ is $CR^4$; and
with the proviso that one of $Y^1$, $Y^2$, $Y^3$ and $Y^4$ is $CR^4$ or C—$CF_3$ if none of $X^3$, $X^4$, $X^5$ and $X^6$ is $CR^4$;
$R^1$ is hydrogen;
each $R^2$ is independently selected from the group consisting of hydrogen, OH, halogen, CN, $C_1$-$C_6$-alkyl, $C_1$-$C_6$-haloalkyl, $C_1$-$C_6$-alkoxy, $C_1$-$C_6$-haloalkoxy, and $NR^aR^b$; or two radicals $R^2$ bonded at the carbon atoms of groups $X^1$ and $X^2$, together with the carbon atoms to which they are bonded, form a 5- or 6-membered saturated or unsaturated ring which may contain 1 or 2 heteroatoms as ring members selected from the group consisting of N, O, and S and which optionally carries 1, 2, or 3 substituents $R^6$;
each $R^3$ is independently selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$, and an aromatic radical Ar, which is selected from the group consisting of phenyl and a 5- or 6-membered N- or C-bound heteroaromatic radical comprising one nitrogen atom and optionally 1, 2, or 3 further heteroatoms independently selected from the group consisting of O, S, and N as ring members, wherein Ar is unsubstituted or carries one or two radicals $R^7$ and wherein Ar may also be bonded via a $CH_2$ group;
$R^4$ is a C-bound saturated or partially unsaturated monocyclic 3-, 4-, 5-, 6-, or 7-membered heterocyclic ring containing 1, 2, or 3 heteroatoms or heteroatom-containing groups selected from the group consisting of O, N, S, NO, SO, and $SO_2$ as ring members, where the heterocyclic ring optionally carries 1, 2, or 3 C- or N-bound substituents $R^8$;
$R^5$ is selected from the group consisting of hydrogen, CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$, and an aromatic radical Ar, which is selected from the group consisting of phenyl and a 5- or 6-membered N- or C-bound heteroaromatic radical comprising one nitrogen atom and optionally 1, 2, or 3 further heteroatoms independently selected from the group consisting of O, S, and N as ring members, wherein Ar is unsubstituted or carries one or two radicals $R^7$ and wherein Ar may also be bonded via a $CH_2$ group;
$R^6$ and $R^8$, independently of each other and independently of each occurrence, are selected from the group consisting of CN, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkyl-$NR^aR^b$, and an aromatic radical Ar, which is selected from the group consisting of phenyl and a 5- or 6-membered N- or C-bound heteroaromatic radical comprising one nitrogen atom and optionally 1, 2, or 3 further heteroatoms independently selected from the group consisting of O, S, and N as ring members, wherein Ar is unsubstituted or carries one or two radicals $R^7$ and wherein Ar may also be bonded via a $CH_2$ group;
each $R^7$ is independently selected from the group consisting of halogen, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, a phenyl group, and a 5- or 6-membered heteroaromatic radical comprising one nitrogen atom and optionally 1, 2 or 3 further heteroatoms independently selected from the group consisting of O, S, and N as ring members, wherein phenyl and the heteroaromatic radical are, independently of each other, unsubstituted or substituted by 1, 2, 3, or 4 radicals selected from the group consisting of halogen, cyano, $C_1$-$C_4$-alkyl, $C_1$-$C_4$-haloalkyl, $C_1$-$C_4$-alkoxy, and $C_1$-$C_4$-haloalkoxy; and
$R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl, and $C_1$-$C_4$-haloalkylcarbonyl;
or $R^a$ and $R^b$ form, together with the nitrogen atom to which they are bonded, a 3-, 4-, 5-, 6-, or 7-membered saturated or unsaturated aromatic or non-aromatic N-heterocyclic ring, which may contain 1 further heteroatom or heteroatom containing group selected from the group consisting of O, S, SO, SO, and N as a ring member.

2. The heterocyclic compound of claim 1, wherein either one of $X^3$, $X^4$, $X^5$, and $X^6$ is $CR^4$ and none of $Y^1$, $Y^2$, $Y^3$, and $Y^4$ is $CR^4$, or one of $Y^1$, $Y^2$, $Y^3$ and $Y^4$ is $CR^4$ and none of $X^3$, $X^4$, $X^5$, and $X^6$ is $CR^4$.

3. The heterocyclic compound of claim 1, wherein one of $Y^1$, $Y^2$, $Y^3$, and $Y^4$ is $CR^4$ if none of $X^3$, $X^4$, $X^5$, and $X^6$ is $CR^4$.

4. The heterocyclic compound of claim 1, wherein one of $Y^1, Y^2, Y^3$, and $Y^4$ is C—CF$_3$ if none of $X^3, X^4, X^5$, and $X^6$ is CR$^4$.

5. The heterocyclic compound of claim 1, wherein R$^4$ is selected from a C-bound saturated or partially unsaturated monocyclic 4-, 5-, or 6-membered heterocyclic ring containing 1 or 2 or 3 heteroatoms selected from the group consisting of O, N, S, and SO, as ring members, where the heterocyclic ring optionally carries 1, 2, or 3 substituents R$^8$.

6. The heterocyclic compound of claim 5, wherein R$^4$ is selected from the group consisting of C-bound oxetanyl, thietanyl, azetidinyl, tetrahydrofuranyl, tetrahydrothienyl, tetrahydrothienyl-1-oxide, pyrrolidinyl, pyrrolinyl, pyrazolidinyl, pyrazolinyl, imidazolidinyl, imidazolinyl, tetrahydropyranyl, dihydropyranyl, piperidinyl, tetrahydropyridinyl, dihydropyridinyl, piperazinyl, and morpholinyl, where the heterocyclic ring optionally carries 1, 2, or 3 substituents R$^8$.

7. The heterocyclic compound of claim 6, wherein R$^4$ is selected from the group consisting of C-bound oxetanyl, azetidinyl, tetrahydrofuranyl, tetrahydrothienyl, tetrahydrothienyl-1-oxide, pyrrolidinyl, pyrrolinyl, tetrahydropyranyl, dihydropyranyl, piperidinyl, tetrahydropyridinyl, dihydropyridinyl, piperazinyl, and morpholinyl, where the heterocyclic ring optionally carries 1, 2, or 3 substituents R$^8$.

8. The heterocyclic compound of claim 7, wherein R$^4$ is selected from the group consisting of azetidin-3-yl, tetrahydrofuran-3-yl, pyrrolidin-3-yl, pyrrolin-3-yl, tetrahydropyran-4-yl, tetrahydropyran-3-yl, dihydropyran-4-yl, dihydropyran-3-yl, piperidin-4-yl, 1,2,5,6-tetrahydropyridin-4-yl, and 1,2-dihydropyridin-4-yl, where the heterocyclic ring optionally carries 1, 2, or 3 substituents R$^8$.

9. The heterocyclic compound of claim 1, wherein R$^8$ is selected from the group consisting of C$_1$-C$_6$-alkyl, C$_1$-C$_6$-haloalkyl, C$_3$-C$_7$-cycloalkyl, C$_3$-C$_7$-halocycloalkyl, C$_2$-C$_4$-alkenyl, C$_2$-C$_4$-haloalkenyl, C$_1$-C$_6$-alkoxy, C$_1$-C$_6$-haloalkoxy, formyl, C$_1$-C$_6$-alkylcarbonyl, C$_1$-C$_6$-haloalkylcarbonyl, C$_1$-C$_6$-alkoxycarbonyl, C$_1$-C$_6$-haloalkoxycarbonyl, and benzyl.

10. The heterocyclic compound of claim 1, wherein R$^8$ is N-bound.

11. The heterocyclic compound of claim 1, wherein R$^4$ is a structure selected from the group consisting of:

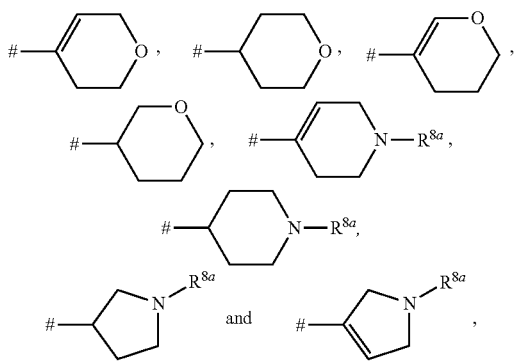

where
R$^{8a}$ is hydrogen or has one of the meanings given in claim 1 for R$^8$; and
# is the attachment point to the remainder of the molecule.

12. The heterocyclic compound of claim 1, wherein X$^1$ and X$^2$ are CR$^2$ and X$^3$, X$^4$, X$^5$, and X$^6$ are CR$^3$ or CR$^4$, or wherein X$^1$ and X$^2$ are CR$^2$, X$^3$ is N and X$^4$, X$^5$, and X$^6$ are CR$^3$ or CR$^4$.

13. The heterocyclic compound of claim 1, wherein Y$^1$, Y$^2$, Y$^3$, and Y$^4$ are CR$^4$ or CR$^5$, or wherein Y$^2$ is N and Y$^3$ and Y$^4$ are CR$^4$ or CR$^5$.

14. The heterocyclic compound of claim 1, wherein R$^2$ is hydrogen.

15. The heterocyclic compound of claim 1, wherein R$^3$ is selected from the group consisting of hydrogen, CN, halogen, C$_1$-C$_6$alkyl, C$_1$-C$_6$haloalkyl, C$_3$-C$_7$-cycloalkyl, C$_3$-C$_7$-halocycloalkyl, C$_1$-C$_6$alkoxy, C$_1$-C$_6$haloalkoxy, formyl, C$_1$-C$_6$alkylcarbonyl, C$_1$-C$_6$-haloalkylcarbonyl, C$_1$-C$_6$alkoxycarbonyl, and C$_1$-C$_6$haloalkoxycarbonyl.

16. The heterocyclic compound of claim 1, wherein 0, 1, or 2 of the radicals R$^3$ are different from hydrogen.

17. The heterocyclic compound of claim 1, wherein R$^5$ is selected from the group consisting of hydrogen, CN, halogen, C$_1$-C$_6$alkyl, C$_1$-C$_6$haloalkyl, C$_3$-C$_7$-cycloalkyl, C$_3$-C$_7$-halocycloalkyl, C$_1$-C$_6$alkoxy, C$_1$-C$_6$haloalkoxy, formyl, C$_1$-C$_6$alkylcarbonyl, C$_1$-C$_6$-haloalkylcarbonyl, C$_1$-C$_6$alkoxycarbonyl and C$_1$-C$_6$haloalkoxycarbonyl.

18. The heterocyclic compound of claim 1, wherein at most one of the radicals R$^5$ is different from hydrogen.

19. The heterocyclic compound of claim 1, of formula I-1

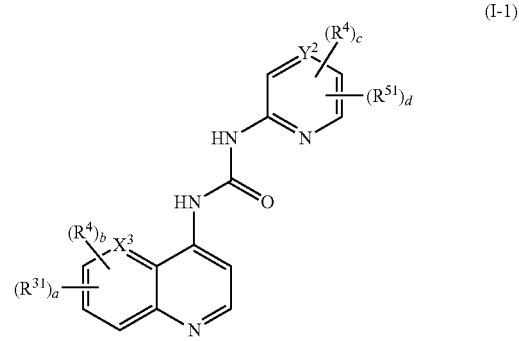

where
X$^3$ is N or CH;
Y$^2$ is N or CH;
R$^{31}$ has one of the meanings given in claim 1 for R$^3$, except for hydrogen;
R$^4$ has one of the meanings given in claim 1;
R$^{51}$ has one of the meanings given in claim 1 for R$^5$, except for hydrogen;
a is 0, 1, or 2; and
b, c, and d are independently of each other 0 or 1, with the proviso that one of b and c is 1.

20. The heterocyclic compound of claim 1, of formula I-2

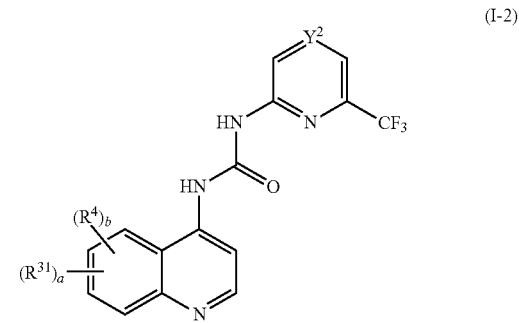

where

Y² is N or CH;

R³¹ has one of the meanings given in claim 1 for R³, except for hydrogen;

R⁴ has one of the meanings given in claim 1;

a is 0, 1, or 2; and b is 0 or 1.

21. The heterocyclic compound of claim 20, where Y² is CH, b is 0, and a is 0, 1, or 2, and where R³¹, if present, is selected from the group consisting of halogen, trifluoromethyl, cyano, and methoxy.

22. A heterocyclic compound selected from the group consisting of:

1-(6-(3,6-dihydro-2H-pyran-4-yl)pyridin-2-yl)-3-(8-fluoroquinolin-4-yl)urea;
1-(8-fluoroquinolin-4-yl)-3-(6-(tetrahydro-2H-pyran-4-yl)pyridin-2-yl)urea;
1-(6-(3,4-dihydro-2H-pyran-5-yl)pyridin-2-yl)-3-(8-fluoroquinolin-4-yl)urea;
1-(6-(3,6-dihydro-2H-pyran-4-yl)pyridin-2-yl)-3-(7-methoxyquinolin-4-yl)urea;
1-(6-(3,4-dihydro-2H-pyran-5-yl)quinolin-4-yl)-3-(6-(trifluoromethyl)pyridin-2-yl)-urea;
1-(7-(3,6-dihydro-2H-pyran-4-yl)quinolin-4-yl)-3-(6-(trifluoromethyl)pyridin-2-yl)-urea;
1-(6-(tetrahydro-2H-pyran-4-yl)quinolin-4-yl)-3-(6-(trifluoromethyl)pyridin-2-yl)-urea;
1-(7-methoxyquinolin-4-yl)-3-(6-(tetrahydro-2H-pyran-4-yl)pyridin-2-yl)urea;
1-(7-(tetrahydro-2H-pyran-4-yl)quinolin-4-yl)-3-(6-(trifluoromethyl)pyridin-2-yl)-urea;
1-(6-(tetrahydro-2H-pyran-3-yl)quinolin-4-yl)-3-(6-(trifluoromethyl)pyridin-2-yl)-urea;
1-(7-(3,6-dihydro-2H-pyran-4-yl)quinolin-4-yl)-3-(pyrazin-2-yl)urea;
1-(6-(3,4-dihydro-2H-pyran-5-yl)pyridin-2-yl)-3-(7-methoxyquinolin-4-yl)urea;
1-(7-methoxyquinolin-4-yl)-3-(6-(tetrahydro-2H-pyran-3-yl)pyridin-2-yl)urea;
1-(pyrazin-2-yl)-3-(7-(tetrahydro-2H-pyran-4-yl)quinolin-4-yl)urea;
1-(7-(3,4-dihydro-2H-pyran-5-yl)quinolin-4-yl)-3-(6-(trifluoromethyl)pyridin-2-yl)-urea;
1-(6-bromo-quinolin-4-yl)-3-(6-trifluoromethyl-pyridin-2-yl)-urea;
1-(6-(trifluoromethyl)pyridin-2-yl)-3-quinolin-4-yl-urea;
1-(6,8-difluoroquinolin-4-yl)-3-(6-trifluoromethyl-pyridin-2-yl)-urea;
1-(7-bromoquinolin-4-yl)-3-(6-trifluoromethyl-pyridin-2-yl)-urea;
1-(7-trifluoromethylquinolin-4-yl)-3-(6-trifluoromethyl-pyridin-2-yl)-urea;
1-(7-methoxyquinolin-4-yl)-3-(6-trifluoromethyl-pyridin-2-yl)-urea;
1-(8-trifluoromethylquinolin-4-yl)-3-(6-trifluoromethyl-pyridin-2-yl)-urea;
1-(8-cyanoquinolin-4-yl)-3-(6-trifluoromethyl-pyridin-2-yl)-urea;
1-(8-iodoquinolin-4-yl)-3-(6-trifluoromethyl-pyridin-2-yl)-urea;
1-(8-cyanoquinolin-4-yl)-3-pyrazin-2-yl-urea;
1-(7-methoxyquinolin-4-yl)-3-pyrazin-2-yl-urea;
tert-butyl 4-{4-[3-(6-trifluoromethyl-pyridin-2-yl)-ureido]-quinolin-6-yl}-3,6-dihydro-2H-pyridine-1-carboxylate;
1-[6-(1,2,3,6-tetrahydro-pyridin-4-yl)-quinolin-4-yl]-3-(6-trifluoromethyl-pyridin-2-yl)-urea;
1-(6-(piperidin-4-yl)quinolin-4-yl)-3-(6-(trifluoromethyl)pyridin-2-yl)urea;
1-[6-(1-methyl-1,2,3,6-tetrahydro-pyridin-4-yl)-quinolin-4-yl]-3-(6-trifluoromethyl-pyridin-2-yl)-urea;
1-[6-(1-methyl-piperidin-4-yl)-quinolin-4-yl]-3-(6-trifluoromethyl-pyridin-2-yl)-urea;
1-{6-[1-(2-fluoro-ethyl)-piperidin-4-yl]-quinolin-4-yl}-3-(6-trifluoromethyl-pyridin-2-yl)-urea;
1-{6-[1-(2,2-difluoro-ethyl)-piperidin-4-yl]-quinolin-4-yl}-3-(6-trifluoromethyl-pyridin-2-yl)-urea;
1-[6-(3,6-dihydro-2H-pyran-4-yl)-quinolin-4-yl]-3-(6-trifluoromethyl-pyridin-2-yl)-urea;
1-[6-(3,6-dihydro-2H-pyran-4-yl)-quinolin-4-yl]-3-pyrazin-2-yl-urea;
tert-butyl 4-[4-(3-pyrazin-2-ylureido)quinolin-6-yl]-5,6-dihydropyridine-1(2H)-carboxylate;
1-pyrazin-2-yl-3-[6-(1,2,3,6-tetrahydro-pyridin-4-yl)-quinolin-4-yl]-urea;
1-(6-piperidin-4-yl-quinolin-4-yl)-3-pyrazin-2-yl-urea;
1-{6-[1-(2-fluoro-ethyl)-piperidin-4-yl]-quinolin-4-yl}-3-pyrazin-2-yl-urea;
1-[6-(1-methyl-piperidin-4-yl)-quinolin-4-yl]-3-pyrazin-2-yl-urea;
tert-butyl 4-{4-[3-(6-cyclopropyl-pyrazin-2-yl)-ureido]-quinolin-6-yl}-3,6-dihydro-2H-pyridine-1-carboxylate;
tert-butyl 4-{4-[3-(6-cyclopropyl-pyrazin-2-yl)-ureido]-quinolin-6-yl}-piperidine-1-carboxylate;
1-(6-cyclopropyl-pyrazin-2-yl)-3-(6-piperidin-4-yl-quinolin-4-yl)-urea;
1-(6-cyclopropyl-pyrazin-2-yl)-3-[6-(1-methyl-piperidin-4-yl)-quinolin-4-yl]-urea;
tert-butyl 3-{4-[3-(6-Trifluoromethyl-pyridin-2-yl)-ureido]-quinolin-6-yl}-2,5-dihydropyrrole-1-carboxylate;
1-[6-(2,5-dihydro-1H-pyrrol-3-yl)-quinolin-4-yl]-3-(6-trifluoromethyl-pyridin-2-yl)-urea;
1-[6-(3,6-dihydro-2H-pyran-4-yl)-pyridin-2-yl]-3-(8-fluoro-quinolin-4-yl)-urea;
1-(8-fluoro-quinolin-4-yl)-3-[6-(tetrahydro-pyran-4-yl)-pyridin-2-yl]-urea;
1-(8-chloro-6-methyl-quinolin-4-yl)-3-[6-(tetrahydro-pyran-4-yl)-pyridin-2-yl]-urea;
1-(6,8-dichloro-quinolin-4-yl)-3-[6-(tetrahydro-pyran-4-yl)-pyridin-2-yl]-urea;
1-(6,8-difluoro-quinolin-4-yl)-3-[6-(tetrahydro-pyran-4-yl)-pyridin-2-yl]-urea;
1-(8-chloro-quinolin-4-yl)-3-[6-(tetrahydro-pyran-4-yl)-pyridin-2-yl]-urea;
1-[1,5]naphthyridin-4-yl-3-[6-(tetrahydro-pyran-4-yl)-pyridin-2-yl]-urea;
1-(5,8-difluoro-quinolin-4-yl)-3-[6-(tetrahydro-pyran-4-yl)-pyridin-2-yl]-urea;
1-(8-fluoro-6-methoxy-quinolin-4-yl)-3-[6-(tetrahydro-pyran-4-yl)-pyridin-2-yl]-urea;
1-[6-(5,6-dihydro-4H-pyran-3-yl)-pyridin-2-yl]-3-(8-fluoro-quinolin-4-yl)-urea;
1-(8-fluoro-quinolin-4-yl)-3-[6-(tetrahydro-pyran-3-yl)-pyridin-2-yl]-urea;
1-[6-(3,6-dihydro-2H-pyran-4-yl)-pyridin-2-yl]-3-[1,5]naphthyridin-4-yl-urea;
tert-butyl-6-[3-(8-fluoro-quinolin-4-yl)-ureido]-3',6'-dihydro-2'H-[2,4']bipyridinyl-1'-carboxylate;
1-(8-fluoro-quinolin-4-yl)-3-(1',2',3',6'-tetrahydro-[2,4]bipyridinyl-6-yl)-urea;
tert-butyl-6-[3-(8-fluoro-quinolin-4-yl)-ureido]-3',4',5',6'-tetrahydro-2'H-[2,4']bipyridinyl-1'-carboxylate;

1-(8-fluoro-quinolin-4-yl)-3-(1',2',3',4',5',6'-hexahydro-[2,4']bipyridinyl-6-yl)-urea;

1-(8-fluoro-quinolin-4-yl)-3-(1'-methyl-1',2',3',4',5',6'-hexahydro-[2,4']bipyridinyl-6-yl)-urea;

1-[1'-(2-fluoro-ethyl)-1',2',3',4',5',6'-hexahydro-[2,4']bipyridinyl-6-yl]-3-(8-fluoroquinolin-4-yl)-urea;

1-[1'-(2,2-difluoro-ethyl)-1',2',3',4',5',6'-hexahydro-[2,4']bipyridinyl-6-yl]-3-(8-fluoroquinolin-4-yl)-urea;

1-(8-fluoro-quinolin-4-yl)-3-(1'-isopropyl-1',2',3',4',5',6'-hexahydro-[2,4]bipyridinyl-6-yl)-urea;

1-(8-fluoro-quinolin-4-yl)-3-[5-(tetrahydro-pyran-4-yl)-pyridin-2-yl]-urea;

tert-butyl-3-[4-(3-pyrazin-2-yl-ureido)-quinolin-6-yl]-2,5-dihydro-pyrrole-1-carboxylate;

tert-butyl-3-[4-(3-pyrazin-2-yl-ureido)-quinolin-6-yl]-pyrrolidine-1-carboxylate; and 1-pyrazin-2-yl-3-(6-pyrrolidin-3-yl-quinolin-4-yl)-urea;

or a stereoisomer, N-oxide, tautomer or physiologically tolerated acid addition salt thereof.

23. The heterocyclic compound of claim 1, wherein at least one of the atoms has been replaced by its stable, non-radioactive isotope.

24. A pharmaceutical composition comprising at least one heterocyclic compound of claim 1, a stereoisomer, N-oxide, tautomer, and/or physiologically tolerated acid addition salt thereof, and at least one physiologically acceptable carrier and/or auxiliary substance.

25. A heterocyclic compound that is 1-(7-methoxyquinolin-4-yl)-3-(6-(trifluoromethyl)-pyridin-2-yl)urea, or a stereoisomer, N-oxide, tautomer, or physiologically tolerated acid addition salt thereof.

26. A heterocyclic compound that is 1-(8-fluoroquinolin-4-yl)-3-(6-(tetrahydro-2H-pyran-4-yl)pyridin-2-yl)urea, or a stereoisomer, N-oxide, tautomer, or physiologically tolerated acid addition salt thereof.

27. A heterocyclic compound that is 1-[1'-(2-fluoro-ethyl)-1',2',3',4',5',6'-hexahydro-[2,4']bipyridinyl-6-yl]-3-(8-fluoro-quinolin-4-yl)-urea, or a stereoisomer, N-oxide, tautomer, or physiologically tolerated acid addition salt thereof.

28. A heterocyclic compound that is 1-(7-methoxyquinolin-4-yl)-3-(6-(tetrahydro-2H-pyran-3-yl)pyridin-2-yl)urea, or a stereoisomer, N-oxide, tautomer, or physiologically tolerated acid addition salt thereof.

29. A heterocyclic compound that is 1-(8-fluoro-quinolin-4-yl)-3-(1',2',3',6'-tetrahydro-[2,4']bipyridinyl-6-yl)-urea, or a stereoisomer, N-oxide, tautomer, or physiologically tolerated acid addition salt thereof.

* * * * *